(12) United States Patent
Wehner et al.

(10) Patent No.: US 6,759,424 B2
(45) Date of Patent: Jul. 6, 2004

(54) IMIDAZOLIDINE DERIVATIVES, THEIR PREPARATION, THEIR USE, AND PHARMACEUTICAL PREPARATIONS COMPRISING THEM

(75) Inventors: Volkmar Wehner, Sandberg (DE); Hans Ulrich Stilz, Frankfurt (DE); Wolfgang Schmidt, Frankfurt (DE); Dirk Seiffge, Mainz-Kostheim (DE)

(73) Assignee: Aventis Pharma Deutschland GmbH, Frankfurt am Main (DE)

(*) Notice: Subject to any disclaimer, the term of this patent is extended or adjusted under 35 U.S.C. 154(b) by 5 days.

(21) Appl. No.: 10/147,921

(22) Filed: May 20, 2002

(65) Prior Publication Data

US 2003/0125565 A1 Jul. 3, 2003

Related U.S. Application Data

(62) Division of application No. 09/157,241, filed on Sep. 18, 1998, now Pat. No. 6,423,712.

(30) Foreign Application Priority Data

Sep. 18, 1997 (DE) .......................................... 197 41 235

(51) Int. Cl.[7] .................... C07D 233/02; A61K 31/4164
(52) U.S. Cl. .................... 514/389; 548/311.7; 546/210; 546/274.1; 544/139; 514/235.8; 514/326; 514/397
(58) Field of Search ....................... 548/311.7; 546/210, 546/274.1; 544/139; 514/389, 397

(56) References Cited

U.S. PATENT DOCUMENTS

| | | | |
|---|---|---|---|
| 4,344,949 A | 8/1982 | Hoefle et al. | 424/258 |
| 4,350,704 A | 9/1982 | Hoefle et al. | 424/274 |
| 4,374,847 A | 2/1983 | Gruenfeld | 424/274 |
| 5,242,939 A | 9/1993 | Sircar | |
| 5,389,614 A | 2/1995 | Koenig et al. | 514/18 |
| 5,397,796 A | 3/1995 | Zoller et al. | 514/389 |
| 5,424,293 A | 6/1995 | Zoller et al. | 514/20 |
| 5,554,594 A | 9/1996 | Zoller et al. | 514/18 |
| 5,658,935 A | 8/1997 | Klingler et al. | 514/359 |
| 5,686,421 A | 11/1997 | Koenig et al. | 514/18 |
| 5,688,913 A | 11/1997 | Arrhenius et al. | |
| 5,712,300 A | 1/1998 | Jacobsen | |
| 5,770,573 A | 6/1998 | Arrhenius et al. | |
| 5,821,231 A | 10/1998 | Arrhenius et al. | |

FOREIGN PATENT DOCUMENTS

| | | |
|---|---|---|
| DE | 235 866 | 5/1986 |
| EP | 0 029 488 | 6/1981 |
| EP | 0 031 741 | 7/1981 |
| EP | 0 046 953 | 3/1982 |
| EP | 0 049 605 | 4/1982 |
| EP | 0 049 858 | 4/1982 |
| EP | 0 050 800 | 5/1982 |
| EP | 0 079 022 | 5/1983 |

(List continued on next page.)

OTHER PUBLICATIONS

Albelda, S., et al., "Molecular and Cellular Properties of PECAM–1 (endoCAM/CD31): A Novel Vascular Cell–Cell Adhesion Molecule," Journal of Cell Biology, vol. 114, No. 5, pp. 1058–1068 (1991).

Anna, C., et al., "The VLA–4/VCAM–1 Pathway is Involved in Lymphocyte Adhesion to Endothelium in Rheumatoid Synovium," Journal of Immunology, vol. 147, No. 12, pp. 4207–4210 (1991).

Barbadillo, C., et al., "Anti–integrin Immunotheraphy in Rheumatoid Arthritis: Protective Effect of Anti–α–4 Antibody in Adjuvant Arthritis," Springer Seminars in Immunotheraphy, vol. 16 pp. 427–436 (1995).

(List continued on next page.)

*Primary Examiner*—Joseph K. McKane
*Assistant Examiner*—Golam M M Shamemm
(74) *Attorney, Agent, or Firm*—Heller Ehrman White and McAuliffe

(57) ABSTRACT

The present invention relates to novel imidazolidine derivatives of the formula I,

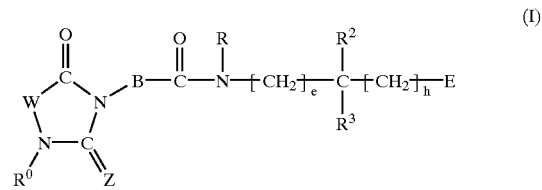

in which B, E, W, Z, R, $R^0$, $R^2$, $R^3$, e and h have the meanings indicated in the application. The compounds of the formula I are valuable pharmaceutical active compounds, which are suitable, for example, for the therapy and prophylaxis of inflammatory disorders, for example of rheumatoid arthritis, or of allergic disorders. The compounds of the formula I are inhibitors of the adhesion and migration of leucocytes and/or antagonists of the adhesion receptor VLA-4 belonging to the integrins group. They are generally suitable for the therapy or prophylaxis of illnesses which are caused by an undesired extent of leucocyte adhesion and/or leucocyte migration or are associated therewith, or in which cell-cell or cell-matrix interactions which are based on interactions of VLA-4 receptors with their ligands play a part. The invention furthermore relates to processes for the preparation of the compounds of the formula I, their use in the therapy and prophylaxis of the disease states mentioned and pharmaceutical preparations which contain compounds of the formula I.

8 Claims, No Drawings

FOREIGN PATENT DOCUMENTS

| | | |
|---|---|---|
| EP | 0 084 164 | 7/1983 |
| EP | 0 089 637 | 9/1983 |
| EP | 0 090 341 | 10/1983 |
| EP | 0 090 362 | 10/1983 |
| EP | 0 105 102 | 4/1984 |
| EP | 0 109 020 | 5/1984 |
| EP | 0 111 873 | 6/1984 |
| EP | 0 271 865 | 6/1988 |
| EP | 0 344 682 | 12/1989 |
| EP | 0 449 079 | 10/1991 |
| EP | 0 052 870 | 6/1992 |
| EP | 0 530 505 | 3/1993 |
| EP | 0 566 519 | 10/1993 |
| EP | 0 580 008 | 1/1994 |
| EP | 0 584 694 | 3/1994 |
| EP | 0 796 855 | 9/1997 |
| EP | 0 842 943 | 11/1997 |
| EP | 0 842 944 | 11/1997 |
| EP | 0 842 945 | 11/1997 |
| WO | WO 93/15764 | 6/1993 |
| WO | 93/13798 | 7/1993 |
| WO | 93/18057 | 9/1993 |
| WO | 94/15958 | 7/1994 |
| WO | WO 94/16094 | 7/1994 |
| WO | WO 94/17828 | 8/1994 |
| WO | 95/14008 | 5/1995 |
| WO | 95/15973 | 6/1995 |
| WO | WO 95/19790 | 7/1995 |
| WO | 96/00581 | 1/1996 |
| WO | 96/06108 | 2/1996 |
| WO | 96/20216 | 7/1996 |
| WO | 96/22966 | 8/1996 |
| WO | 96/33976 | 10/1996 |
| WO | 97/03094 | 1/1997 |
| WO | 98/04247 | 2/1998 |
| WO | 98/04913 | 2/1998 |
| WO | 98/42656 | 10/1998 |

OTHER PUBLICATIONS

Bergelson, J., et al., "Do Integrins Use a 'MIDAS Touch' to Grasp an Asp?" Current Biology, vol. 5, No. 6, pp. 615–617 (1995).

Bergeron, R., et al., "Total Synthesis of (±)–15–Deoxyspergualin," J. Org. Chem., vol. 52, pp. 1700–1703 (1987).

Borne, R., et al., "Conformational Analogues of Antihypertensive Agents Related to Guanethidine<" Journal of Medicinal Chemistry, vol. 20, No. 6, pp. 771–776 (1977).

Bundgaard, H., "Novel Chemical Approaches in Prodrug Design," Drugs of the Future, vol. 16, No. 5, pp. 443–458 (1991).

Büllesbach, E. "Protection in Peptide Synthesis (Part II): Multifunctional Amino Acids—Cleavene of Protecting Groups—Outlook on the Technique of Protection," KONTAKTE, vol. 1, No. 80, pp. 23–35 (1980).

Damle, N., et al., "Vascular Cell Adhesion Molecule 1 Induces T–cell Antigen Receptor–Dependent Activation of CD4+T Lymphocytes," Proc. Nat'l. Acad. Sci. USA, vol. 88, pp. 6403–6407 (1991).

Davies, S., et al., "Asymmetric Synthesis of R–β–Amino Butanoic Acid and S–β–Tyrosine: Homochiral Uthium Amide Equivalents for Michael Additions to a,β–Unsaturated Esters," Tetrahedron: Asymmetry, vol. 2, No. 3, pp. 183–185 (1991).

Elices, M.J., et al., "The Integrin VLA–4 Mediates Leukocyte Recruitment to Skin Inflammatory Sites In Vivo," Clinical and Experimental Rheumatology, vol. 11; Supp. 8, pp. 577–580 (1993).

Elices, M.J., et al., "Expression and Functional Significance of Alternatively Spliced CS1 Fibronectin in Rheumatoid Arthritis Microvasculature," J. Clin. Invest., vol. 93, pp. 405–416 (1994).

Elices, M.J., "The Integrin $\alpha_4\beta_1$ (VLA–4) As a Therapeutic Target," Ciba Foundation Symposium, vol. 189, pp. 79–90 (1995).

Fleisher, D., et al., "Improved Oral Drug Delivery: Solubility Limitations Overcome by the Use of Prodrugs," Advanced Drug Delivery Reviews, vol. 19, pp. 115–130 (1996).

Freedman, A., et al., "Follicular Non–Hodgkin's Lymphoma Cell Adhesion to Normal Germinal Centers and Neoplastic Follicles Involves Very Late Antigen–4 and Vascular Cell Adhesion Molecule–1," Blood, vol. 79, No. 1, pp. 206–212 (1992).

Goldschmidt, V.S., et al., "Über Peptid–Synthesen I," Liebigs. Ann. Chem., vol. 575, pp. 217–231 (1952).

Hafner, L.S., et al., "Preparation of 2–Imino– and 2–Nitrimino–1,3–diazacycloalkanes," J. Am. Chem. Soc., vol. 79, pp. 1157–1159 (1957).

Harlan, J., "Leukocyte–Endothelial Interactions," Blood, vol. 65, No. 3, pp. 513–525 (1985).

Hubbuch, A., "Schutzgruppen in der Peptidsynthase (Part I): Schutzgruppentektik, Amino– and Carboxyl–Schutzgruppen," KONTAKTE, vol. 3, No. 79, pp. 14–23 (1979).

Isobe, M., et al, "Effect of Anti–VCAM–1 and Anti–VLA–4 Monoclonal Antibodies on Cardiac Allograft Survival and Response to Soluble Antigens in Mice," Transplantation Proceedings, vol. 26, No. 2, pp. 867–868 (1994).

Issekutz, T., "Inhibition of In Vivo Lymphocyte Migration to Inflammation and Homing to Lymphoid Tissues by the TA–2 Monoclonal Antibody," Journal of Immunology, vol. 147, No. 12, pp. 4178–4184 (1991).

Kim, K., et al., "Monosubstituted Guanldines from Primary Amines and Aminoiminomethanesulfonic Acid," Tetrahedron Letters, vol. 29, No. 26, pp. 3183–3185 (1988).

Kulipers, T., "Pathophysiological Aspects of VLA–4 Interactions and Possibilities for Therapeutical Interventions," Springer Seminars in Immunopathology, vol. 16, pp. 379–389 (1995).

Laffon, A., et al., "Upregulated Expression and Function of VLA–4 Fibronectin Receptors on Human Activated T–Cells in Rheumatoid Arthritis," J. Clin. Invest., vol. 88, pp. 546–552 (1991).

Morales–Ducret, J., et al., "$\alpha_4\beta_1$ Integrin (VLA–4) Ligands in Arthritis: Vascular Cell Adhesion Molecule–1 Expression in Synovium and on Fibroblast–Like Synoviocytes," Journal of Immunology, vol. 143, No. 4, pp. 1424–1431 (1992).

Muacevic, G., "New Apparatus and Method for the Toxicological Investigation of Metered Aerosols in Rats," Arch. Toxicol., vol. 34, pp. 1–8 (1975).

Nielson, N., et al., "Glycolamide Esters as Biolabile Prodrugs of Carboxylic Acid Agents: Synthesis, Stability, Bioconversion, and Physiochemical Properties," Journal of Pharmaceutical Sciences, vol. 77, No. 4, pp. 285–298 (1988).

Nowick, J., et al., "Synthesis of Peptide Isocyanates and Isothiocynates," J. Org. Chem, vol. 61, pp. 3929–3934 (1996).

O'Brien, K., et al., "Vascular Cell Adhesion Molecule–1 is Expressed in Human Coronary Atherosclerotic Plaques," J. Clin. Invest., vol. 92, pp. 945–951 (1993).

Ockenhouse, C., et al., "Human Vascular Endothelial Cell Adhesion Receptors for *Plasmodium falciperum*–infected Erythrocytes: Roles for Endothelial Leukocyte Adhesion Molecule 1 and Vascular Cell Ahesion Molecule 1," Journal of Experimental Medicine, vol. 176, pp. 1183–1189 (1992).

Osborn, L., et al., "Direct Expression Cloning of Vascular Cell Adhesion Molecule 1, a Cytokine–Induced Endothelial Protein that Binds to Lymphocytes," Cell, vol. 59, pp. 1203–1211 (1989).

Osborn, L., "Leukocyte Adhesion to Endothelium in Inflammation," Cell, vol. 62, pp. 3–6 (1990).

Postigo, A., et al., "Increased Binding of Synovial T. Lymphocytes from Rheumatoid Arthritis to Endothelial–Leukocyte Adhesion Molecule–1 (ELAM–1) and Vascular Cell Adhesion Molecule–1 (VCAM–1), J. Clin. Invest., vol. 89, pp 1445–1452 (1992).

Renkonen, R., et al., "Rapid Communication: Expression of Endothelial Adhesion Molecules In Vivo," Journal of Pathology, vol. 140, No. 4, pp. 763–767 (1992).

Rice, G., et al., "An Inducible Endothelial Cell Surface Glycoprotein Mediates Melanoma Adhesion," Science, vol. 246, pp. 1303–1306 (1989).

Ruoslahti, E., "Fibronectin and its Receptors," Ann. Rev. Biochem., vol. 57, pp. 375–413 (1988).

Safadi, M., et al., "Phosphoryloxymethyl Carbamates and Carbonates—Novel Water–Soluble Prodrugs for Amines and Hindered Alcohols," Pharmaceutical Research, vol. 10, No. 9, pp. 1350–1354 (1993).

Saulnier, M., et al., "An Efficient Method for the Synthesis of Guanidine Prodrugs," Bioorganic & Medicinal Chemistry Letters, vol. 4, No. 16, pp. 1985–1990 (1994).

Scott, F., et al., "Studies in the Pyrazole Series," Pyrazole Series: Substituted Guanidines, vol. 75, pp. 4053–4054 (1953).

Seiffge, D., et al., "Effects of Different Mediators or Cytokines and Monoclonal Antibodies to Adhesion Molecules on Leukocyte Adhesion in Rat Mesenteric Venules," Int. J. Microcirc., vol. 15, pp. 301–308 (1995).

Springer, T., "Traffic Signals for Lymphocyte Recirculation and Leukocyte Emigration: The Multistep Paradigm," Cell, vol. 76, pp. 301–314 (1994).

Stoolman, L., "Adhesion Molecules Controlling Lymphocyte Migration," Cell, vol. 56, pp. 907–910 (1989).

Takeuchi, T., et al., "Upregulated Expression and Function of Integrin Adhesive Receptors in Systemic Lupus Erythematosus Patients with Vasculitis," J. Clin. Invest., vol. 92, pp. 3008–3016 (1993).

Tropp, C., "Einwirkung von Phosgen auf Polypeptidartige Derivate der p–Amino–benzosilure: Bildung von 1.3–substi–tuierten Hydantoinen," Chem. Ber. vol. 61, pp. 1431–1439 (1928).

Von Hans, T., et al., "Über die Bildung Substituierter Hydantoine aus Aldehyden und Katonen," Journal f0r prakishche Chemie N.F., vol. 141, pp. 5–43 (1934).

Wagner, G., et al., "Synthese von 3–[Amidinophenyl]–ataninen und 3–[Amidinophenyl]–milchadren," Pharmaze, vol. 29, No. 1, pp. 12–15 (1974).

Weiss, S., et al., "Zur Guanylierung von Aminen mit O–Methyl–Isohamstoff–sulfet," Chemiker–Zeitung, vol. 98, No. 12, pp. 617–618 (1974).

Wollweber, H., et al., "2–(Guandino)–anlide und Verwendte Verbindungen," Arzneim–Forsch./Drug Res., vol. 34, No. 5, (1984).

Yang, X., et al., "Inhibition of Instilitis and Prevention of Diabetes in Nonobese Diabetic Mice by Blocking L–selectin and Very Late Antigen–4 Adhesion Receptors," Proc. Nat'l. Acad. Sci. USA, vol. 90, pp. 10494–10498 (1993).

Yednock, T., et al., "Prevention of Experimental Autoimmune Encephalomyelitis by Antibodies Against $\alpha_4\beta_1$ Integrin," Nature, vol. 356, pp. 63–66 (1992).

Zettlmeissl, G., et al., "Expression and Characterization of Human CD4: Immunoglobulin Fusion Proteins," DNA and Cell Biology, vol. 9, No. 5, pp. 347–353 (1990).

Cronstein, Bruce N. et al., "The Adhesion Molecules of Inflammation". Arthritis and Rheumatism, vol. 36(2): pp. 147–157(1993).

Elices, Mariano J. et al., "VCAM–1 on Activated Endothelium Interacts with the Leukocyte Integrin VLA–4 at a Site Distinct from the VLA–4/Fibronectin Binding Site". Cell, vol. 60; pp. 577–584(1990).

Foster, Carolyn A, et al., "VCAM–1/α4–integrin adhesion pathway: Therapeutic target for allergic inflammatory disorders". Jour. Allergy Clin. Immunol., vol. 96(6): pp. S270–S277(1996).

Kilger et al., "Molecular analysis of the physiological and pathophysiological role of α4–integrins". J. Mol. Med., vol. 73; pp. 347–354(1995).

Issekutz, Thomas B. et al., Rat Blood Neutrophils Express Very Late Antigen 4 and it Mediates Migration to Arthritic Joint and Dermal Inflammation. J. Exp. Med., vol. 183: pp. 2175–2184(1996).

McMurray, Robert W., "Adhesion Molecules in Autoimmune Disease". Seminars in Arthritis and Rheumatism, vol. 25(4); pp. 215–233(1996).

IMIDAZOLIDINE DERIVATIVES, THEIR PREPARATION, THEIR USE, AND PHARMACEUTICAL PREPARATIONS COMPRISING THEM

This application is a divisional of application Ser. No. 09/157,241 filed Sep. 18, 1998. Now U.S. Pat. No. 6,423,712.

BACKGROUND OF THE INVENTION

1. Field of the Invention

The present invention relates to imidazolidine derivatives of the formula I,

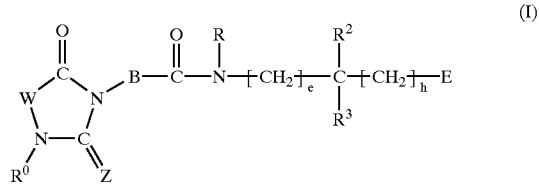

in which B, E, W, Z, R, $R^0$, $R^2$, $R^3$, e, and h have the meanings indicated below. The compounds of the formula I are valuable pharmaceutically active compounds, which are suitable, for example, for the therapy and prophylaxis of inflammatory disorders, for example, of rheumatoid arthritis, or of allergic disorders The compounds of the formula I are inhibitors of the adhesion and migration of leucocytes and/or are antagonists of the integrin adhesion receptor VLA-4. They are generally suitable for the therapy or prophylaxis of illnesses which are caused by or associated with an undesired extent of leucocyte adhesion and/or leucocyte migration, or in illnesses in which cell-cell or cell-matrix interactions which are based on VLA-4 receptor/ligand interactions. The invention furthermore relates to processes for the preparation of the compounds of the formula I, their use in the therapy and prophylaxis of the disease states mentioned, and pharmaceutical preparations which contain compounds of the formula I.

2. Description of Related Art

The integrins are a group of adhesion receptors which play an important part in cell-cell-binding and cell-extracellular matrix-binding processes. They have an αβ-heterodimeric structure and exhibit a wide cellular distribution and are highly conserved in evolution. The integrins include, for example, the fibrinogen receptor on platelets, which interacts especially with the RGD sequence of fibrinogen, or the vitronectin receptor on osteoclasts, which interacts especially with the RGD sequence of vitronectin or of osteopontin. The integrins are divided into three major groups, the β2 subfamily with the representatives LFA-1, Mac-1 and p150/95, which are responsible in particular for cell-cell interactions of the immune system, and the subfamilies β1 and β3, whose representatives mainly mediate cell adhesion to components of the extracellular matrix (Ruoslahti, Annu. Rev. Biochem. 1988, 57, 375). The integrins of the β1 subfamily, also called VLA proteins (very late (activation) antigen), include at least six receptors which interact specifically with fibronectin, collagen and/or laminin as ligands. Within the VLA family, the integrin VLA-4 (α4β1) is a typical, insofar as it is mainly restricted to lymphoid and myeloid cells where it is responsible for cell-cell interactions with a large number of other cells. For example, VLA-4 mediates the interaction of T and B lymphocytes with the heparin II-binding fragment of human plasma fibronectin (FN). The binding of VLA-4 with the heparin II-binding fragment of plasma fibronectin is especially based on an interaction with an LDVP sequence. In contrast to the fibrinogen or vitronectin receptor, VLA-4 is not a typical RGD-binding integrin (Kilger and Holzmann, J. Mol. Meth. 1995, 73, 347).

The leucocytes circulating in the blood normally exhibit only a low affinity for the vascular endothelial cells which line the blood vessels. Cytokines which are released from inflamed tissue cause the activation of endothelial cells and thus the expression of a large number of cell surface antigens. These include, for example, the adhesion molecules ELAM-1 (endothelial cell adhesion molecule-1; also designated as E-selectin), which, inter alia, binds neutrophils, ICAM-1 (intercellular adhesion molecule-1), which interacts with LFA-1 (leucocyte function-associated antigen 1) on leucocytes, and VCAM-1 (vascular cell adhesion molecule-1), which binds various leucocytes, inter alia lymphocytes (Osborn et al., Cell 1989, 59, 1203). VCAM-1, like ICAM-1, is a member of the immunoglobulin gene superfamily. VCAM-1 (first known as INCAM-110) was identified as an adhesion molecule which is induced on endothelial cells by inflammatory cytokines such as TNF and IL-1 and lipopolysaccharides (LPS). Elices et al., (Cell 1990, 60, 577) showed that VLA-4 and VCAM-1 form a receptor-ligand pair which mediates the adhesion of lymphocytes to activated endothelium. The binding of VCAM-1 to VLA-4 does not take place via an interaction of VLA-4 with an RGD sequence; this sequence is not contained in VCAM-1 (Bergelson et al., Current Biology 1995, 5, 615). VLA-4, however, also occurs on other leucocytes, and the adhesion of leucocytes other than lymphocytes is also mediated via the VCAM-1/VLA-4 adhesion mechanism. VLA-4 thus represents an individual example of a β1 integrin receptor which, via the ligands VCAM-1 and fibronectin, plays an important part both in cell-cell interactions and in cell-extracellular matrix interactions.

The cytokine-induced adhesion molecules play an important part in the recruitment of leucocytes into extravascular tissue regions. Leucocytes are recruited into inflammatory tissue regions by cell adhesion molecules which are expressed on the surface of endothelial cells and serve as ligands for leucocyte cell surface proteins or protein complexes (receptors) (the terms ligand and receptor can be considered interchangeable here.) Leucocytes from the blood must first adhere to endothelial cells before they can migrate into the synovium. Since VCAM-1 binds to cells which carry the integrin VLA-4 (α4β1), such as eosinophils, T and B lymphocytes, monocytes or neutrophils, the VCAM-1/VLA-4 mechanism has the function of recruiting cells of this type from the blood stream into areas of infection and inflammatory foci (Elices et al., Cell 1990, 60, 577; Osborn, Cell 1990, 62, 3; Issekutz et al., J. Exp. Med. 1996, 183, 2175).

The VCAM-1/VLA-4 adhesion mechanism has been connected with a number of physiological and pathological processes. Apart from cytokine-activated endothelium, VCAM-1 is additionally expressed, inter alia, by the following cells: myoblasts, lymphoid dendritic cells and tissue macrophages, rheumatoid synovium, cytokine-stimulated neural cells, parietal epithelial cells of the Bowman's capsule, the renal tubular epithelium, inflamed tissue during heart and kidney transplant rejection and by intestinal tissue in graft-versus-host disease. VCAM-1 is also expressed on those tissue areas of the arterial endothelium which correspond to early arteriosclerotic plaques of a rabbit model. Additionally, VCAM-1 is expressed on follicular dendritic cells of human lymph nodes and is found on stroma cells of the bone marrow, for example in the mouse. The latter finding points to a function of VCAM-1 in B-cell development. Apart from cells of hematopoietic origin, VLA-4 is also found, for example, on melanoma cell lines, and the VCAM-1/VLA-4 adhesion mechanism is connected with the metastasis of such tumors (Rice et al., Science 1989, 246, 1303).

The main form in which VCAM-1 occurs in vivo on endothelial cells and which is the dominant form in vivo is designated as VCAM-7D and carries seven immunoglobulin domains. The domains 4, 5 and 6 are similar in their amino acid sequences to the domains 1, 2 and 3. The fourth domain is removed in a further form, consisting of six domains, designated here as VCAM-6D, by alternative splicing. VCAM-6D can also bind VLA-4-expressing cells.

Further details on VLA-4, VCAM-1, integrins and adhesion proteins are found, for example, in the articles by Kilger and Holzmann, J. Mol. Meth. 1995, 73, 347; Elices, Cell Adhesion in Human Disease, Wiley, Chichester 1995, p. 79; and Kuijpers, Springer Semin. Immunopathol. 1995, 16, 379.

On account of the role of the VCAM-1/VLA-4 mechanism in cell adhesion processes, which are important, for example, in infections, inflammations or atherosclerosis, attempts have been made to intervene in these adhesion processes to control illnesses, in particular, for example, in inflammation (Osborn et al., Cell 1989, 59, 1203). A method of doing this is the use of monoclonal antibodies which are directed against VLA-4. Monoclonal antibodies (mAB) of this type, which act as VLA-4 antagonists to block the interaction between VCAM-1 and VLA-4, are known. Thus, for example, the anti-VLA-4 mAB HP2/1 and HP1/3 inhibit the adhesion of VLA-4-expressing Ramos cells (B-cell-like cells) to human umbilical cord endothelial cells and to VCAM-1-transfected COS cells. The anti-VCAM-1 mAB 4B9 likewise inhibits the adhesion of Ramos cells, Jurkat cells (T-cell-like cells) and HL60 cells (granulocyte-like cells) to COS cells transfected expressing VCAM-6D and VCAM-7D in vitro data with antibodies directed against the $\alpha 4$ subunit of VLA-4 show that adhesion of lymphocytes to synovial endothelial cells is blocked, an adhesion which plays a part in rheumatoid arthritis (van Dinther-Janssen et al., J. Immunol. 1991, 147, 4207).

In vivo experiments have shown that an experimental autoimmune encephalomyelitis can be inhibited by anti-$\alpha 4$ mAB. The migration of leucocytes into an inflammatory focus is likewise blocked by a monoclonal antibody against the $\alpha 4$ chain of VLA-4. The influencing of the VLA-4-dependent adhesion mechanism by antibodies was also investigated in an asthma model in order to investigate the role of VLA-4 in the recruitment of leucocytes into inflamed lung tissue (U.S. Ser. No. 07/821,768; EP-A-626 861). The administration of anti-VLA-4 antibodies inhibited the late-phase reaction and airway overreaction in allergic sheep.

The VLA-4-dependent cell adhesion mechanism was also investigated in a primate model of inflammatory bowel disease (IBD). In this model, which corresponds to ulcerative colitis in man, the administration of anti-VLA-4 antibodies resulted in a significant reduction in the acute inflammation.

Moreover, it was possible to show that VLA-4-dependent cell adhesion plays a part in the following clinical conditions including the following chronic inflammatory processes: rheumatoid arthritis (Cronstein and Weismann, Arthritis Rheum. 1993, 36, 147; Elices et al., J. Clin. Invest. 1994, 93, 405), diabetes mellitus (Yang et al., Proc. Natl. Acad. Sci. USA 1993, 90, 10494), systemic lupus erythematosus (Takeuchi et al., J. Clin. Invest. 1993, 92, 3008), allergies of the delayed type (type IV allergy) (Elices et al., Clin. Exp. Rheumatol 1993, 11, S77), multiple sclerosis (Yednock et al., Nature 1992, 356, 63), malaria (Ockenhouse et al., J. Exp. Med. 1992, 176, 1183), arteriosclerosis (O'Brien et al., J. Clin. Invest. 1993, 92, 945), transplantation (Isobe et al., Transplantation Proceedings 1994, 26, 867–868), various malignancies, for example melanoma (Renkonen et al., Am. J. Pathol. 1992, 140, 763), lymphoma (Freedman et al., Blood 1992, 79, 206) and others (Albelda et al., J. Cell Biol. 1991, 114, 1059).

VLA-4 blocking by suitable antagonists accordingly offers effective therapeutic possibilities, in particular, for example, of treating various inflammatory conditions including asthma and IBD. The particular relevance of VLA-4 antagonists for the treatment of rheumatoid arthritis in this case results, as already stated, from the fact that leucocytes from the blood must first adhere to endothelial cells before they can migrate into the synovium, and that the VLA-4 receptor plays a part in this adhesion. The fact that VCAM-1 is induced by inflammatory agents on endothelial cells (Osborn, Cell 1990, 62, 3; Stoolman, Cell 1989, 56, 907), and the recruitment of various leucocytes into areas of infection and inflammatory foci has already been discussed above. In this respect, T cells adhere to activated endothelium mainly via the LFA-1/ICAM-1 and VLA-4/VCAM-1 adhesion mechanisms (Springer, Cell 1994, 76, 301). On most synovial T cells, the binding capacity of VLA-4 for VCAM-1 is increased in rheumatoid arthritis (Postigo et al., J. Clin. Invest. 1992, 89, 1445). Additionally, an increased adhesion of synovial T cells to fibronectin has been observed (Laffon et al., J. Clin. Invest. 1991, 88, 546; Morales-Ducret et al., J. Immunol. 1992, 149, 1424). VLA-4 is upregulated both in the course of its expression and with respect to its function on T lymphocytes of the rheumatoid synovial membrane. The blocking of the binding of VLA-4 to its physiological ligands VCAM-1 and fibronectin makes possible an effective prevention or alleviation of articular inflammatory processes. This is also confirmed by experiments with the antibody HP2/1 on Lewis rats with adjuvant arthritis, in which an effective prevention of illness has been observed (Barbadillo et al., Springer Semin. Immunopathol. 1995, 16, 427). VLA-4 is thus an important therapeutic target molecule.

The abovementioned VLA-4 antibodies and the use of antibodies as VLA-4 antagonists are described in the Patent Applications WO-A-93/13798, WO-A-93/15764, WO-A-94/16094, WO-A-94/17828, and WO-A-95/19790. In the Patent Applications WO-A-94/15958, WO-A-95/15973, WO-A-96/00581, WO-A-96/06108 and WO-A-96/20216, peptide compounds are described as VLA-4 antagonists. The use of antibodies and peptide compounds as pharmaceuticals, however, has some disadvantages, for example lack of oral availability, rapid degradation or immunogenicity on longer-term use. There is thus a need for VLA-4 antagonists having improved properties for use in therapy and prophylaxis.

WO-A-95/14008, WO-A-94/21607, WO-A-93/18057, EP-A-449 079, EP-A-530 505 (U.S. Pat. No. 5,389,614), EP-A-566 919 (U.S. Pat. No. 5,397,796), EP-A-580 008 (U.S. Pat. No. 5,424,293) and EP-A-584 694 (U.S. Pat. No. 5,554,594) describe substituted 5-membered ring heterocycles which have an amino, amidino or guanidino function at the N-terminal end of the molecule and which exhibit platelet aggregation-inhibiting actions. EP-A-796 855 (European Patent Application 97103712.2) describes further heterocycles which are inhibitors of bone resorption. EP-A-842 943, EP-A-842 945 and EP-A-842 944 (German Patent Applications 19647380.2, 19647381.0 and 19647382.9) describe that certain compounds from this series and certain further compounds surprisingly also inhibit leucocyte adhesion and are VLA-4 antagonists. However, the selected compounds of the formula I according to the present invention, which are distinguished by their VLA-4 antagonism and/or their inhibitory action on leucocyte adhesion and leucocyte migration and are the subject of the present invention, are not disclosed or suggested in the applications mentioned.

The present invention thus relates to compounds of the formula I,

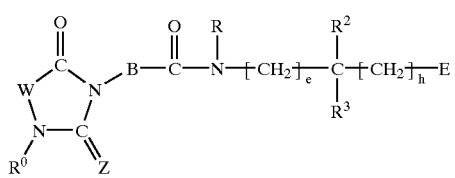

(I)

in which

W is $R^1$—A—$C(R^{13})$ or $R^1$—CH=C;

Z is oxygen or sulfur;

A is a direct bond or $(C_1-C_2)$-alkylene;

B is a divalent radical selected from the group of $(C_1-C_6)$-alkylene, $(C_2-C_6)$-alkenylene, phenylene, phenylene-$(C_1-C_3)$-alkyl, $(C_1-C_3)$-alkylenephenyl, where the divalent $(C_1-C_6)$-alkylene radical can be unsubstituted or substituted by a radical selected from the group consisting of $(C_1-C_8)$-alkyl, $(C_2-C_8)$-alkenyl, $(C_2-C_8)$-alkynyl, $(C_3-C_{10})$-cycloalkyl, $(C_3-C_{10})$-cycloalkyl-$(C_1-C_6)$-alkyl, optionally substituted $(C_6-C_{14})$-aryl, $(C_6-C_{14})$-aryl-$(C_1-C_6)$-alkyl optionally substituted in the aryl radical, optionally substituted heteroaryl, and heteroaryl-$(C_1-C_6)$-alkyl optionally substituted in the heteroaryl radical;

E is tetrazolyl, $(R^8O)_2P(O)$, $HOS(O)_2$, $R^9NHS(O)_2$, or $R^{10}CO$;

R is hydrogen, $(C_1-C_8)$-alkyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl or heteroaryl-$(C_1-C_8)$-alkyl optionally substituted in the heteroaryl radical;

$R^0$ is hydrogen, $(C_1-C_8)$-alkyl, $(C_3-C_{12})$-cycloalkyl, $(C_3-C_{12})$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical, H—CO, $(C_1-C_8)$-alkyl-CO, $(C_3-C_{12})$-cycloalkyl-CO, $(C_3-C_{12})$-cycloalkyl-$(C_1-C_8)$-alkyl-CO, $(C_6-C_{12})$-bicycloalkyl-CO, $(C_6-C_{12})$-bicycloalkyl-$(C_1-C_8)$-alkyl-CO, $(C_6-C_{12})$-tricycloalkyl-CO, $(C_6-C_{12})$-tricycloalkyl-$(C_1-C_8)$-alkyl-CO, optionally substituted $(C_6-C_{14})$-aryl-CO, $(C_6-C_{14})$-aryl-$(C_1-C_8)$-alkyl-CO optionally substituted in the aryl radical, optionally substituted heteroaryl-CO, heteroaryl-$(C_1-C_8)$-alkyl-CO optionally substituted in the heteroaryl radical, $(C_1-C_8)$-alkyl-$S(O)_n$, $(C_3-C_{12})$-cycloalkyl-$S(O)_n$, $(C_3-C_{12})$-cycloalkyl-$(C_1-C_8)$-alkyl-$S(O)_n$, $(C_6-C_{12})$-bicycloalkyl-$S(O)_n$, $(C_6-C_{12})$-bicycloalkyl-$(C_1-C_8)$-alkyl-$S(O)_n$, $(C_6-C_{12})$-tricycloalkyl-$S(O)_n$, $(C_6-C_{12})$-tricycloalkyl-$(C_1-C_8)$-alkyl-$S(O)_n$, optionally substituted $(C_6-C_{14})$-aryl-$S(O)_n$, $(C_6-C_{14})$-aryl-$(C_1-C_8)$-alkyl-$S(O)_n$ optionally substituted in the aryl radical, optionally substituted heteroaryl-$S(O)_n$ or heteroaryl-$(C_1-C_8)$-alkyl-$S(O)_n$ optionally substituted in the heteroaryl radical, where n is 1 or 2;

$R^1$ is an optionally substituted radical selected from the group consisting of phenyl, furyl, thienyl, pyrrolyl, imidazolyl and pyridyl, where each of these radicals can also be benzo-fused;

$R^2$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical or $(C_3-C_8)$-cycloalkyl;

$R^3$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical, $(C_3-C_8)$-cycloalkyl, $(C_3-C_8)$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, $(C_2-C_8)$-alkenyl, $(C_2-C_8)$-alkynyl, $R^{11}NH$, $CON(CH_3)R^4$, $CONHR^4$, $COOR^{15}$, $CON(CH_3)R^{15}$ or $CONHR^{15}$;

$R^4$ is hydrogen or $(C_1-C_{10})$-alkyl which can optionally be monosubstituted or polysubstituted by identical or different radicals selected from the group consisting of hydroxyl, $(C_1-C_8)$-alkoxy, $R^5$, optionally substituted $(C_3-C_8)$-cycloalkyl, hydroxycarbonyl, aminocarbonyl, mono- or di-$((C_1-C_{18})$-alkyl)-aminocarbonyl, $(C_6-C_{14})$-aryl-$(C_1-C_8)$-alkoxycarbonyl which can also be substituted in the aryl radical, $(C_1-C_8)$-alkoxycarbonyl, Het- CO, $R^6$—CO, tetrazolyl, and trifluoromethyl;

$R^5$ is optionally substituted $(C_6-C_{14})$-aryl, $(C_6-C_{14})$-aryl-$(C_1-C_8)$-alkyl optionally substituted in the aryl radical, or an optionally substituted monocyclic or bicyclic 5-membered to 12-membered heterocyclic ring which can be aromatic, partially hydrogenated or completely hydrogenated and which can contain one, two or three identical or different heteroatoms selected from the group consisting of nitrogen, oxygen, and sulfur;

$R^6$ is the radical of a natural or unnatural amino acid, imino acid, optionally N—$(C_1-C_8)$-alkylated or N—$((C_6-C_{14})$-aryl-$(C_1-C_8)$-alkylated) azaamino acid which can also be substituted in the aryl radical, or the radical of a dipeptide, and their esters and amides, where free functional groups can be protected by protective groups customary in peptide chemistry;

$R^8$ is hydrogen, $(C_1-C_{18})$-alkyl, optionally substituted $(C_6-C_{14})$-aryl or $(C_6-C_{14})$-aryl-$(C_1-C_8)$-alkyl which can also be substituted in the aryl radical;

$R^9$ is hydrogen, aminocarbonyl, $(C_1-C_{18})$-alkylaminocarbonyl, $(C_3-C_8)$-cycloalkylaminocarbonyl, optionally substituted $(C_6-C_{14})$-arylaminocarbonyl, $(C_1-C_{18})$-alkyl, optionally substituted $(C_6-C_{14})$-aryl or $(C_3-C_8)$-cycloalkyl;

$R^{10}$ is hydroxyl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, $(C_1-C_8)$-alkylcarbonyloxy-$(C_1-C_6)$-alkoxy, $(C_6-C_{14})$-arylcarbonyloxy-$(C_1-C_5)$-alkoxy, amino or mono- or di-$((C_1-C_{18})$-alkyl)-amino;

$R^{11}$ is hydrogen, $R^{12a}$, $R^{12a}$—CO, H—CO, $R^{12a}$—O—CO, $R^{12b}$—CO, $R^{12b}$—CS, $R^{12a}$—S(O)$_2$ or $R^{12b}$—S(O)$_2$;

$R^{12a}$ is (C$_1$–C$_{18}$)-alkyl, (C$_2$–C$_8$)-alkenyl, (C$_2$–C$_8$)-alkynyl, (C$_3$–C$_{12}$)-cycloalkyl, (C$_3$–C$_{12}$)-cycloalkyl-(C$_1$–C$_8$)-alkyl, optionally substituted (C$_6$–C$_{14}$)-aryl, (C$_6$–C$_{14}$)-aryl-(C$_1$–C$_8$)-alkyl optionally substituted in the aryl radical, optionally substituted heteroaryl, heteroaryl-(C$_1$–C$_8$)-alkyl optionally substituted in the heteroaryl radical, or the radical $R^{15}$;

$R^{12b}$ is amino, di-((C$_1$–C$_{18}$)-alkyl)-amino or $R^{12a}$—NH;

$R^{13}$ is hydrogen, (C$_1$–C$_6$)-alkyl, optionally substituted (C$_6$–C$_{14}$)-aryl, (C$_6$–C$_{14}$)-aryl-(C$_1$–C$_6$)-alkyl optionally substituted in the aryl radical, (C$_3$–C$_8$)-cycloalkyl or (C$_3$–C$_8$)-cyclo-(C$_1$–C$_6$)-alkyl;

$R^{15}$ is $R^{16}$—(C$_1$–C$_6$)-alkyl or $R^{16}$;

$R^{16}$ is a 6-membered to 24-membered bicyclic or tricyclic radical which is saturated or partially unsaturated and which can also contain one, two, three or four identical or different heteroatoms selected from the group of nitrogen, oxygen and sulfur and which can also be substituted by one or more identical or different substituents from the group consisting of (C$_1$–C$_4$)-alkyl and oxo;

Het is the radical of a 5-membered to 10-membered, saturated monocyclic or polycyclic heterocycle bonded via a ring nitrogen atom, which can contain one, two, three or four identical or different additional ring heteroatoms selected from the group consisting of oxygen, nitrogen and sulfur and which can optionally be substituted on carbon atoms and on additional ring nitrogen atoms, where substituents on additional ring nitrogen atoms can be identical or different radicals from the group consisting of hydrogen, $R^h$, HCO, $R^h$CO and $R^h$O—CO and $R^h$ is (C$_1$–C$_8$)-alkyl, (C$_3$–C$_8$)-cycloalkyl, (C$_3$–C$_8$)-cycloalkyl-(C$_1$–C$_8$)-alkyl, optionally substituted (C$_6$–C$_{14}$)-aryl or (C$_6$–C$_{14}$)-aryl-(C$_1$–C$_8$)-alkyl optionally substituted in the aryl radical;

e and h independently of one another are 0 or 1;

in any of their stereoisomeric forms and mixtures thereof in any ratios, and any of their physiologically tolerable salts.

DETAILED DESCRIPTION OF THE INVENTION

In the compounds of the invention, alkyl radicals can be straight-chain or branched. This also applies if alkyl radicals carry substituents or occur as substituents of other radicals, for example in alkoxy radicals, alkoxycarbonyl radicals, or arylalkyl radicals. The same applies to alkylene radicals. Examples of suitable (C$_1$–C$_{18}$)-alkyl radicals are methyl, ethyl, n-propyl, n-butyl, n-pentyl, n-hexyl, n-heptyl, n-octyl, n-decyl, n-undecyl, n-dodecyl, n-tridecyl, n-pentadecyl, n-hexadecyl, n-heptadecyl, n-octadecyl, isopropyl, isobutyl, isopentyl, isohexyl, 3-methylpentyl, neopentyl, neohexyl, 2,3,5-trimethylhexyl, sec-butyl, tert-butyl, and tert-pentyl. Preferred alkyl radicals are methyl, ethyl, n-propyl, isopropyl, n-butyl, isobutyl, sec-butyl, tert-butyl, n-pentyl, isopentyl, n-hexyl, and isohexyl. Examples of alkylene radicals are methylene, ethylene, tri-, tetra-, penta- and hexamethylene or methylene or ethylene substituted by an alkyl radical, for example, methylene which is substituted by a methyl group, an ethyl group, an isopropyl group, an isobutyl group, a tert-butyl group, an n-pentyl group, an isopentyl group or an n-hexyl group, or, for example, ethylene which can be substituted either on one carbon atom or on the other carbon atom or alternatively on both carbon atoms.

Alkenyl radicals and alkenylene radicals as well as alkynyl radicals can also be straight-chain or branched. Examples of alkenyl radicals are vinyl, 1-propenyl, allyl, butenyl, 3-methyl-2-butenyl, examples of alkenylene radicals are vinylene or propenylene and examples of alkynyl radicals are ethynyl, 1-propynyl, or propargyl.

Cycloalkyl radicals are, in particular, cyclopropyl, cyclobutyl, cyclopentyl, cyclohexyl, cycloheptyl, cyclooctyl, cyclononyl, cyclodecyl, cycloundecyl and cyclododecyl, which can also be substituted, for example, by (C$_1$–C$_4$)-alkyl. Examples of substituted cycloalkyl radicals include 4-methylcyclohexyl and 2,3-dimethylcyclopentyl. Cycloalkylene radicals may be substituted in the same way.

Bicycloalkyl radicals, tricycloalkyl radicals and the 6-membered to 24-membered bicyclic and tricyclic radicals representing $R^{16}$ are formally obtained by abstraction of a hydrogen atom from bicycles or tricycles. The basic bicycles and tricycles contain only carbon atoms as ring members, they can thus be bicycloalkanes or tricycloalkanes, but in the case of the radicals representing $R^{16}$ they can also contain one to four identical or different heteroatoms selected from the group consisting of nitrogen, oxygen and sulfur; they can thus be aza-, oxa- and tniabicyclo- and -tricycloalkanes. If heteroatoms are contained, preferably one or two heteroatoms, in particular nitrogen atoms or oxygen atoms, are contained. The heteroatoms can occupy any desired positions in the bicyclic or tricyclic structure; they can be located in the bridges or, in the case of nitrogen atoms, also on the bridgeheads. Both the bicycloalkanes and tricycloalkanes and their heteroanalogs can be completely saturated or can contain one or more double bonds; preferably they contain one or two double bonds or are, in particular, completely saturated. Both the bicycloalkanes and tricycloalkanes as well as the heteroanalogs and both the saturated and the unsaturated representatives can be unsubstituted or can be substituted in any desired suitable positions by one or more oxo groups and/or one or more identical or different (C$_1$–C$_4$)-alkyl groups, for example, methyl groups or isopropyl groups, preferably methyl groups. The free bond of the bicyclic or tricyclic radical can be located in any desired position of the molecule, and the radical can thus be bonded via a bridgehead atom or an atom in a bridge. The free bond can also be located in any desired stereochemical position, for example, in an exo position or an endo position.

Examples of parent structures of bicyclic ring systems, from which a bicyclic radical can be derived, are norbornane (=bicyclo[2.2.1]heptane), bicyclo[2.2.2]octane and bicyclo[3.2.1]octane, examples of heteroatom-containing, unsaturated or substituted ring systems are 7-azabicyclo[2.2.1]heptane, bicyclo[2.2.2]oct-5-ene and camphor (=1,7,7-trimethyl-2-oxobicyclo[2.2.1]heptane).

Examples of systems from which a tricyclic radical can be derived are twistane (=tricyclo[4.4.0.0$^{3,8}$]decane), adamantane (=tricyclo[3.3.1.1$^{3,7}$]decane), noradamantane (=tricyclo[3.3.1.0$^{3,7}$]nonane), tricyclo[2.2.1.0$^{2,6}$]heptane, tricyclo[5.3.2.0$^{4,9}$]dodecane, tricyclo[5.4.0.0$^{2,9}$]undecane or tricyclo[5.5.1.0$^{3,11}$]tridecane.

Preferably, bicyclic or tricyclic radicals are derived from bridged bicycles or tricycles, i.e., from systems in which rings have two or more than two atoms in common. Additionally preferred, if not stated otherwise, are also bicyclic or tricyclic radicals having 6 to 18 ring members, particularly preferably those having 6 to 14 ring members, very particularly preferably those having 7 to 12 ring members.

Specifically particularly preferred bicyclic and tricyclic radicals are the 2-norbornyl radical, having either the free bond in the exo position or having the free bond in the endo position; the 2-bicyclo[3.2.1]octyl radical; the adamantyl radical; both the 1-adamantyl radical and the 2-adamantyl radical; the homoadamantyl radical and the noradamantyl radical, for example the 3-noradamantyl radical. Additionally preferred are the 1- and the 2-adamantyl radicals.

($C_6$–$C_{14}$)-aryl groups are, for example, phenyl, naphthyl, for example 1-naphthyl and 2-naphthyl, biphenylyl, for example 2-biphenylyl, 3-biphenylyl and 4-biphenylyl, anthryl or fluorenyl, ($C_6$–$C_{10}$)-aryl groups, for example 1-naphthyl, 2-naphthyl and in particular phenyl. Aryl radicals, in particular phenyl radicals, can be monosubstituted or polysubstituted, preferably monosubstituted, disubstituted or trisubstituted, by identical or different radicals from the group consisting of ($C_1$–$C_8$)-alkyl, in particular ($C_1$–$C_4$)-alkyl, ($C_1$–$C_8$)-alkoxy, in particular ($C_1$–$C_4$)-alkoxy, halogen, nitro, amino, trifluoromethyl, hydroxyl, hydroxy-($C_1$–$C_4$)-alkyl such as, for example, hydroxymethyl or 1-hydroxyethyl or 2-hydroxyethyl, methylenedioxy, ethylenedioxy, formyl, acetyl, cyano, hydroxycarbonyl, aminocarbonyl, ($C_1$–$C_4$)-alkoxycarbonyl, phenyl, phenoxy, benzyl, benzyloxy, tetrazolyl. The same applies, for example to radicals such as arylalkyl or arylcarbonyl. Arylalkyl radicals are, in particular, benzyl and 1- and 2-naphthylmethyl, 2-, 3- and 4-biphenylylmethyl and 9-fluorenylmethyl, which can also be substituted. Substituted arylalkyl radicals are, for example, benzyl radicals and naphthylmethyl radicals substituted in the aryl moiety by one or more ($C_1$–$C_8$)-alkyl radicals, in particular ($C_1$–$C_4$)-alkyl radicals, for example 2-, 3- and 4-methylbenzyl, 4-isobutylbenzyl, 4-tert-butylbenzyl, 4-octylbenzyl, 3,5-dimethylbenzyl, pentamethylbenzyl, 2-, 3-, 4-, 5-, 6-, 7- and 8-methyl-1-naphthylmethyl, 1-, 3-, 4-, 5-, 6-, 7- and 8-methyl-2-naphthylmethyl, benzyl radicals and naphthylmethyl radicals substituted in the aryl moiety by one or more ($C_1$–$C_8$)-alkoxy radicals, in particular ($C_1$–$C_4$)-alkoxy radicals, for example 4-methoxybenzyl, 4-neopentyloxybenzyl, 3,5-dimethoxybenzyl, 3,4-methylenedioxybenzyl, 2,3,4-trimethoxybenzyl, nitrobenzyl radicals, for example 2-, 3- and 4-nitrobenzyl, halobenzyl radicals, for example 2-, 3- and 4-chlorobenzyl and 2-, 3- and 4-fluorobenzyl, 3,4-dichlorobenzyl, pentafluorobenzyl, trifluoromethylbenzyl radicals, for example 3- and 4-trifluoromethylbenzyl or 3,5-bis(trifluoromethyl)benzyl. Substituted arylalkyl radicals, however, can also have different substituents.

In monosubstituted phenyl radicals, the substituent can be located in the 2-, the 3- or the 4-position, the 3- and the 4-position being preferred. If phenyl is disubstituted, the substituents can be in the 1,2-, 1,3- or 1,4-position relative to one another. Disubstituted phenyl can thus be substituted in the 2,3-position, 2,4-position, 2,5-position, the 2,6-position, 3,4-position or the 3,5-position, relative to the linkage site. Preferably, in disubstituted phenyl radicals the two substituents are arranged in the 3-position and the 4-position, relative to the linkage site. In trisubstituted phenyl radicals, the substituents can be present, for example, in the 2,3,4-position, the 2,3,5-position, the 2,4,5-position, the 2,4,6-position, the 2,3,6-position or the 3,4,5-position. The same applies to phenylene radicals, which can be present, for example as 1,4-phenylene or as 1,3-phenylene.

Phenylene-($C_1$–$C_3$)-alkyl is in particular phenylenemethyl (—$C_6H_4$—$CH_2$—) and phenyleneethyl, ($C_1$–$C_3$)-alkylenephenyl in particular methylenephenyl (—$CH_2$—$C_6H_4$—). Phenylene-($C_2$–$C_6$)-alkenyl is in particular phenyleneethenyl and phenylenepropenyl.

Heteroarys include monocyclic or polycyclic aromatic radicals having 5 to 14 ring members, which contains 1, 2, 3, 4 or 5 heteroatoms as ring members. Examples of heteroatoms are N, O and S. If several heteroatoms are contained, these can be identical or different. Heteroaryl radicals can also be monosubstituted or polysubstituted, preferably monosubstituted, disubstituted or trisubstituted, by identical or different radicals selected from the group consisting of ($C_1$–$C_8$)-alkyl, in particular ($C_1$–$C_4$)-alkyl, ($C_1$–$C_8$)-alkoxy, in particular ($C_1$–$C_4$)-alkoxy, halogen, nitro, amino, trifluoromethyl, hydroxyl, hydroxy-($C_1$–$C_4$)-alkyl such as, for example, hydroxymethyl or 1-hydroxyethyl or 2-hydroxyethyl, methylenedioxy, formyl, acetyl, cyano, hydroxycarbonyl, aminocarbonyl, ($C_1$–$C_4$)-alkoxycarbonyl, phenyl, phenoxy, benzyl, benzyloxy, or tetrazolyl. Preferably heteroaryl is a monocyclic or bicyclic aromatic radical which contains 1, 2, 3 or 4, in particular 1, 2 or 3, identical or different heteroatoms selected from the group consisting of N, O, and S and which can be substituted by 1, 2, 3 or 4, in particular 1, 2 or 3, identical or different substituents selected from the group of ($C_1$–$C_6$)-alkyl, ($C_1$–$C_6$)-alkoxy, fluorine, chlorine, nitro, amino, trifluoromethyl, hydroxyl, hydroxy-($C_1$–$C_4$)-alkyl, ($C_1$–$C_4$)-alkoxycarbonyl, phenyl, phenoxy, benzyloxy and benzyl. Particularly preferably, heteroaryl is a monocyclic or bicyclic aromatic radical having 5 to 10 ring members, in particular a 5-membered to 6-membered monocyclic aromatic radical which contains 1, 2 or 3, in particular 1 or 2, identical or different heteroatoms selected from the group consisting of N, O, and S and can be substituted by 1 or 2 identical or different substituents selected from the group consisting of ($C_1$–$C_4$)-alkyl, ($C_1$–$C_4$)-alkoxy, phenyl, phenoxy, benzyloxy, and benzyl.

Heterocycles representing monocyclic or bicyclic 5-membered to 12-membered heterocyclic rings can be aromatic or partially or completely saturated. They can be unsubstituted or substituted on one or more carbon atoms or on one or more nitrogen atoms by identical or different substituents, such as is indicated for the radical heteroaryl. In particular, the heterocyclic ring can be monosubstituted or polysubstituted on carbon atoms by identical or different radicals selected from the group consisting of ($C_1$–$C_8$)-alkyl, for example ($C_1$–$C_4$)-alkyl, ($C_1$–$C_8$)-alkoxy, for example ($C_1$–$C_4$)-alkoxy such as methoxy, phenyl-($C_1$–$C_4$)-alkoxy, for example benzyloxy, hydroxyl, oxo, halogen, nitro, amino or trifluoromethyl, and/or ring nitrogen atoms in heterocyclic rings and in heteroaryl radicals can be substituted by ($C_1$–$C_8$)-alkyl, for example ($C_1$–$C_4$)-alkyl such as methyl or ethyl, or by optionally substituted phenyl or phenyl-($C_1$–$C_4$)-alkyl, for example, benzyl.

Examples of heterocycles on which the heteroaryl radical or the radical of the monocyclic or bicyclic 5-membered to 12-membered heterocyclic ring can be based are pyrrole, furan, thiophene, imidazole, pyrazole, oxazole, isoxazole, thiazole, isothiazole, tetrazole, pyridine, pyrazine, pyrimidine, indole, isoindole, indazole, phthalazine, quinoline, isoquinoline, quinoxaline, quinazoline, cinnoline, β-carboline or benzo-fused, cyclopenta-fused, cyclohexa-fused or cyclohepta-fused derivatives of these heterocycles.

Nitrogen heterocycles can also be present as N-oxides.

Radicals which can be heteroaryl or the radical of a monocyclic or bicyclic 5-membered to 12-membered heterocyclic ring are, for example, 2- or 3-pyrrolyl, phenylpyrrolyl, for example 4- or 5-phenyl-2-pyrrolyl, 2-furyl, 3-furyl, 2-thienyl, 3-thienyl, 4-imidazolyl, methylimidazolyl, for example 1-methyl-2-, -4- or -5-imidazolyl, 1,3-thiazol-2-yl, 2-pyridyl, 3-pyridyl, 4-pyridyl, N-oxido-2-, -3- or -4-pyridyl, 2-pyrazinyl, 2-, 4- or 5-pyrimidinyl, 2-, 3- or 5-indolyl, substituted 2-indolyl, for example 1-methyl-, 5-methyl-, 5-methoxy-, 5-benzyloxy-, 5-chloro- or 4,5-dimethyl-2-indolyl, 1-benzyl-2- or -3-indolyl, 4,5,6,7-tetrahydro-2-indolyl, cyclohepta[b]-5-pyrrolyl, 2-, 3- or 4-quinolyl, 1-, 3- or 4-isoquinolyl, 1-oxo-1,2-dihydro-3-isoquinolyl, 2-quinoxalinyl, 2-benzofuranyl, 2-benzothienyl, 2-benzoxazolyl or 2-benzothiazolyl or, as radicals of partially hydrogenated or completely hydrogenated heterocyclic rings, for example also dihydropyridinyl, pyrrolidinyl, for example 2- or 3-(N-methylpyrrolidinyl), piperazinyl, morpholinyl, thiomorpholinyl, tetrahydrothienyl, benzodioxolanyl.

Heterocyclic radicals representing the radical Het can be unsubstituted on carbon atoms and/or ring nitrogen atoms or monosubstituted or polysubstituted, for example disubstituted, trisubstituted, tetrasubstituted or pentasubstituted, by identical or different substituents. Carbon atoms can be substituted, for example, by $(C_1-C_8)$-alkyl, in particular $(C_1-C_4)$-alkyl, $(C_1-C_8)$-alkoxy, in particular $(C_1-C_4)$-alkoxy, halogen, nitro, amino, trifluoromethyl, hydroxyl, oxo, cyano, hydroxycarbonyl, aminocarbonyl, $(C_1-C_4)$-alkoxycarbonyl, phenyl, phenoxy, benzyl, benzyloxy, tetrazolyl, in particular by $(C_1-C_4)$-alkyl, for example methyl, ethyl or tert-butyl, $(C_1-C_4)$-alkoxy, for example methoxy, hydroxyl, oxo, phenyl, phenoxy, benzyl, benzyloxy. Sulfur atoms can be oxidized to the sulfoxide or to the sulfone. Examples of the radical Het are 1-pyrrolidinyl, 1-piperidinyl, 1-piperazinyl, 4-substituted 1-piperazinyl, 4-morpholinyl, 4-thiomorpholinyl, 1-oxo-4-thiomorpholinyl, 1,1-dioxo-4-thiomorpholinyl, perhydroazepin-1-yl, 2,6-dimethyl-1-piperidinyl, 3,3-dimethyl-4-morpholinyl, 4-isopropyl-2,2,6,6-tetramethyl-1-piperazinyl, 4-acetyl-1-piperazinyl, and 4-ethoxycarbonyl-1-piperazinyl.

The heteroaromatic radicals furyl, thienyl, pyrrolyl, imidazolyl and pyridyl representing $R^1$ can be bonded via any of the carbon atoms, thus the radicals 2-furyl, 3-furyl, 2-thienyl, 3-thienyl, 2-pyrrolyl, 3-pyrrolyl, 2-imidazolyl, 4-imidazolyl, 5-imidazolyl, 2-pyridyl, 3-pyridyl and 4-pyridyl can be present. The phenyl radical representing $R^1$ and the heteroaromatic radicals can also be benzo-fused, $R^1$ can thus also be naphthyl, benzo[b]furyl (=benzofuryl), benzo[c]furyl, benzo[b]thienyl (=benzothienyl), benzo[c]thienyl, indolyl, benzimidazolyl, quinolyl and isoquinolyl, in particular naphthyl, benzofuryl, benzothienyl, indolyl, benzimidazolyl, quinolyl and isoquinolyl. The benzo-fused radicals representing $R^1$ are preferably bonded via a carbon atom in the heterocyclic ring, where they can be bonded in turn via each of these carbon atoms. Examples of such benzo-fused radicals representing $R^1$ are 1-naphthyl, 2-naphthyl, 2-benzofuryl, 3-benzofuryl, 2-benzothienyl, 3-benzothienyl, 2-indolyl, 3-indolyl, 4-indolyl, 5-indolyl, 6-indolyl, 7-indolyl, 2-benzimidazolyl, 2-quinolyl, 3-quinolyl, 4-quinolyl, 1-isoquinolyl, 3-isoquinolyl or 4-isoquinolyl.

The radicals representing $R^1$ can be unsubstituted or can be substituted in any desired positions by one or more, for example one, two, three or four, identical or different substituents. The above explanations, for example with respect to the substituent positions in phenyl radicals and heterocyclic radicals, correspondingly also apply to the radicals representing $R^1$. Suitable substituents on carbon atoms are thus, for example, $(C_1-C_8)$-alkyl, in particular $(C_1-C_4)$-alkyl, $(C_1-C_8)$-alkoxy, in particular $(C_1-C_4)$-alkoxy, halogen, nitro, amino, trifluoromethyl, hydroxyl, hydroxy-$(C_1-C_4)$-alkyl such as hydroxymethyl or 1-hydroxyethyl or 2-hydroxyethyl, methylenedioxy, ethylenedioxy, cyano, formyl, acetyl, hydroxycarbonyl, aminocarbonyl, $(C_1-C_4)$-alkoxycarbonyl, phenyl, phenoxy, benzyl, benzyloxy and tetrazolyl, where these substituents can be on carbon atoms in the heterocyclic ring and/or on carbon atoms in a fused benzene ring. Nitrogen atoms in pyrrolyl radicals, imidazolyl radicals and their benzo-fused analogs can be unsubstituted or, in particular, can be substituted, for example, by $(C_1-C_8)$-alkyl, for example $(C_1-C_4)$-alkyl such as methyl or ethyl, by optionally substituted phenyl or phenyl-$(C_1-C_4)$-alkyl, for example benzyl, or, for example, by $(C_1-C_4)$-alkyl-CO.

The substituent on a substituted alkylene radical representing B can on the one hand contain a cycle when it is a substituent selected from the group consisting of $(C_3-C_{10})$-cycloalkyl, $(C_3-C_{10})$-cycloalkyl-$(C_1-C_6)$-alkyl, optionally substituted $(C_6-C_{14})$-aryl, $(C_6-C_{14})$-aryl-$(C_1-C_6)$-alkyl optionally substituted in the aryl radical, optionally substituted heteroaryl and heteroaryl-$(C_1-C_6)$ optionally substituted in the heteroaryl radical, and on the other hand it can be acyclic if it is a substituent from the group consisting of $(C_1-C_8)$-alkyl, $(C_2-C_8)$-alkenyl and $(C_2-C_8)$-alkynyl. The acyclic substituents can contain 2, 3, 4, 5, 6, 7 or 8 carbon atoms or, in the case of the saturated alkyl radical, also 1 carbon atom. In the case of the alkenyl radicals and alkynyl radicals, the double bond or triple bond can be located in any desired position and in the case of the double bond can have the cis configuration or trans configuration. As explained above, these alkyl radicals, alkenyl radicals, and alkynyl radicals can be straight-chain or branched.

Examples of substituents on the $(C_1-C_6)$-alkylene radical representing B are methyl, ethyl, n-propyl, n-butyl, n-pentyl, n-hexyl, n-heptyl, n-octyl, isopropyl, isobutyl, isopentyl, isohexyl, sec-butyl, tert-butyl, tert-pentyl, neopentyl, neohexyl, 3-methylpentyl, 2-ethylbutyl, vinyl, allyl, 1-propenyl, 2-butenyl, 3-butenyl, 3-methyl-2-butenyl, ethynyl, 1-propynyl, 2-propynyl, 6-hexynyl, phenyl, benzyl, 1-phenylethyl, 2-phenylethyl, 3-phenylpropyl, 4-biphenylylmethyl, cyclopropyl, cyclopropylmethyl, cyclopentyl, cyclohexyl, cyclohexylmethyl, 2-cyclohexylethyl, 3-cyclooctylpropyl, 2-pyridyl, 3-pyridyl, 4-pyridyl, 4-pyridylmethyl, 2-(4-pyridyl)ethyl, 2-furylmethyl, 2-thienylmethyl, 3-thienylmethyl or 2-(3-indolyl)ethyl.

Halogen is fluorine, chlorine, bromine or iodine, in particular fluorine or chlorine.

The radical of an amino acid, imino acid or azaamino acid or of a dipeptide is obtained from the corresponding amino acid, imino acid or azaamino acid or the dipeptide as customary in peptide chemistry by formally removing a hydrogen atom from the N-terminal amino group or from the imino group. By means of the free bond on the amino group or the imino group thus formed this group is then linked in peptide fashion through an amide bond to the CO group in the group $R^6$—CO.

The natural and unnatural amino acids can be present in all stereochemical forms, for example in the D form, the L form or in the form of a mixture of stereoisomers, for example in the form of a racemate. Preferred amino acids are α-amino acids and β-amino acids; α-amino acids are particularly preferred. Suitable amino acids which may be mentioned, for example, are (cf. Houben-Weyl, Methoden der organischen Chemie [Methods of Organic Chemistry], Volume 15/1 and 15/2, Georg Thieme Verlag, Stuttgart, 1974):

Aad, Abu, γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hphe, hPro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val, tert-butylglycine (Tbg), -neopentylglycine (Npg), cyclohexylglycine (Chg), cyclohexylalanine (Cha), 2-thienylalanine (Thia), 2,2-diphenylaminoacetic acid, 2-(p-tolyl)-2-phenylaminoacetic acid, and 2-(p-chlorophenyl)-aminoacetic acid.

If $R^6$ is the radical of a natural or unnatural α-amino acid which is not branched on the α-carbon atom, i.e., which carries a hydrogen atom on the α-carbon atom, then the radical —N($R^b$)—CH(SC)—CO—L is present in which CO—L is the acid group of the amino acid or a derivative thereof, for example an ester group or an amide group, $R^b$ is for example hydrogen and SC is the side chain of the α-amino acid, i.e., for example, one of the substituents which are contained in the α-position of the above-mentioned α-amino acids which are unbranched in the α-position. Examples of side chains are alkyl radicals, for example the methyl group in alanine or the isopropyl group in valine, the benzyl radical in phenylalanine, the phenyl radical in phenylglycine, the 4-aminobutyl radical in lysine or the hydroxy-carbonyl methyl group in aspartic acid. Apart from arrangement by chemical structure, such side chains, and thus the amino acids, can also be arranged in groups within the meaning of the present invention on the basis of their physicochemical properties, for example lipophilic side chains can be differentiated from hydrophilic side chains which contain polar groups. Examples of lipophilic side chains which can be contained in amino acids representing $R^6$ are alkyl radicals, arylalkyl radicals or aryl radicals.

Azaamino acids are natural or unnatural amino acids in which a CH unit is replaced by a nitrogen atom. For example, in α-amino acids the central structural unit

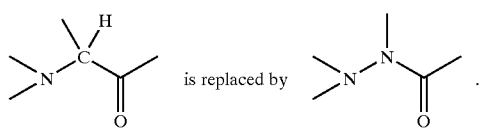

Suitable radicals of imino acids are, in particular, radicals of heterocycles selected from the following group: pyrrolidine-2-carboxylic acid; piperidine-2-carboxylic acid; 1,2,3,4-tetrahydroisoquinoline-3-carboxylic acid; decahydroisoquinoline-3-carboxylic acid; octahydroindole-2-carboxylic acid; decahydroquinoline-2-carboxylic acid; octahydrocyclopenta[b]pyrrole-2-carboxylic acid; 2-azabicyclo[2.2.2]octane-3-carboxylic acid; 2-azabicyclo[2.2.1]heptane-3-carboxylic acid; 2-azabicyclo[3.1.0] hexane-3-carboxylic acid; 2-azaspiro[4.4]nonane-3-carboxylic acid; 2-azaspiro[4.5]decane-3-carboxylic acid; spiro(bicyclo[2.2.1]heptane)-2,3-pyrrolidine-5-carboxylic acid; spiro(bicyclo[2.2.2]octane)-2,3-pyrrolidine-5-carboxylic acid; 2-azatricyclo[4.3.0.1$^{6,9}$]decane-3-carboxylic acid; decahydrocyclohepta[b]pyrrole-2-carboxylic acid; decahydrocycloocta[c]pyrrole-2-carboxylic acid; octahydrocyclopenta[c]pyrrole-2-carboxylic acid; octahydroisoindole-1-carboxylic acid; 2,3,3a,4,6a-hexahydrocyclopenta[b]pyrrole-2-carboxylic acid; 2,3,3a,4,5,7a-hexahydroindole-2-carboxylic acid; tetrahydrothiazole-4-carboxylic acid; isoxazolidine-3-carboxylic acid; pyrazolidine-3-carboxylic acid, and hydroxypyrrolidine-2-carboxylic acid, all of which can optionally be substituted (see following formulae):

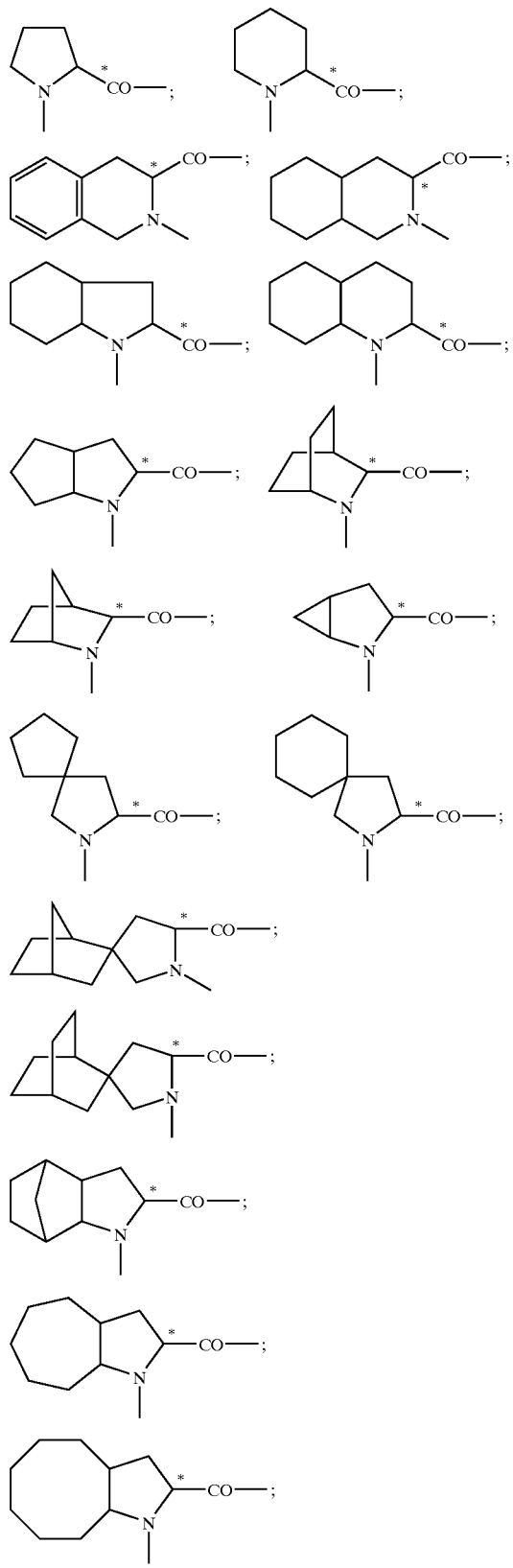

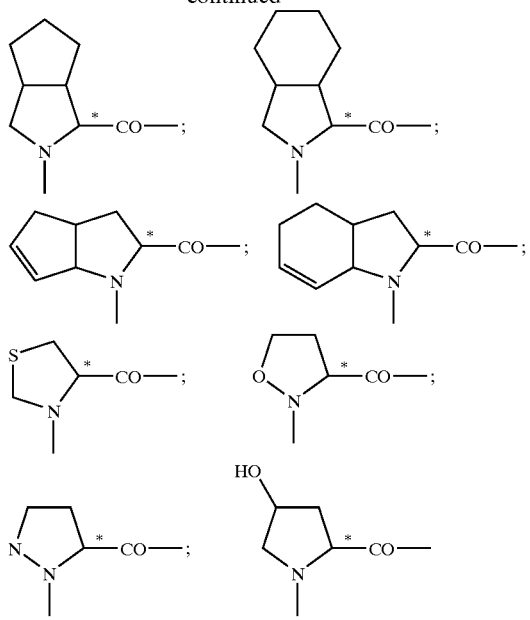

The heterocycles on which the radicals mentioned above are based are disclosed, for example, in U.S. Pat. Nos. 4,344,949; 4,374,847; 4,350,704; EP-A 29,486; EP-A 31,741; EP-A 46,953; EP-A 49,605; EP-A 49,658; EP-A 50,800; EP-A 51,020; EP-A 52,870; EP-A 79,022; EP-A 84,164; EP-A 89,637; EP-A 90,341; EP-A 90,362; EP-A 105,102; EP-A 109,020; EP-A 111,873; EP-A 271,865; and EP-A 344,682

Dipeptides can contain natural or unnatural amino acids, imino acids and azaamino acids as structural units. In addition, the natural or unnatural amino acids, imino acids, azaamino acids and dipeptides can also be present in the form of derivatives of the carboxylic acid group, for example as esters or amides, such as, for example, as methyl esters, ethyl esters, n-propyl esters, isopropyl esters, isobutyl esters, tert-butyl esters, benzyl esters, unsubstituted amides, methylamides, ethylamides, semicarbazides or ω-amino-($C_2$–$C_8$)-alkylamides.

Functional groups in radicals of amino acids, imino acids, azaamino acids and dipeptides as well as in other parts of the molecules of the formula I can be present in protected form. Suitable protective groups such as, for example, urethane protective groups, carboxyl protective groups and side chain protective groups are described in Hubbuch, Kontakte (Merck) 1979, No. 3, pages 14 to 23, and in Büllesbach, Kontakte (Merck) 1980, No. 1, pages 23 to 35. The following may be mentioned in particular: Aloc, Pyoc, Fmoc, Tcboc, Z, Boc, Ddz, Bpoc, Adoc, Msc, Moc, Z($NO_2$), Z($Hal_n$), Bobz, Iboc, Adpoc, Mboc, Acm, tert-butyl, OBzl, ONbzl, OMbzl, Bzl, Mob, Pic, Trt.

Physiologically tolerable salts of the compounds of the formula I are in particular pharmaceutically utilizable or nontoxic salts. In the case of compounds of the formula I which contain acidic groups, for example carboxylic acid groups, such salts are, for example, alkali metal salts or alkaline earth metal salts as well as salts with ammonia and physiologically tolerable organic amines. Such compounds of the formula I can thus be present, for example, as sodium salts, potassium salts, calcium salts, magnesium salts or as acid addition salts with amines such as, for example, triethylamine, ethanolamine, tris(2-hydroxyethyl)amine or amino acids, in particular basic amino acids.

Compounds of the formula I which contain basic groups, for example an amino group or a guanidino group, form salts with inorganic acids, such as, for example, hydrochloric acid, sulfuric acid or phosphoric acid, and with organic carboxylic acids or sulfonic acids, such as, for example, acetic acid, citric acid, benzoic acid, maleic acid, fumaric acid, tartaric acid, methanesulfonic acid or p-toluenesulfonic acid. If the compounds of the formula I simultaneously contain acidic and basic groups in the molecule, the invention also includes internal salts or betaines in addition to the salt forms described.

Salts can be obtained from the compounds of the formula I according to customary procedures known to the person skilled in the art, for example by combining with an organic or inorganic acid or base in a solvent or dispersant, or alternatively from other salts by anion exchange or cation exchange. The present invention also includes all salts of the compounds of the formula I which are not directly suitable for use in pharmaceuticals because of low physiological tolerability, but are suitable, for example, as intermediates for chemical reactions or for the preparation of physiologically tolerable salts.

The compounds of the formula I can be present in stereoisomeric forms. If the compounds of the formula I contain one or more centers of asymmetry, these can independently of one another have the S configuration or the R configuration. The invention includes all possible stereoisomers, for example enantiomers and diastereomers, and mixtures of two or more stereoisomeric forms, for example mixtures of enantiomers and/or diastereomers, in all ratios. The invention thus relates to enantiomers in enantiomerically pure form, both as levorotatory and dextrorotatory antipodes, in the form of racemates and in the form of mixtures of the two enantiomers in all ratios. In the presence of cis/trans isomerism, the invention relates to both the cis form and the trans form and mixtures of these forms. Individual stereoisomers can be prepared, if desired, by separation of a mixture according to customary methods, for example by chromatography or crystallization, by use of stereochemically homogeneous starting substances in the synthesis or by stereoselective synthesis. If appropriate, derivatization can be carried out before separation of stereoisomers. A stereoisomer mixture can be separated at the stage of the compounds of the formula I or at the stage of a starting substance or of an intermediate in the course of the synthesis.

The compounds of the formula I according to the invention can moreover contain mobile hydrogen atoms, i.e., be present in various tautomeric forms. The present invention also relates to all these tautomers. The present invention furthermore includes all solvates of compounds of the formula I, for example hydrates or adducts with alcohols, as well as derivatives of the compounds of the formula I, for example esters, prodrugs and active metabolites.

The individual structural elements in the formula I preferably independently of one another have the following meanings.

W is preferably $R^1$—A—C($R^{13}$).

Z is preferably oxygen.

A is preferably a direct bond or methylene, particularly preferably a direct bond.

B is preferably a divalent radical selected from the group consisting of methylene, ethylene, trimethylene, tetramethylene, vinylene, phenylene or a substituted ($C_1$–$C_4$)-alkylene radical. Particularly preferably, B is a divalent methylene radical or ethylene radical (=1,2- ethylene), in particular a methylene radical, where each of these radicals can be unsubstituted or substituted. Very particularly preferably, B is a substituted methylene radical or ethylene radical, in particular a substituted methylene radical. If a divalent alkylene radical representing B, in particular a methylene radical or ethylene radical (=1,2-ethylene), is substituted, it is preferably substituted by a radical selected from the group consisting of $(C_1–C_8)$-alkyl, $(C_2–C_8)$-alkenyl, $(C_2–C_8)$-alkynyl, $(C_3–C_7)$-cycloalkyl, in particular $(C_5–C_6)$-cycloalkyl, $(C_3–C_7)$-cycloalkyl-$(C_1–C_4)$-alkyl, in particular $(C_5–C_6)$-cycloalkyl-$(C_1–C_4)$-alkyl, optionally substituted $(C_6–C_{10})$-aryl, $(C_6–C_{10})$-aryl-$(C_1–C_4)$-alkyl optionally substituted in the aryl radical, optionally substituted heteroaryl and heteroaryl-$(C_1–C_4)$-alkyl optionally substituted in the heteroaryl radical. Particularly preferably, a substituted alkylene radical representing B is substituted by $(C_1–C_8)$-alkyl, i.e., by a straight-chain or branched alkyl radical having 1, 2, 3, 4, 5, 6, 7 or 8 carbon atoms.

E is preferably tetrazolyl or $R^{10}CO$, particularly preferably $R^{10}CO$.

R is preferably hydrogen, $(C_1–C_8)$-alkyl or benzyl, particularly preferably hydrogen or $(C_1–C_8)$-alkyl, very particularly preferably hydrogen or $(C_1–C_4)$-alkyl, in particular hydrogen, methyl or ethyl.

$R^0$ is preferably $(C_1–C_8)$-alkyl, $(C_3–C_{12})$-cycloalkyl, $(C_3–C_{12})$-cycloalkyl-$(C_1–C_8)$-alkyl, $(C_6–C_{12})$-bicycloalkyl, $(C_6–C_{12})$-bicycloalkyl-$(C_1–C_8)$-alkyl, $(C_6–C_{12})$-tricycloalkyl, $(C_6–C_{12})$-tricycloalkyl-$(C_1–C_8)$-alkyl, optionally substituted $(C_6–C_{14})$-aryl, $(C_6–C_{14})$-aryl-$(C_1–C_8)$-alkyl optionally substituted in the aryl radical, optionally substituted heteroaryl or heteroaryl-$(C_1–C_8)$-alkyl optionally substituted in the heteroaryl radical, particularly preferably $(C_1–C_8)$-alkyl, $(C_3–C_{12})$-cycloalkyl, $(C_3–C_{12})$-cycloalkyl-$(C_1–C_4)$-alkyl, optionally substituted $(C_6–C_{14})$-aryl, $(C_6–C_{14})$-aryl-$(C_1–C_4)$-alkyl optionally substituted in the aryl radical, optionally substituted heteroaryl or heteroaryl-$(C_1–C_4)$-alkyl optionally substituted in the heteroaryl radical, very particularly preferably optionally substituted $(C_6–C_{14})$-aryl, $(C_6–C_{14})$-aryl-$(C_1–C_4)$-alkyl optionally substituted in the aryl radical, optionally substituted heteroaryl or heteroaryl-$(C_1–C_4)$-alkyl optionally substituted in the heteroaryl radical, moreover preferably $(C_6–C_{14})$-aryl-$(C_1–C_4)$-alkyl optionally substituted in the aryl radical or heteroaryl-$(C_1–C_4)$-alkyl substituted in the heteroaryl radical. It is especially preferred if $R^0$ is $(C_6–C_{14})$-aryl-$(C_1–C_4)$-alkyl optionally substituted in the aryl radical, in particular biphenylylmethyl, naphthylmethyl or benzyl which is unsubstituted or monosubstituted or polysubstituted in the aryl radical.

$R^1$ is preferably a radical selected from the group consisting of phenyl, furyl, thienyl, pyrrolyl, imidazolyl and pyridyl, which is not benzo-fused. Particularly preferably, $R^1$ is a phenyl radical, a 2-furyl radical, a 3-furyl radical, a 2-thienyl radical, a 3-thienyl radical, a 3-pyrrolyl radical, a 4-imidazolyl radical, a 3-pyridyl radical or a 4-pyridyl radical, very particularly preferably a phenyl radical, a 2-furyl radical, a 3-furyl radical, a 2-thienyl radical, a 3-thienyl radical, a 4-imidazolyl radical or a 4-pyridyl radical, moreover preferably a phenyl radical or a 4-pyridyl radical. Preferably, a radical representing $R^1$ is unsubstituted or substituted by one, two or three, in particular by one or by two, identical or different radicals of the type which are indicated above as suitable substituents on carbon atoms and nitrogen atoms in $R^1$. Particularly preferably, a radical representing $R^1$ is unsubstituted. Preferred substituents on carbon atoms in the radical $R^1$ are $(C_1–C_4)$-alkyl, $(C_1–C_4)$-alkoxy, halogen, amino, trifluoromethyl, hydroxyl, hydroxy-$(C_1–C_4)$-alkyl, methylenedioxy, ethylenedioxy, phenyl, phenoxy, benzyl and benzyloxy, in particular as substituents on carbon atoms of a heteroaryl radical representing $R^1$. Particularly preferred substituents on carbon atoms in $R^1$, in particular on carbon atoms of a phenyl radical representing $R^1$, are $(C_1–C_4)$-alkyl, $(C_1–C_4)$-alkoxy, halogen, trifluoromethyl, hydroxyl, hydroxy-$(C_1–C_4)$-alkyl, methylenedioxy, ethylenedioxy, phenyl, phenoxy, benzyl and benzyloxy.

$R^2$ is preferably hydrogen or $(C_1–C_8)$-alkyl, particularly preferably hydrogen or $(C_1–C_4)$-alkyl.

$R^3$ is preferably $(C_1–C_8)$-alkyl, optionally substituted $(C_6–C_{14})$-aryl, $(C_6–C_{14})$-aryl-$(C_1–C_4)$-alkyl optionally substituted in the aryl radical, $(C_3–C_8)$-cycloalkyl, $(C_3–C_8)$-cycloalkyl-$(C_1–C_4)$-alkyl, $(C_6–C_{12})$-bicycloalkyl, $(C_6–C_{12})$-bicycloalkyl-$(C_1–C_4)$-alkyl, $(C_6–C_{12})$-tricycloalkyl, $(C_6–C_{12})$-tricycloalkyl-$(C_1–C_4)$-alkyl, $(C_2–C_8)$-alkenyl, $(C_2–C_8)$-alkynyl, optionally substituted heteroaryl, heteroaryl-$(C_1–C_4)$-alkyl optionally substituted in the heteroaryl radical, $R^{11}NH$, $CON(CH_3)R^4$, $CONHR^4$, $CON(CH_3)R^{15}$ or $CONHR^{15}$, particularly preferably optionally substituted $(C_6–C_{14})$-aryl, in particular optionally substituted $(C_6–C_{10})$-aryl, optionally substituted 5-membered or 6-membered heteroaryl having one or two identical or different heteroatoms selected from the group consisting of nitrogen, oxygen and sulfur, in particular pyridyl, $R^{11}NH$, $CON(CH_3)R^4$, $CONHR^4$, $CON(CH_3)R^{15}$ or $CONHR^{15}$, very particularly preferably optionally substituted $(C_6–C_{10})$-aryl, $R^{11}NH$, $CON(CH_3)R^4$, $CONHR^4$, $CON(CH_3)R^{15}$ or $CONHR^{15}$.

$R^4$ is preferably $(C_1–C_8)$-alkyl which can optionally be substituted as indicated above in the definition of $R^4$, particularly preferably $(C_1–C_8)$-alkyl, in particular $(C_1–C_6)$-alkyl, which is substituted by one or two of the substituents indicated in the above definition of $R^4$. It is very particularly preferred if one of the substituents is bonded in the 1-position of the alkyl group, i.e., to that carbon atom of the alkyl group to which the nitrogen atom in the group $CONHR^4$ or in the group $CON(CH_3)R^4$ is also bonded, and if this substituent in the 1-position is one of the radicals hydroxycarbonyl, aminocarbonyl, mono- or di-$((C_1–C_{18})$-alkyl)-aminocarbonyl, $(C_6–C_{14})$-aryl-$(C_1–C_8)$-alkoxycarbonyl which can also be substituted in the aryl radical, Het-CO, $R^6$—CO, $(C_1–C_8)$-alkoxycarbonyl or tetrazolyl. In this very particularly preferred case, the radical —$NHR^4$ or the radical —$N(CH_3)R^4$ is thus the radical of an α-amino acid or of an N-methyl-α-amino acid or of a derivative thereof, where this radical is formally obtained by abstraction of a hydrogen atom from the amino group of the amino acid. Especially preferred α-amino acids are in this case those having a lipophilic side chain, for example phenylglycine, phenylalanine, valine, leucine, isoleucine and homologs thereof, as well as derivatives of these amino acids such as esters, amides or the derivatives in which the carboxylic acid group is converted into the radical Het-CO.

$R^{11}$ is preferably hydrogen, $R^{12a}$, $R^{12a}$—CO, H—CO, $R^{12a}$—O—CO, $R^{12b}$—CO, $R^{12b}$—CS or $R^{12a}$—S(O)$_2$, particularly preferably hydrogen, $R^{12a}$, $R^{12a}$—CO, $R^{12a}$—O—CO, $R^{12b}$—CO, $R^{12b}$—CS or $R^{12a}$—S(O)$_2$, very particularly preferably $R^{12a}$, $R^{12a}$—CO, $R^{12a}$—O—CO, $R^{12b}$—CO, $R^{12b}$—CS or $R^{12a}$—S(O)$_2$, moreover preferably $R^{12a}$, $R^{12a}$—CO, $R^{12a}$—O—CO, $R^{12b}$—CO or $R^{12a}$—S(O)$_2$.

$R^{12a}$ is preferably $(C_1–C_{10})$-alkyl, $(C_2–C_8)$-alkenyl, $(C_2–C_8)$-alkynyl, $(C_3–C_{12})$-cycloalkyl, $(C_3–C_{12})$-cycloalkyl-$(C_1–C_8)$-alkyl, optionally substituted $(C_6–C_{14})$- aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical, or the radical $R^{15}$.

$R^{12b}$ is preferably $R^{12a}$—NH.

$R^{13}$ is preferably hydrogen, $(C_1-C_6)$-alkyl, $(C_3-C_8)$-cycloalkyl or benzyl, particularly preferably hydrogen or $(C_1-C_6)$-alkyl, very particularly preferably hydrogen or $(C_1-C_4)$-alkyl, in particular $(C_1-C_4)$-alkyl, where a preferred alkyl radical representing $R^{13}$ is the methyl radical.

$R^{15}$ is preferably $R^{16}$—$(C_1-C_3)$-alkyl or $R^{16}$, particularly preferably $R^{16}$—$(C_1)$-alkyl or $R^{16}$. Additionally preferably, $R^{15}$, if $R^3$ is $COOR^{15}$, is the exo-2-norbornyl radical, the endo-2-norbornyl radical or the bicyclo[3.2.1]octyl radical, and $R^{15}$, if $R^3$ is $CONHR^{15}$, is the exo-2-norbornyl radical, the endo-2-norbornyl radical, the 3-noradamantyl radical and in particular the 1-adamantyl radical, the 2-adamantyl radical, the 1-adamantylmethyl radical or the 2-adamantylmethyl radical.

$R^{16}$ is preferably a 6-membered to 14-membered, in particular 7-membered to 12-membered, bridged bicyclic or tricyclic radical which is saturated or partially unsaturated and which can also contain one to four, in particular one, two or three, especially one or two, identical or different heteroatoms selected from the group consisting of nitrogen, oxygen and sulfur and which can also be substituted by one or more identical or different substituents selected from the group consisting of $(C_1-C_4)$-alkyl and oxo.

Het is preferably the radical of a 5-membered to 10-membered, saturated monocyclic or polycyclic heterocycle bonded via a ring nitrogen atom, which can contain one or two identical or different additional ring heteroatoms selected from the group consisting of oxygen, nitrogen and sulfur and can be optionally substituted on carbon atoms and on ring nitrogen atoms, where substituents on additional ring nitrogen atoms can be identical or different radicals selected from the group consisting of hydrogen, $R^h$, HCO, $R^hCO$ or $R^hO$—CO. Particularly preferably, Het is a heterocycle of this type which contains no additional ring heteroatom or which contains one additional ring heteroatom selected from the group consisting of nitrogen, oxygen and sulfur, very particularly preferably Het is the radical of a 5-membered, 6-membered or 7-membered, saturated monocyclic heterocycle bonded via a nitrogen atom, which contains no additional ring heteroatom or which contains one additional ring heteroatom from the group consisting of nitrogen, oxygen and sulfur, where also in these cases the radical Het can be unsubstituted or can be substituted on carbon atoms and/or on additional ring nitrogen atoms.

If $R^3$ is one of the radicals $(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical, $(C_3-C_8)$-cycloalkyl, $(C_3-C_8)$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, $(C_2-C_8)$-alkenyl, $(C_2-C_8)$-alkynyl, $CON(CH_3)R^4$, $CONHR^4$, $COOR^{15}$, $CON(CH_3)R^{15}$ or $CONHR^{15}$, e is preferably 0 and h is preferably 1. If $R^3$ is $R^{11}NH$, e is preferably 1 and h is preferably 0.

Preferred compounds of the formula I are those compounds in which one or more of the radicals have preferred meanings, all combinations of preferred substituent meanings being a subject of the present invention. Particularly preferred compounds of the formula I are those in which, simultaneously W is $R^1$—A—$C(R^{13})$;

Z is oxygen or sulfur;

A is a direct bond or methylene;

B is a divalent methylene radical or ethylene radical, both of which can be unsubstituted or can be substituted by a radical selected from the group consisting of $(C_1-C_8)$-alkyl, $(C_2-C_8)$-alkenyl, $(C_2-C_8)$-alkynyl, $(C_3-C_{10})$-cycloalkyl, $(C_3-C_{10})$-cycloalkyl-$(C_1-C_6)$-alkyl, optionally substituted $(C_6-C_{14})$-aryl, $(C_1-C_{14})$-aryl-$(C_1-C_6)$-alkyl optionally substituted in the aryl radical, optionally substituted heteroaryl and heteroaryl-$(C_1-C_6)$-alkyl optionally substituted in the heteroaryl radical;

E is tetrazolyl or $R^{10}CO$;

R is hydrogen or $(C_1-C_8)$-alkyl;

$R^0$ is hydrogen, $(C_1-C_8)$-alkyl, $(C_3-C_{12})$-cycloalkyl, $(C_3-C_{12})$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical, H—CO, $(C_1-C_8)$-alkyl-CO, $(C_3-C_{12})$-cycloalkyl-CO, $(C_3-C_{12})$-cycloalkyl-$(C_1-C_8)$-alkyl-CO, $(C_6-C_{12})$-bicycloalkyl-CO, $(C_6-C_{12})$-bicycloalkyl-$(C_1-C_8)$-alkyl-CO, $(C_6-C_{12})$-tricycloalkyl-CO, $(C_6-C_{12})$-tricycloalkyl-$(C_1-C_8)$-alkyl-CO, optionally substituted $(C_6-C_{14})$-aryl-CO, $(C_6-C_{14})$-aryl-$(C_1-C_8)$-alkyl-CO optionally substituted in the aryl radical, optionally substituted heteroaryl-CO, heteroaryl-$(C_1-C_8)$-alkyl-CO optionally substituted in the heteroaryl radical, $(C_1-C_8)$-alkyl-$S(O)_n$, $(C_3-C_{12})$-cycloalkyl-$S(O)_n$, $(C_3-C_{12})$-cycloalkyl-$(C_1-C_8)$-alkyl-$S(O)_n$, $(C_6-C_{12})$-bicycloalkyl-$S(O)_n$, $(C_6-C_{12})$-tricycloalkyl-$(C_1-C_8)$-alkyl-$S(O)_n$, optionally substituted $(C_6-C_{14})$-aryl-$S(O)_n$, $(C_6-C_{14})$-aryl-$(C_1-C_8)$-alkyl-S(O), optionally substituted in the aryl radical, optionally substituted heteroaryl-$S(O)_n$ or heteroaryl-$(C_1-C_8)$-alkyl-$S(O)_n$ optionally substituted in the heteroaryl radical, where n is 1 or 2;

$R^1$ is an optionally substituted radical selected from the group of phenyl, furyl, thienyl, pyrrolyl, imidazolyl and pyridyl, where each of these radicals can also be benzo-fused;

$R^2$ is hydrogen or $(C_1-C_8)$-alkyl;

$R^3$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical, $(C_3-C_8)$-cycloalkyl, $(C_3-C_8)$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, $(C_2-C_8)$-alkenyl, $(C_2-C_8)$-alkynyl, $R^{11}NH$, $CON(CH_3)R^4$, $CONHR^4$, $COOR^{15}$, $CON(CH_3)R^{15}$ or $CONHR^{15}$;

$R^4$ is $(C_1-C_8)$-alkyl which can optionally be monosubstituted or polysubstituted by identical or different radicals selected from the group consisting of hydroxyl, $(C_1-C_8)$-alkoxy, $R^5$, optionally substituted $(C_3-C_8)$-cycloalkyl, hydroxycarbonyl, aminocarbonyl, mono- or di-$((C_1-C_{18})$-alkyl)-aminocarbonyl, $(C_6-C_{14})$-aryl-$(C_1-C_8)$-alkoxycarbonyl, which can also be substituted in the aryl radical, $(C_1-C_8)$-alkoxycarbonyl, Het-CO, $R^6$—CO, tetrazolyl and trifluoromethyl;

$R^5$ is optionally substituted $(C_6-C_{14})$-aryl, $(C_6-C_{14})$-aryl-$(C_1-C_8)$-alkyl optionally substituted in the aryl radical or an optionally substituted monocyclic or bicyclic 5-membered to 12-membered heterocyclic ring, which can be aromatic, partially hydrogenated or completely hydrogenated and which can contain one, two or three identical or different heteroatoms selected from the group consisting of nitrogen, oxygen and sulfur;

$R^6$ is the radical of a natural or unnatural amino acid, imino acid, optionally N—$(C_1-C_8)$-alkylated or N—$((C_6-C_{14})$-aryl-$(C_1-C_8)$-alkylated) azaamino acid which can also be substituted in the aryl radical, or the radical of a dipeptide, as well as their esters and amides, where free functional groups can be protected by protective groups customary in peptide chemistry;

$R^{10}$ is hydroxyl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, $(C_1-C_8)$-alkylcarbonyloxy-$(C_1-C_6)$-alkoxy, $(C_6-C_{14})$-arylcarbonyloxy-$(C_1-C_6)$-alkoxy, amino or mono- or di-$((C_1-C_{18})$-alkyl)-amino;

$R^{11}$ is hydrogen, $R^{12a}$, $R^{12a}$—CO, $R^{12a}$—O—CO, $R^{12b}$—CO, $R^{12b}$—CS or $R^{12a}$—S(O)$_2$;

$R^{12a}$ is $(C_1-C_{18})$-alkyl, $(C_2-C_8)$-alkenyl, $(C_2-C_8)$-alkynyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical, or the radical $R^{15}$;

$R^{12b}$ is amino, di-$((C_1-C_{18})$-alkyl)-amino or $R^{12a}$—NH;

$R^{13}$ is hydrogen or $(C_1-C_6)$-alkyl;

$R^{15}$ is $R^{16}$—$(C_1-C_6)$-alkyl or $R^{16}$;

$R^{16}$ is a 6-membered to 14-membered bicyclic or tricyclic radical which is saturated or partially unsaturated and which can also contain one, two, three or four identical or different heteroatoms selected from the group consisting of nitrogen, oxygen and sulfur and which can also be substituted by one or more identical or different substituents selected from the group consisting of $(C_1-C_4)$-alkyl and oxo; Het is the radical of a 5-membered to 10-membered, saturated monocyclic or polycyclic heterocycle, bonded via a ring nitrogen atom, which can contain one, two, three or four identical or different additional ring heteroatoms selected from the group of oxygen, nitrogen and sulfur and which can optionally be substituted on carbon atoms and on additional ring nitrogen atoms, where substituents on additional ring nitrogen atoms can be identical or different radicals selected from the group of hydrogen, $R^h$, HCO, $R^hCO$ or $R^hO$—CO and $R^h$ is $(C_1-C_8)$-alkyl, $(C_3-C_8)$-cycloalkyl, $(C_3-C_8)$-cycloalkyl-$(C_1-C_8)$-alkyl, optionally substituted $(C_6-C_{14})$-aryl or $(C_6-C_{14})$-aryl-$(C_1-C_8)$-alkyl optionally substituted in the aryl radical;

e and h independently of one another are 0 or 1;

in all their stereoisomeric forms and mixtures thereof in all ratios, and their physiologically tolerable salts.

Very particularly preferred compounds of the formula I are those in which, simultaneously W is $R^1$—A—$C(R^{13})$;

Z is oxygen;

A is a direct bond or methylene;

B is a divalent methylene radical or ethylene radical, both of which can be unsubstituted or can be substituted by a radical selected from the group consisting of $(C_1-C_8)$-alkyl, $(C_2-C_8)$-alkenyl, $(C_2-C_8)$-alkynyl, $(C_3-C_{10})$-cycloalkyl, $(C_3-C_{10})$-cycloalkyl-$(C_1-C_6)$-alkyl, optionally substituted $(C_6-C_{14})$-aryl, $(C_6C_{14})$-aryl-$(C_1-C_6)$-alkyl, optionally substituted in the aryl radical, optionally substituted heteroaryl and heteroaryl-$(C_1-C_6)$-alkyl optionally substituted in the heteroaryl radical;

E is $R^{10}CO$;

R is hydrogen or $(C_1-C_4)$-alkyl;

$R^0$ is $(C_1-C_8)$-alkyl, $(C_3-C_{12})$-cycloalkyl, $(C_3-C_{12})$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl or heteroaryl-$(C_1-C_8)$-alkyl optionally substituted in the heteroaryl radical;

$R^1$ is an optionally substituted radical selected from the group consisting of phenyl, furyl, thienyl, pyrrolyl, imidazolyl and pyridyl;

$R^2$ is hydrogen or $(C_1-C_4)$-alkyl;

$R^3$ is $(C_1-C_8)$-alkyl, optionally substituted $(C_6-C_{14})$-aryl, $(C_6-C_{14})$-aryl-$(C_1-C_4)$-alkyl optionally substituted in the aryl radical, optionally substituted heteroaryl, heteroaryl-$(C_1-C_4)$-alkyl optionally substituted in the heteroaryl radical, $(C_3-C_8)$-cycloalkyl, $(C_3-C_8)$-cycloalkyl-$(C_1-C_4)$-alkyl, $(C_6-C_{12})$-bicycloalkyl, $(C_6-C_{12})$-bicycloalkyl-$(C_1-C_4)$-alkyl, $(C_6-C_{12})$-tricycloalkyl, $(C_6-C_{12})$-tricycloalkyl-$(C_1-C_4)$-alkyl, $R^{11}NH$, $CON(CH_3)R^4$, $CONHR^4$, $COOR^{15}$, $CON(CH_3)R^{15}$ or $CONHR^{15}$;

$R^4$ is $(C_1-C_8)$-alkyl which can optionally be monosubstituted or polysubstituted by identical or different radicals from the group consisting of hydroxyl, $(C_1-C_8)$-alkoxy, $R^5$, optionally substituted $(C_3-C_8)$-cycloalkyl, hydroxycarbonyl, aminocarbonyl, mono- or di-$((C_1-C_8)$-alkyl)-aminocarbonyl, $(C_6-C_{14})$-aryl-$(C_1-C_8)$-alkoxycarbonyl which can also be substituted in the aryl radical, $(C_1-C_8)$-alkoxycarbonyl, Het-CO, $R^6$—CO, tetrazolyl and trifluoromethyl;

$R^5$ is optionally substituted $(C_6-C_{14})$-aryl, $(C_6-C_{14})$-aryl-$(C_1-C_8)$-alkyl optionally substituted in the aryl radical or an optionally substituted monocyclic or bicyclic 5-membered to 12-membered heterocyclic ring, which can be aromatic, partially hydrogenated or completely hydrogenated and which can contain one, two or three identical or different heteroatoms selected from the group consisting of nitrogen, oxygen and sulfur;

$R^6$ is the radical of a natural or unnatural amino acid, imino acid or optionally N—$(C_1-C_8)$-alkylated or N—$((C_6-C_{14})$-aryl-$(C_1-C_8)$-alkylated) azaamino acid which can also be substituted in the aryl radical, as well as their esters and amides, where free functional groups can be protected by protective groups customary in peptide chemistry;

$R^{10}$ is hydroxyl, $(C_1-C_8)$-alkoxy, $(C_6-C_{14})$-aryl-$(C_1-C_8)$-alkoxy which can also be substituted in the aryl radical, optionally substituted $(C_6-C_{14})$-aryloxy, $(C_1-C_8)$-alkylcarbonyloxy-$(C_1-C_6)$-alkoxy, $(C_6-C_{14})$-arylcarbonyloxy-$(C_1-C_6)$-alkoxy, amino or mono- or di-$((C_1-C_8)$-alkyl)-amino;

$R^{11}$ is $R^{12a}$, $R^{12a}$—CO, $R^{12a}$—O—CO, $R^{12b}$—CO or $R^{12a}$—S(O)$_2$;

$R^{12a}$ is (C$_1$–C$_{10}$)-alkyl, (C$_2$–C$_8$)-alkenyl, (C$_2$–C$_8$)-alkynyl, (C$_3$–C$_{12}$)-cycloalkyl, (C$_3$–C$_{12}$)-cycloalkyl-(C$_1$–C$_8$)-alkyl, optionally substituted (C$_6$–C$_{14}$)-aryl, (C$_6$–C$_{14}$)-aryl-(C$_1$–C$_8$)-alkyl optionally substituted in the aryl radical, optionally substituted heteroaryl, heteroaryl-(C$_1$–C$_8$)-alkyl optionally substituted in the heteroaryl radical, or the radical $R^{15}$;

$R^{12b}$ is amino, di-((C$_1$–C$_{10}$)-alkyl)-amino or $R^{12a}$—NH;

$R^{13}$ is hydrogen or (C$_1$–C$_4$)-alkyl;

$R^{15}$ is $R^{16}$—(C$_1$–C$_3$)-alkyl or $R^{16}$;

$R^{16}$ is a 7-membered to 12-membered bicyclic or tricyclic radical which is saturated or partially unsaturated and which can also contain one or two identical or different heteroatoms selected from the group consisting of nitrogen, oxygen and sulfur and which can also be substituted by one or more identical or different substituents selected from the group consisting of (C$_1$–C$_4$)-alkyl and oxo;

Het is the radical of a 5-membered to 10-membered, saturated monocyclic or polycyclic heterocycle bonded via a ring nitrogen atom, which can contain one or two identical or different additional ring heteroatoms selected from the group consisting of oxygen, nitrogen and sulfur and which can optionally be substituted on carbon atoms and additional ring nitrogen atoms, where substituents on additional ring nitrogen atoms can be identical or different radicals selected from the group consisting of hydrogen, $R^h$, HCO, $R^h$CO or $R^h$O—CO and $R^h$ is (C$_1$–C$_6$)-alkyl, (C$_3$–C$_8$)-cycloalkyl, (C$_3$–C$_8$)-cycloalkyl-(C$_1$–C$_4$)-alkyl, optionally substituted (C$_6$–C$_{14}$)-aryl or (C$_6$–C$_{14}$)-aryl-(C$_1$–C$_4$)-alkyl optionally substituted in the aryl radical;

e and h independently of one another are 0 or 1;

in all their stereoisomeric forms and mixtures thereof in all ratios, and their physiologically tolerable salts.

Additionally preferred compounds of the formula I are those in which, simultaneously W is $R^1$—A—C($R^{13}$);

Z is oxygen;

A is a direct bond or methylene;

B is an unsubstituted methylene radical or a methylene radical which is substituted by a radical selected from the group consisting of (C$_1$–C$_8$)-alkyl, (C$_2$–C$_8$)-alkenyl, (C$_2$–C$_8$)-alkynyl, (C$_3$–C$_7$)-cycloalkyl, (C$_3$–C$_7$)-cycloalkyl-(C$_1$–C$_4$)-alkyl, optionally substituted (C$_6$–C$_{10}$)-aryl, (C$_6$–C$_{10}$)-aryl-(C$_1$–C$_4$)-alkyl optionally substituted in the aryl radical, optionally substituted heteroaryl and heteroaryl-(C$_1$–C$_4$)-alkyl optionally substituted in the heteroaryl radical;

E is $R^{10}$CO;

R is hydrogen or (C$_1$–C$_4$)-alkyl;

$R^0$ is (C$_6$–C$_{14}$)-aryl-(C$_1$–C$_4$)-alkyl optionally substituted in the aryl radical or heteroaryl-(C$_1$–C$_4$)-alkyl optionally substituted in the heteroaryl radical;

$R^1$ is an optionally substituted radical selected from the group consisting of phenyl, furyl, thienyl, pyrrolyl, imidazolyl and pyridyl;

$R^2$ is hydrogen or (C$_1$–C$_4$)-alkyl;

$R^3$ is an unsubstituted phenyl radical or naphthyl radical or a phenyl radical or naphthyl radical which is substituted by one, two or three identical or different radicals selected from the group consisting of (C$_1$–C$_4$)-alkyl, (C$_1$–C$_4$)-alkoxy, hydroxyl, halogen, trifluoromethyl, nitro, methylenedioxy, ethylenedioxy, hydroxycarbonyl, (C$_1$–C$_4$)-alkoxycarbonyl, aminocarbonyl, cyano, phenyl, phenoxy, benzyl and benzyloxy, or $R^3$ is pyridyl, (C$_1$–C$_4$)-alkyl, (C$_2$–C$_4$)-alkenyl, (C$_2$–C$_4$)-alkynyl, (C$_5$–C$_6$)-cycloalkyl, $R^{11}$NH, CON(CH$_3$)$R^4$, CONH$R^4$, CON(CH$_3$)$R^{15}$ or CONH$R^{15}$;

$R^4$ is (C$_1$–C$_8$)-alkyl which is substituted by one or two identical or different radicals selected from the group consisting of hydroxyl, (C$_1$–C$_8$)-alkoxy, $R^5$, optionally substituted (C$_3$–C$_8$)-cycloalkyl, hydroxycarbonyl, aminocarbonyl, (C$_6$–C$_{10}$)-aryl-(C$_1$–C$_4$)-alkoxycarbonyl which can also be substituted in the aryl radical, (C$_1$–C$_6$)-alkoxycarbonyl, Het-CO, $R^6$—CO, tetrazolyl and trifluoromethyl;

$R^5$ is optionally substituted (C$_6$–C$_{10}$)-aryl, (C$_6$–C$_{10}$)-aryl-(C$_1$–C$_4$)-alkyl optionally substituted in the aryl radical or an optionally substituted monocyclic or bicyclic 5-membered to 10-membered heterocyclic ring which can be aromatic, partially hydrogenated or completely hydrogenated and which can contain one, two or three identical or different heteroatoms selected from the group consisting of nitrogen, oxygen and sulfur;

$R^{10}$ is hydroxyl, (C$_1$–C$_8$)-alkoxy, (C$_6$–C$_{10}$)-aryl-(C$_1$–C$_4$)-alkoxy which can also be substituted in the aryl radical, optionally substituted (C$_6$–C$_{10}$)-aryloxy, (C$_1$–C$_8$)-alkylcarbonyloxy-(C$_1$–C$_4$)-alkoxy, (C$_6$–C$_{10}$)-arylcarbonyloxy-(C$_1$–C$_4$)-alkoxy, amino or mono- or di-((C$_1$–C$_8$)-alkyl)-amino;

$R^{11}$ is $R^{12a}$, $R^{12a}$—CO, $R^{12a}$—O—CO, $R^{12b}$—CO or $R^{12a}$—S(O)$_2$;

$R^{12a}$ is (C$_1$–C$_{10}$)-alkyl, (C$_2$–C$_8$)-alkenyl, (C$_2$–C$_8$)-alkynyl, (C$_3$–C$_{12}$)-cycloalkyl, (C$_3$–C$_{12}$)-cycloalkyl-(C$_1$–C$_8$)-alkyl, optionally substituted (C$_6$–C$_{14}$)-aryl, (C$_6$–C$_{14}$)-aryl-(C$_1$–C$_8$)-alkyl optionally substituted in the aryl radical, optionally substituted heteroaryl, heteroaryl-(C$_1$–C$_8$)-alkyl optionally substituted in the heteroaryl radical, or the radical $R^{15}$;

$R^{12b}$ is amino, di-((C$_1$–C$_{10}$)-alkyl)-amino or $R^{12a}$—NH;

$R^{13}$ is hydrogen or (C$_1$–C$_4$)-alkyl;

$R^{15}$ is $R^{16}$—(C$_1$–C$_3$)-alkyl or $R^{16}$;

$R^{16}$ is a 7-membered to 12-membered bicyclic or tricyclic radical which is saturated and which can also contain one or two identical or different heteroatoms selected from the group consisting of nitrogen, oxygen and sulfur and which can also be substituted by one or more identical or different substituents from the group consisting of (C$_1$–C$_4$)-alkyl and oxo;

Het is the radical of a 5-membered to 7-membered, saturated monocyclic heterocycle bonded via a ring nitrogen atom, which can contain one or two identical or different additional ring heteroatoms selected from the group consisting of oxygen, nitrogen and sulfur and which can be optionally substituted on carbon atoms and on additional ring nitrogen atoms, where substituents on additional ring nitrogen atoms can be identical or different radicals from the group consisting of hydrogen, $R^h$, HCO, $R^h$CO or $R^h$O—CO and $R^h$ is (C$_1$–C$_6$)-alkyl, (C$_3$–C$_8$)-cycloalkyl, (C$_3$–C$_8$)-cycloalkyl-(C$_1$–C$_4$)-alkyl, optionally substituted (C$_6$–C$_{10}$)-aryl or (C$_6$–C$_{10}$)-aryl-(C$_1$–C$_4$)-alkyl optionally substituted in the aryl radical;

e and h independently of one another are 0 or 1;

in all their stereoisomeric forms and mixtures thereof in all ratios, and their physiologically tolerable salts.

Especially preferred compounds of the formula I are on the one hand those in which B is unsubstituted methylene or methylene which is substituted by a $(C_1\text{–}C_8)$-alkyl radical, in all their stereoisomeric forms and mixtures thereof in all ratios, and their physiologically tolerable salts. Particularly especially preferred compounds of the formula I are those in which B is methylene which is substituted by a $(C_1\text{–}C_8)$-alkyl radical, in all their stereoisomeric forms and mixtures thereof in all ratios, and their physiologically tolerable salts.

Especially preferred compounds of the formula I are on the other hand those in which $R^1$ is a radical selected from the group of phenyl, furyl, thienyl, pyrrolyl, imidazolyl and pyridyl, which is unsubstituted or substituted by one, two or three identical or different substituents selected from the group consisting of $(C_1\text{–}C_4)$-alkyl, $(C_1\text{–}C_4)$-alkoxy, halogen, amino, trifluoromethyl, hydroxyl, hydroxy-$(C_1\text{–}C_4)$-alkyl, methylenedioxy, ethylenedioxy, phenyl, phenoxy, benzyl and benzyloxy, in all their stereoisomeric forms and mixtures thereof in all ratios, and their physiologically tolerable salts.

Particularly especially preferred compounds of the formula I are those in which $R^1$ is a radical selected from the group of phenyl, 2-furyl, 3-furyl, 2-thienyl, 3-thienyl, 3-pyrrolyl, 4-imidazolyl and 3-pyridyl and 4-pyridyl, where the phenyl radical is unsubstituted or substituted by one or two identical or different radicals selected from the group consisting of $(C_1\text{–}C_4)$-alkyl, $(C_1\text{–}C_4)$-alkoxy, halogen, trifluoromethyl, hydroxyl, hydroxy-$(C_1\text{–}C_4)$-alkyl, methylenedioxy, ethylenedioxy, phenyl, phenoxy, benzyl and benzyloxy and where the heteroaromatic radicals are unsubstituted or are substituted by one or two identical or different radicals selected from the group of $(C_1\text{–}C_4)$-alkyl, $(C_1\text{–}C_4)$-alkoxy, halogen, amino, trifluoromethyl, hydroxyl, hydroxy-$(C_1\text{–}C_4)$-alkyl, methylenedioxy, ethylenedioxy, phenyl, phenoxy, benzyl and benzyloxy, in all their stereoisomeric forms and mixtures thereof in all ratios, and their physiologically tolerable salts.

Very particularly especially preferred compounds of the formula I are those in which $R^1$ is an unsubstituted radical selected from the group of phenyl, 2-furyl, 3-furyl, 2-thienyl, 3-thienyl, 3-pyrrolyl, 4-imidazolyl, 3-pyridyl and 4-pyridyl, in all their stereoisomeric forms and mixtures thereof in all ratios, and their physiologically tolerable salts.

Even more especially preferred compounds of the formula I are those in which $R^1$ is an unsubstituted radical selected from the group of phenyl, 2-furyl, 3-furyl, 2-thienyl, 3-thienyl, 4-imidazolyl and 4-pyridyl, in all their stereoisomeric forms and mixtures thereof in all ratios, and their physiologically tolerable salts.

Generally, compounds of the formula I are preferred which have a uniform configuration at chiral centers, for example on the chiral carbon atom carrying the radicals $R^2$ and $R^3$ when this atom is appropriately substituted, and/or on the center W in the imidazolidine ring in the formula I.

The compounds of the formula I can be prepared as desired, for example, by fragment condensation of a compound of the formula II

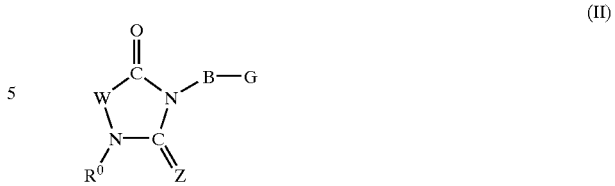

with a compound of the formula III,

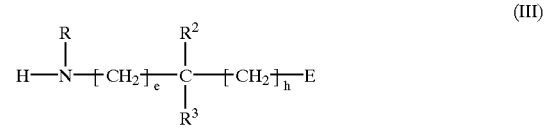

where, in the formulae II and III, the groups W, Z, B, E, R, $R^0$, $R^2$ and $R^3$ as well as e and h are defined as indicated above or alternatively in these groups functional groups can be present in protected form or in the form of precursors, and where G is hydroxycarbonyl, $(C_1\text{–}C_6)$-alkoxycarbonyl or activated carboxylic acid derivatives such as acid chlorides or active esters. If compounds of the formula I are to be prepared in which, for example, $R^3$ in the formula I is a carboxylic acid derivative or contains such a derivative, it is also possible that in the compounds of the formula III the radical $R^3$ initially is a hydroxycarbonyl group present in protected form or contains such a group in protected form, and that then the desired final group $R^3$ is synthesized in one or more further steps only after the condensation of the compounds of the formulae II and III.

For the condensation of the compounds of the formula II with those of the formula III, the coupling methods of peptide chemistry well-known per se to the person skilled in the art are advantageously used (see, for example, Houben-Weyl, Methoden der Organischen Chemie [Methods of Organic Chemistry], Volume 15/1 and 15/2, Georg Thieme Verlag, Stuttgart, 1974), incorporated herein by reference. Possible condensing agents are, for example, carbonyldiimidazole, carbodiimides such as dicyclohexylcarbodiimide or diisopropylcarbodiimide, O-((cyano (ethoxycarbonyl)methylen)amino)-N,N,N',N'-tetramethyluronium tetrafluoroborate (TOTU) or propylphosphonic anhydride (PPA). Generally, it is necessary in the condensation to protect nonreacting amino groups present by reversible protective groups. The same applies to carboxyl groups not involved in the reaction, which are preferably present during the condensation as $(C_1\text{–}C_6)$-alkyl esters, for example tert-butyl esters, or as benzyl esters. Amino group protection is unnecessary if the amino groups are still present in the form of precursors, for example as nitro groups, and are only formed after coupling, for example by hydrogenation. After coupling, the protective groups present are removed in a suitable manner. For example, $NO_2$ groups (guanidino protection in amino acids), benzyloxycarbonyl groups and benzyl groups in benzyl esters can be removed by hydrogenation. The protective groups of the tert-butyl type are removed under acidic conditions, while the 9-fluorenylmethyloxycarbonyl radical is removed by secondary amines. The compounds of the formula I can also be prepared, for example, by synthesizing the compounds stepwise on a solid phase according to customary methods, where the individual structural elements of the molecule can be introduced in varying sequences.

Compounds of the formula II in which W is $R^1$—A—C($R^{13}$) and Z is oxygen can be prepared, for example, by first reacting compounds of the formula IV

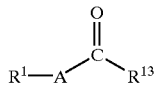
(IV)

in a Bucherer reaction to give compounds of the formula V

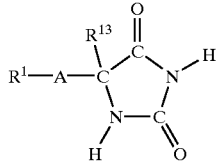
(V)

in which, as well as in the formula IV, $R^1$, $R^{13}$ and A are defined as indicated above (H. T. Bucherer, V. A. Lieb, J. Prakt. Chem. 141(1934), 5).

Compounds of the formula VI

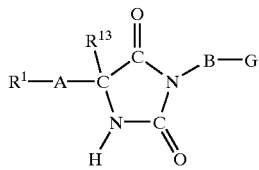
(VI)

in which $R^1$, $R^{13}$, A, B and G are defined as indicated above, can then be obtained by first reacting the compounds of the formula V, for example, with an alkylating reagent which introduces the radical —B—G into the molecule. The reaction of compounds of the formula VI with a second reagent of the formula $R^0$—LG, in which $R^0$ has the meanings indicated above and LG is a nucleophilically substitutable leaving group, for example halogen, in particular chlorine or bromine, ($C_1$–$C_4$)-alkoxy, optionally substituted phenoxy or a heterocyclic leaving group such as, for example, imidazolyl, leads to the corresponding compounds of the formula II. These reactions can be carried out analogously to known methods familiar to the person skilled in the art. Depending on the individual case, it may be appropriate here, as in all steps in the synthesis of the compounds of the formula I, to temporarily block functional groups which could lead to secondary reactions or undesired reactions by means of a protective group strategy tailored to the synthesis problem, as is known to the person skilled in the art. With respect to the preparation of the compounds of the formulae V and VI in racemic form and in enantiomerically pure form, reference is in particular made here to the corresponding embodiments in WO-A-96/33976, which is hereby incorporated by reference in its entirety.

If W is $R^1$—A—CH=C, this structural element can be introduced, for example, by condensing, analogously to known methods, an aldehyde with a dioxoimidazolidine or thioxo-oxoimidazolidine which contains an unsubstituted methylene group in the position corresponding to the group W.

The amino compounds of the formula III can be synthesized, according to or analogously to well-known standard procedures, from starting compounds which are commercially available or are obtainable according to or analogously to literature procedures.

Compounds of the formula I in which W is $R^1$—A—C($R^{13}$) can also be obtained as follows:

By reaction of α-amino acids or N-substituted α-amino acids obtainable according to standard procedures or preferably their esters, for example the methyl ester, ethyl ester, tert-butyl ester or benzyl ester, for example of a compound of the formula VII

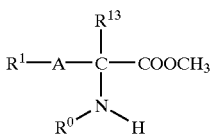
(VII)

in which $R^0$, $R^1$, $R^{13}$ and A are defined as indicated above, with an isocyanate or isothiocyanate, for example of the formula VIII

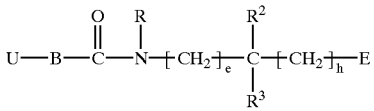
(VIII)

in which B, E, R, $R^2$, $R^3$, e and h are defined as indicated above and U is isocyanato or isothiocyanato, urea derivatives or thiourea derivatives of the formula IX

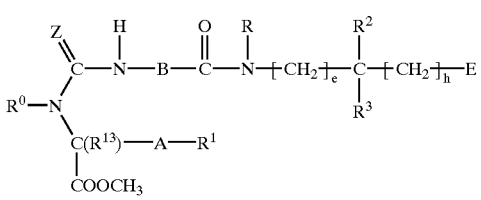
(IX)

are obtained for which the definitions indicated above apply, and which are cyclized by heating with acid with hydrolysis of the ester functions to give compounds of the formula Ia

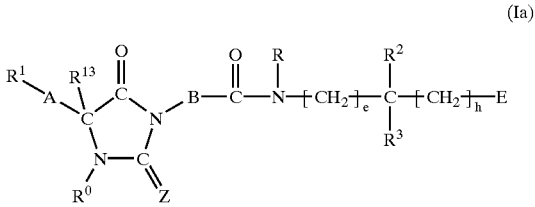
(Ia)

for which the meanings indicated above apply. The cyclization of the compounds of the formula IX to the compounds of the formula Ia can also be carried out by treatment with bases in inert solvents, for example by treatment with sodium hydride in an aprotic solvent such as dimethylformamide. During the cyclization, functional groups can in turn be present in protected form.

Compounds of the formula I in which W is $R^1$—A—C($R^{13}$) can also be obtained by reacting a compound of the formula VII with an isocyanate or isothiocyanate of the formula X

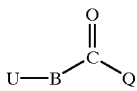
(X)

in which B and U are defined as indicated above for the formula VIII and Q is an alkoxy group, for example a $(C_1-C_4)$-alkoxy group such as methoxy, ethoxy or tert-butoxy, a $(C_6-C_{14})$-aryloxy group, for example phenoxy, or a $(C_6-C_{14})$-aryl-$(C_1-C_4)$-alkoxy group, for example benzyloxy. In this case a compound of the formula XI

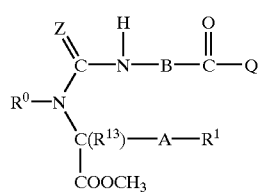
(XI)

is obtained in which Z, A, B, Q, $R^0$, $R^1$ and $R^{13}$ are defined as indicated above for the formulae IX and X, which is then cyclized under the influence of an acid or of a base, such as described above for the cyclization of the compounds of the formula IX, to give a compound of the formula XII

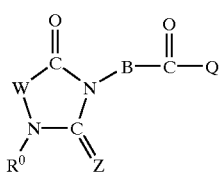
(XII)

in which W is $R^1$—A—$C(R^{13})$ and Z, B, Q and $R^0$ are defined as indicated above for the formulae Ia and X. From the compound of the formula XII a compound of the formula Ia is then obtained by hydrolysis of the group CO—Q to the carboxylic acid COOH and subsequent coupling with a compound of the formula III, as described above for the coupling of the compounds of the formulae II and III. Here too, during the cyclization functional groups can be present in protected form or in the form of precursors.

A further method for the preparation of compounds of the formula Ia is, for example, the reaction of compounds of the formula XIII

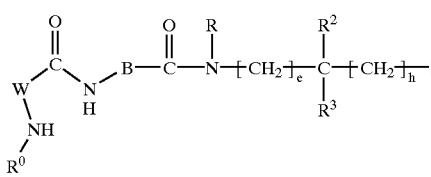
(XIII)

in which W is $R^1$—A—$C(R^{13})$ and for which otherwise the definitions indicated above apply, with phosgene, thiophosgene or corresponding equivalents (analogously to S. Goldschmidt and M. Wick, Liebigs Ann. Chem. 575 (1952), 217–231 and C. Tropp, Chem. Ber. 61 (1928), 1431–1439).

With respect to the preparation of the compounds of the formula I, reference is furthermore fully made to WO-A-95/14008, EP-A-796 855 (European Patent Application 97103712.2) and the applications corresponding to it, as well as to WO-A-96/33976, all of which are incorpoorated by reference in their entireties.

The compounds of the formula I are valuable pharmaceutically active compounds which are suitable, for example, for the therapy and prophylaxis of inflammatory disorders, allergic disorders or asthma. The compounds of the formula I and their physiologically tolerable salts can be administered according to the invention to animals, preferably to mammals, and in particular to man, as pharmaceuticals for therapy or prophylaxis. They can be administered per se, in mixtures with one another or in the form of pharmaceutical preparations which permit enteral or parenteral administration and which as active constituent contain an efficacious dose of at least one compound of the formula I and/or its physiologically tolerable salts in addition to customary pharmaceutically innocuous excipients and/or additives.

The present invention therefore also relates to the compounds of the formula I and/or their physiologically tolerable salts for use as pharmaceuticals, the use of the compounds of the formula I and/or their physiologically tolerable salts for the production of pharmaceuticals for the therapy and prophylaxis of the diseases described above or in the following, for example for the therapy and prophylaxis of inflammatory disorders, and the use of the compounds of the formula I and/or their physiologically tolerable salts in the therapy and prophylaxis of these diseases. The present invention furthermore relates to pharmaceutical preparations which contain an efficacious dose of at least one compound of the formula I and/or its physiologically tolerable salts in addition to customary pharmaceutically innocuous excipients and/or additives.

The pharmaceuticals can be administered orally, for example in the form of pills, tablets, film-coated tablets, sugar-coated tablets, granules, hard and soft gelatin capsules, solutions, syrups, emulsions or suspensions. However, administration can also be carried out rectally, for example in the form of suppositories, or parenterally, for example in the form of injection or infusion solutions, microcapsules or rods, or percutaneously, for example in the form of ointments, solutions or tinctures, or in another way, for example in the form of nasal sprays or aerosol mixtures.

The pharmaceutical preparations according to the invention are prepared in a manner known per se, pharmaceutically inert inorganic or organic excipients being used in addition to the compound(s) of the formula I and/or its/their physiologically tolerable salts. For the preparation of pills, tablets, sugar-coated tablets and hard gelatin capsules, it is possible to use, for example, lactose, cornstarch or derivatives thereof, talc, stearic acid or its salts etc. Excipients for soft gelatin capsules and suppositories are, for example, fats, waxes, semisolid and liquid polyols, natural or hardened oils etc. Suitable excipients for the preparation of solutions, for example injection solutions, or of emulsions or syrups are, for example, water, alcohols, glycerol, polyols, sucrose, invert sugar, glucose, vegetable oils etc. Suitable excipients for microcapsules, implants or rods are, for example, copolymers of glycolic acid and lactic acid. The pharmaceutical preparations normally contain approximately 0.5 to 90% by weight of the compounds of the formula I and/or their physiologically tolerable salts.

In addition to the active compounds and excipients, the pharmaceutical preparations can additionally contain additives, such as, for example, fillers, disintegrants, binders, lubricants, wetting agents, stabilizers, emulsifiers, preservatives, sweeteners, colorants, flavorings or aromatizers, thickeners, diluents, buffer substances, and also solvents or solubilizers or means for achieving a depot effect, as well as salts for altering the osmotic pressure, coating agents or antioxidants. They can also contain two or more compounds of the formula I and/or their physiologically tolerable salts. Furthermore, they can also contain one or more other therapeutically or prophylactically active substances in addition to at least one compound of the formula I and/or its physiologically tolerable salts, for example substances having antiinflammatory action. The pharmaceutical preparations normally contain 0.2 to 500 mg, preferably 1 to 100 mg, of active compound of the formula I and/or its physiologically tolerable salts.

The compounds of the formula I have the ability to inhibit cell-cell and cell-matrix interaction processes in which interactions between VLA-4 with its ligands play a part. The efficacy of the compounds of the formula I can be demonstrated, for example, in an assay in which the binding of cells which contain the VLA-4 receptor, for example of leucocytes, to ligands of this receptor is measured, for example to VCAM-1, which for this purpose can advantageously also be prepared by genetic engineering. Details of such an assay are described below. In particular, the compounds of the formula I are able to inhibit the adhesion and the migration of leucocytes, for example the adhesion of leucocytes to endothelial cells which—as explained above—is controlled via the VCAM-1/VLA-4 adhesion mechanism. Besides as antiinflammatory agents, the compounds of the formula I and their physiologically tolerable salts are therefore generally suitable for the therapy and prophylaxis of diseases which are based on the interaction between the VLA-4 receptor and its ligands or can be affected by an inhibition of this interaction, and in particular they are suitable for the therapy and prophylaxis of diseases which are caused at least partially by an undesired extent of leucocyte adhesion and/or leucocyte migration or are associated therewith, or for whose prevention, alleviation or cure the adhesion and/or migration of leucocytes should be decreased.

The compounds of the formula I can be employed as antiinflammatories in the case of a variety of inflammatory symptoms. They are used, for example, for the therapy or prophylaxis of rheumatoid arthritis, of inflammatory bowel disease (ulcerative colitis), of systemic lupus erythematosus or for the therapy or prophylaxis of inflammatory disorders of the central nervous system such as, for example, multiple sclerosis, for the therapy or prophylaxis of asthma or of allergies, for example allergies of the delayed type (type IV allergy). They are furthermore suitable for the therapy or prophylaxis of cardiovascular disorders, arteriosclerosis, of restenoses, for the therapy or prophylaxis of diabetes, for the prevention of damage to organ transplants, for the inhibition of tumor growth or formation of tumor metastases in various malignancies, for the therapy of malaria as well as of other diseases in which blocking of the integrin VLA-4 and/or influencing of the leucocyte activity appears appropriate for prevention, alleviation or cure.

The dose when using the compounds of the formula I can vary within wide limits and is to be tailored to the individual conditions in each individual case as is customary. The dose depends, for example, on the compound employed or on the nature and severity of the disease to be treated or on whether an acute or chronic disease state is treated or whether prophylaxis is conducted. In general, in the case of oral administration a daily dose of approximately 0.01 to 100 mg/kg, preferably 0.1 to 10 mg/kg, in particular 0.3 to 2 mg/kg (in each case per kg of body weight) is appropriate in an adult weighing about 75 kg to achieve effective results. In the case of intravenous administration, the daily dose is in general approximately 0.01 to 50 mg/kg, preferably 0.01 to 10 mg/kg of body weight. In particular when relatively large amounts are administered, the daily dose can be divided into a number of, for example 2, 3 or 4, part administrations. If appropriate, depending on individual behavior, it may be necessary to deviate upward or downward from the indicated daily dose.

The present invention therefore also relates to the compounds of the formula I for the inhibition of the adhesion and/or migration of leucocytes or for the inhibition of the VLA-4 receptor and the use of the compounds of the formula I for the production of pharmaceuticals therefor, i.e., of pharmaceuticals for the therapy or prophylaxis of diseases in which leucocyte adhesion and/or leucocyte migration exhibits an undesired extent, or of diseases in which VLA-4-dependent adhesion processes play a part, as well as the use of the compounds of the formula I and/or their physiologically tolerable salts in the therapy and prophylaxis of diseases of this type.

The compounds of the formula I and their salts can furthermore be employed for diagnostic purposes, for example in in-vitro diagnoses, and as auxiliaries in biochemical investigations in which VLA-4 blocking or influencing of cell-cell or cell-matrix interactions is intended. They can furthermore be used as intermediates for the preparation of other compounds, in particular of other pharmaceutically active compounds which are obtainable from the compounds of the formula I, for example, by modification or introduction of radicals or functional groups.

EXAMPLES

The following examples demonstrate the present invention. The examples are for illustrative purposes and do not limit the scope of the invention.

The compounds were identified by means of mass spectra (MS) and/or NMR spectra. Compounds which were purified by chromatography using an eluent which contained, for example, acetic acid or trifluoroacetic acid, and then freeze-dried, sometimes still contained the acid derived from the eluent, depending on how the freeze drying was carried out, and were thus obtained partially or completely in the form of a salt of the acid used, for example in the form of the acetic acid salt or trifluoroacetic acid salt.

The abbreviations have the following meanings:

| | |
|---|---|
| DMF | N,N-dimethylformamide |
| THF | tetrahydrofuran |
| DCC | N,N'-dicyclohexylcarbodiimide |
| HOBt | 1-hydroxybenzotriazole |
| TOTU | O-(cyano(ethoxycarbonyl)methylenamino)-1,1,3,3-tetramethyluronium tetrafluoroborate |

Example 1
((R,S)-2-((S)-4-Phenyl-3-benzyl-4-methyl-2,5-dioxoimidazolidin-1-yl)-2-(2-methylpropyl)acetyl)-L-aspartyl-L-phenylglycine

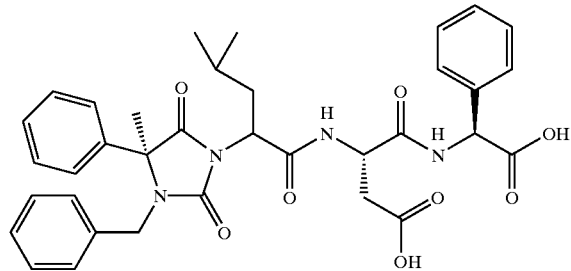

1a) tert-Butyl (R,S)-2-bromo-4-methylpentanoate (1.1)

1.96 ml of concentrated sulfuric acid and 0.515 ml of oleum (20% strength) were added to a solution of 2.5 g (12.8 mmol) of (R,S)-2-bromo-4-methylpentanoic acid in 80 ml of chloroform and 80 ml of tert-butyl acetate and the mixture was stirred at room temperature for 3 h. A pH of 4 was then established by addition of 10% strength NaHCO$_3$ solution. The aqueous phase was separated off and extracted 2× with dichloromethane. The combined organic phases were dried over sodium sulfate. After filtration and concentration of the filtrate in vacuo, 2.62 g (82%) of 1.1 were obtained.

1b) tert-Butyl (R,S)-2-((S)-4-(4-bromophenyl)-4-methyl-2,5-dioxoimidazolidin-1-yl)-4-methylpentanoate (1.2)

213 mg (8.87 mmol) of sodium hydride were added at 0° C. under argon to a solution of 2.08 g (7.72 mmol) of (S)-4-(4-bromophenyl)-4-methyl-2,5-dioxoimidazolidine in 20 ml of absolute DMF, the mixture was stirred at room temperature for 1 h, 1.94 g (7.72 mmol) of 1.1 were added, and the mixture was stirred at room temperature for 5 h and allowed to stand at room temperature overnight. The solvent was removed in vacuo, the residue was taken up in ethyl acetate and the ethyl acetate solution was washed with water. The organic phase was dried over sodium sulfate, the drying agent was filtered off and the filtrate was concentrated in vacuo. The residue was chromatographed on silica gel using heptane/ethyl acetate (2:1). After concentration of the product fractions, 2.45 g (72%) of 1.2 were obtained.

1c) tert-Butyl (R,S)-2-((S)-4-(4-bromophenyl)-3-benzyl-4-methyl-2,5-dioxoimidazolidin-1-yl)-4-methylpentanoate (1.3)

126 mg (5.24 mmol) of sodium hydride were added at 0° C. under argon to a solution of 1.92 g (4.37 mmol) of 1.2 in 10 ml of absolute DMF, the mixture was stirred at room temperature for 1 h, 570 µl (4.8 mmol) of benzyl bromide were added and the mixture was stirred at room temperature for another 1 h. The solvent was removed in vacuo, the residue was partitioned between water and ethyl acetate and, after phase separation, the water phase was extracted with ethyl acetate. The combined organic phases were dried over sodium sulfate, the drying agent was filtered off and the filtrate was concentrated in vacuo. 2.17 g (94%) of 1.3 were obtained.

1d) (R,S )-2-((S)-4-Phenyl-3-benzyl-4-methyl-2,5-dioxoimidazolidin-1-yl)-4-methylpentanoic acid (1.4)

A solution of 1 g (1.88 mmol) of 1.3 in 100 ml of ethanol was hydrogenated over 40 mg of 10% Pd/C. After 2 h, the catalyst was filtered off, the filtrate was concentrated in vacuo, the residue was dissolved in ethyl acetate and the solution was washed with 10% strength NaHCO$_3$ solution and water and dried over sodium sulfate. After filtration and removal of the solvent in vacuo, the residue was treated with 10 ml of 90% strength trifluoroacetic acid. After 15 min at room temperature, the trifluoroacetic acid was removed in vacuo and the residue was evaporated 2× with toluene. 740 mg (100%) of 1.4 were obtained.

1e) ((R,S)-2-((S)-4-Phenyl-3-benzyl-4-methyl-2,5-dioxoimidazolidin-1-yl)-2-(2-methylpropyl)acetyl)-L-aspartyl-L-phenylglycine (1.5)

166 mg (0.507 mmol) of TOTU and 172 µl (1.014 mmol) of diisopropylethylamine were added to a solution of 200 mg (0.507 mmol) of 1.4 and 210 mg (0.507 mmol) of H-Asp(O$^t$Bu)-Phg-O$^t$Bu hydrochloride in 10 ml of absolute DMF. After stirring at room temperature for 2 h, the reaction mixture was concentrated in vacuo, the residue was taken up in ethyl acetate and the organic phase was washed 2× with saturated NaHCO$_3$ solution and water. After drying over sodium sulfate, filtration and concentration of the filtrate in vacuo, 393 mg of crude product were obtained, which was chromatographed on silica gel using heptane/ethyl acetate (3:1). After concentration of the product fractions, the residue was dissolved in 5 ml of 90% strength trifluoroacetic acia, the trifluoroacetic acid was removed in vacuo after 15 min at room temperature and the residue was dissolved in 20% strength acetic acid and freeze-dried. 219 mg (67%) of 1.5 were obtained.

ES(+)-MS: 643.3 (M+H)$^+$

Example 2
(S)-3-((R,S)-2-((S)-4-Phenyl-3-benzyl-4-methyl-2,5-dioxoimidazolidin-1-yl)-2-(2-methylpropyl)acetylamino)-2-benzyloxycarbonylaminopropionic acid

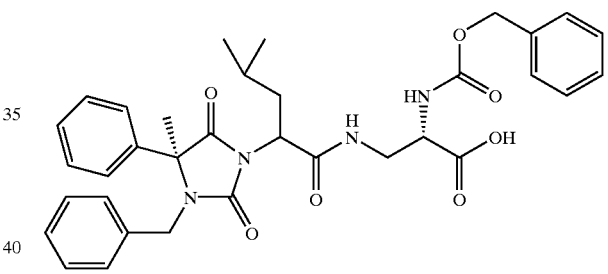

The compound was prepared by reaction of (R,S)-2-((S)-4-phenyl-3-benzyl-4-methyl-2,5-dioxoimidazolidin-1-yl)-4-methylpentanoic acid (1.4) and tert-butyl (S)-3-amino-2-benzyloxycarbonylaminopropionate analogously to the preparation of 1.4. After cleavage of the tert-butyl ester and removal of the trifluoroacetic acid in vacuo, the residue was chromatographed on silica gel using dichloromethane/methanol/acetic acid/water (9:1:0.1:0.1).

ES(+)-MS: 615.4 (M+H)$^+$

The tert-butyl (S)-3-amino-2-benzyloxycarbonylaminopropionate was prepared as follows. 10 g (42 mmol) of (S)-3-amino-2-benzyloxycarbonylaminopropionic acid were shaken in a mixture of 100 ml of dioxane, 100 ml of isobutylene and 8 ml of conc. H$_2$SO$_4$ in an autoclave under an N$_2$ pressure of 20 atm for 3 days. Excess isobutylene was blown out and 150 ml of diethyl ether and 150 ml of saturated NaHCO$_3$ solution were added to the remaining solution. The phases were separated and the aqueous phase was extracted 2× using 100 ml of diethyl ether each time. The combined organic phases were washed with 2×100 ml of water and dried over Na$_2$SO$_4$ After removal of the solvent in vacuo, 9.58 g (78%) of tert-butyl (S)-3-amino-2-benzyloxycarbonylaminopropionate were obtained as a pale yellow oil.

Example 3
(R,S)-3-((R,S)-2-((S)-4-Phenyl-3-benzyl-4-methyl-2,5-dioxoimidazolidin-1-yl)-2-(2-methylpropyl)acetylamino)-3-(3,4-methylenedioxyphenyl)propionic Acid

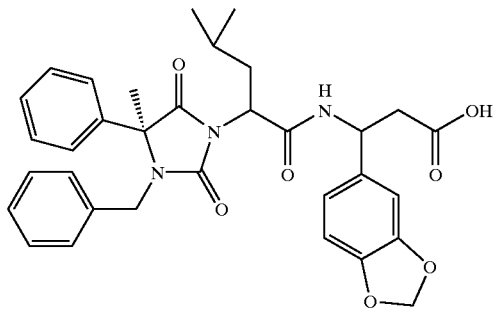

The compound was prepared by reaction of 1.4 with tert-butyl (R,S)-3-amino-3-(3,4-methylenedioxyphenyl)propionate hydrochloride and subsequent cleavage of the tert-butyl ester as described in Example 1.

ES(+)-MS: 586.3 (M+H)$^+$

The tert-butyl (R,S)-3-amino-3-(3,4-methylendioxyphenyl)propionate hydrochloride was prepared by initially preparing the corresponding β-amino acid analogously to W. M. Radionow, E. A. Postovskaya, J. Am. Chem. Soc. 1929, 51, 841 (see also Houben-Weyl, Methoden der Organischen Chemie [Methods of Organic Chemistry], Volume XI/2, Georg Thieme Verlag, Stuttgart, 1958, p. 497). This was converted into the benzyloxycarbonylamino derivative, from which the tert-butyl ester was then obtained according to the following synthesis procedure: 1.5 mmol of oxalyl chloride were added to 1 mmol of the 3-benzyloxycarbonylamino carboxylic acid in 13 ml of absolute dichloromethane. After stirring at room temperature for 4 h, the reaction mixture was concentrated and 6.5 ml of tert-butanol were added to the residue. The reaction mixture was stirred at room temperature for 1 h and concentrated in vacuo. The residue was taken up in ethyl acetate and extracted 2× with saturated NaHCO₃ solution and water. The organic phase was dried over sodium sulfate and after filtration the solvent was removed in vacuo. For the preparation of the 9-amino acid tert-butyl ester hydrochloride, the benzyloxycarbonyl group was then removed by hydrogenation over 10% Pd/C in methanol/HCl.

Example 4
(S)-3-((R,S)-2-((R,S)-4-Phenyl-3-benzyl-4-methyl-2,5-dioxoimidazolidin-1-yl)-2-isopropylacetylamino)-2-(1-adamantylmethyloxycarbonylamino)-propionic acid

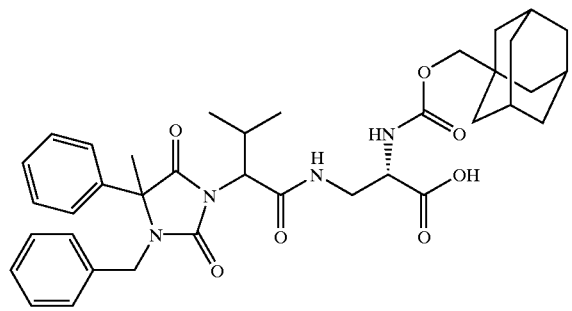

The compound was prepared by reaction of (R,S)-2-((R,S)-3-benzyl-4-phenyl-4-methyl-2,5-dioxoimidazolidin-1-yl)-2-isopropylacetic acid (prepared analogously to the procedures in Example 1 from (R,S)-4-methyl-4-phenyl-2,5-dioxoimidazolidine) with tert-butyl (S)-3-amino-2-(1-adamantylmethyloxycarbonylamino)propionate and subsequent cleavage of the tert-butyl ester as described in Example 1. The crude product was purified on RP-18 by means of preparative HPLC.

ES(+)-MS: 659.4 (M+H)$^+$

The tert-butyl (S)-3-amino-2-(1-adamantylmethyloxycarbonylamino)-propionate was prepared as follows.

8.9 g (40.8 mmol) of di-tert-butyl dicarbonate and subsequently, in portions, 1 N NaOH were added to a solution of 10 g (34 mmol) of tert-butyl (S)-3-amino-2-benzyloxycarbonylaminopropionate (see Example 2) in 600 ml of THF/water (2:1) at 0° C. such that the pH of the solution was between 9 and 10 (consumption of 1 N NaOH: 32 ml). After stirring at room temperature for 3 h, 1 l of water was added and the mixture was extracted 3 times with diethyl ether. After drying the organic phase over sodium sulfate, filtration and removal of the solvent in vacuo, the residue was chromatographed on silica gel using dichloromethane/methanol (20:1). 13.19 g (98%) of tert-butyl (S)-2-benzyloxycarbonylamino-3-tert-butoxycarbonylaminopropionate were obtained.

13.1 g of tert-butyl (S)-2-benzyloxycarbonylamino-3-tert-butoxycarbonylaminopropionate were hydrogenated over 10% Pd/C in methanol/HCl. After 1.5 h, the mixture was filtered and the filtrate was concentrated in vacuo. 9.77 g (99%) of tert-butyl (S)-2-amino-3-tert-butoxycarbonylaminopropionate hydrochloride were obtained as a colorless solid.

A solution of 10.9 g (65.4 mmol) of 1-hydroxymethyladamantane and 10.6 g (65.4 mmol) of carbonyldiimidazole in 60 ml of THF was stirred at 50° C. for 1.5 h. 9.7 g (32.7 mmol) of tert-butyl (S)-2-amino-3-tert-butoxycarbonylaminopropionate hydrochloride in 25 ml of THF and 5.6 ml (32.7 mmol) of diisopropylethylamine were added, and the mixture was stirred at 60° C. for 4 h and allowed to stand at room temperature overnight. The solvent was removed in vacuo and the residue was chromatographed on silica gel using heptane/ethyl acetate (7:3). 8.7 g (59%) of tert-butyl (S)-2-(1-adamantylmethyloxycarbonylamino)-3-tert-butoxycarbonylaminopropionate were obtained as a colorless oil.

A solution of 8.7 g (19.22 mmol) of tert-butyl (S)-2-(1-adamantylmethyloxycarbonylamino)-3-tert-butoxycarbonylamino-propionate in 180 ml of trifluoroacetic acid/dichloromethane (1:1) was added after 1 min to 1.5 l of ice-cold NaHCO₃ solution, the mixture was extracted three times with dichloromethane and the dichloromethane phases were then dried over sodium sulfate. After filtration and removal of the solvent in vacuo, 6.35 g (94%) of tert-butyl (S)-3-amino-2-(1-adamantylmethyloxycarbonylamino)-propionate were obtained as a colorless solid.

Example 5

((R,S)-4-(4-Pyridyl)-3-benzyl-4-methyl-2,5-dioxoimidazolidin-1-yl)-acetyl-L-aspartyl-L-phenylglycine

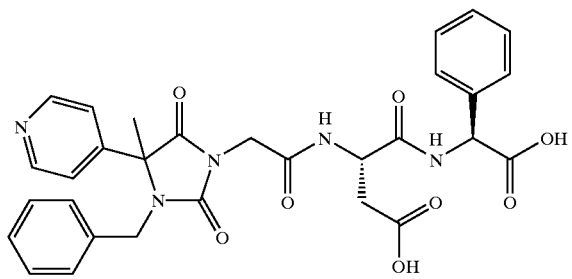

5a) (R,S)-4-(4-Pyridyl)-4-methyl-2,5-dioxoimidazolidine (5.1)

36.34 g (300 mmol) of 4-acetylpyridine and 259.2 g (2.694 mol) of ammonium carbonate were suspended in 400 ml of 50% strength ethanol. 25.5 g (392 mmol) of potassium cyanide were added thereto. The mixture was stirred at 50–60° C. for 5 hours, allowed to cool to room temperature, the pH was adjusted to 6.3 by addition of 6 N HCl and the mixture was allowed to stand at room temperature overnight. It was again adjusted to a pH of 6.3 and the solvent was removed in vacuo. The residue was suspended several times using dichloromethane. The insoluble portions were in each case filtered off and the combined filtrates were concentrated in vacuo. The residue was chromatographed on silica gel using dichloromethane/methanol. After concentration of the product fractions, −37.53 g (65%) of 5.1 were obtained.

5b) ((R,S)-4-(4-Pyridyl)-3-benzyl-4-methyl-2,5-dioxoimidazolidin-1-yl)-acetyl-L-aspartyl-L-phenylglycine (5.2)

43.6 mg of TOTU and 68 µl of diisopropylethylamine were added to a solution of 50 mg (0.133 mmol) of ((R,S)-4-(4-pyridyl)-3-benzyl-4-methyl-2,5-dioxoimidazolidin-1-yl)acetic acid hydrochloride (prepared by cleavage of tert-butyl ((R,S)-4-(4-pyridyl)-3-benzyl-4-methyl-2,5-dioxoimidazolidin-1-yl)acetate with 90% strength trifluoroacetic acid and subsequent conversion into the hydrochloride, the tert-butyl ((R,S)-4-(4-pyridyl)-3-benzyl-4-methyl-2,5-dioxoimidazolidin-1-yl)acetate being prepared by alkylation of 5.1 first with tert-butyl bromoacetate and then with benzyl bromide analogously to Example 1) and 55 mg (0.133 mmol) of H-Asp(O'Bu)-Phg-(O'Bu)×HCl in 10 ml of absolute DMF. After 3 d at room temperature, the solvent was removed in vacuo, the residue was taken up in ethyl acetate, and the solution was washed with saturated NaHCO$_3$ solution, water and KHSO$_4$/K$_2$SO$_4$ solution and dried over sodium sulfate. After filtration, the solvent was removed in vacuo and the residue was treated with 10 ml of 90% strength trifluoroacetic acid. After 1 h at room temperature, the trifluoroacetic acid was removed in vacuo, the residue was partitioned between diethyl ether and water, the aqueous phase was freeze-dried and the residue was purified by chromatography on silica gel two times. 19.5 mg (25%) of 5.2 were obtained.

ES(+)-MS: 588.3 (M+H)$^+$

Example 6

((R,S)-2-((R,S)-4-(4-Pyridyl)-3-benzyl-4-methyl-2,5-dioxoimidazolidin-1-yl)-2-(2-methylpropyl)acetyl)-L-aspartyl-L-phenylglycine

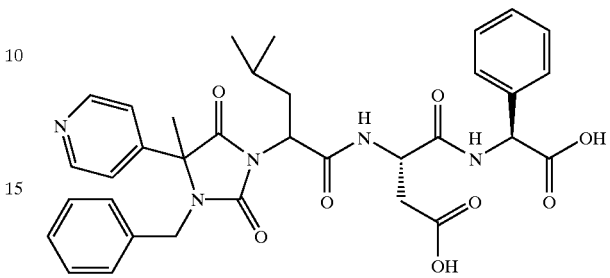

6a) tert-Butyl (R,S)-2-((R,S)-4-(4-pyridyl)-3-benzyl-4-methyl-2,5-dioxoimidazolidin-1-yl)-2-(2-methylpropyl)acetate (6.1)

1.03 g (23.58 mmol) of sodium hydride were added with ice-cooling to a solution of 4.1 g (21.44 mmol) of (R,S)-4-(4-pyridyl)-4-methyl-2,5-dioxoimidazolidine (see Example 5) in 30 ml of absolute DMF. The mixture was stirred at room temperature for 15 min and 4.23 g (21.44 mmol) of tert-butyl (R,S)-2-bromo-4-methylpentanoate were then added. After stirring for 2 h and standing overnight at room temperature, the solvent was removed in vacuo and the residue was chromatographed on silica gel using dichloromethane/methanol (95:5). 1.2 g (15%) of tert-butyl (R,S)-2-((R,S)-4-(4-pyridyl)-4-methyl-2,5-dioxoimidazolidin-1-yl)-2-(2-methylpropyl)acetate were obtained, which was converted to 6.1 analogously to Example 1 by reaction with benzyl bromide.

6b) (R,S)-2-((R,S)-4-(4-Pyridyl)-3-benzyl-4-methyl-2,5-dioxoimidazolidin-1-yl)-2-(2-methylpropyl)acetic acid hydrochloride (6.2)

1.4 g (3.1 mmol) of 6.1 in 30 ml of 90% strength trifluoroacetic acid were stirred at room temperature for 1 h. The trifluoroacetic acid was removed in vacuo and the residue was partitioned between diethyl ether and water. The phases were separated, the organic phase was concentrated and the residue was purified on silica gel using dichloromethane/methanol/acetic acid/water (9.5:0.5:0.05:0.05). 650 mg (47%) of 6.2 were obtained.

6c) ((R,S)-2-((R,S)-4-(4-Pyridyl)-3-benzyl-4-methyl-2,5-dioxoimidazolidin-1-yl)-2-(2-methylpropyl)acetyl)-L-aspartyl-L-phenylglycine The compound was prepared analogously to Example 5 by reaction of 6.2 with H-Asp(O'Bu)-Phg-(O'Bu)×HCl and subsequent cleavage of the tert-butyl ester.

ES(+)-MS: 644.3 (M+H)$^+$

Example 7
((R,S)-4-Phenyl-3-benzyl-4-methyl-2,5-dioxoimidazolidin-1-yl)acetyl-L-aspartyl-L-phenylglycine

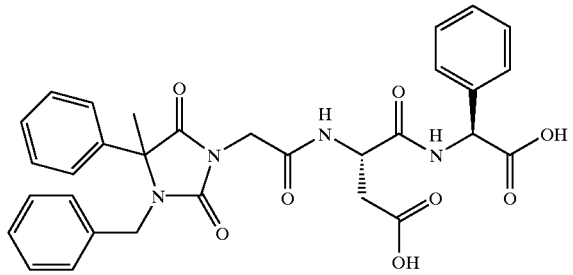

The compound was prepared by reaction of ((R,S)-4-(4-phenyl)-3-benzyl-4-methyl-2,5-dioxoimidazolidin-1-yl) acetic acid (prepared analogously to Example 1 from (R,S)-4-phenyl-4-methyl-2,5-dioxoimidazolidine by alkylation with methyl chloroacetate and then with benzyl bromide and subsequent cleavage of the methyl ester) with H-Asp(O'Bu)-Phg-(O'Bu)×HCl analogously to Example 1 and subsequent cleavage of the tert-butyl ester.

ES(+)-MS: 587.1 (M+H)$^+$

Example 8
((S)-4-(4-Hydroxymethylphenyl)-3-benzyl-4-methyl-2,5-dioxoimidazolidin-1-yl)acetyl-L-aspartyl-L-phenylglycine

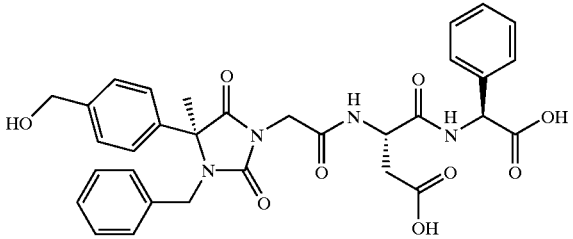

8a) Benzyl ((S)-4-(4-cyanophenyl)-3-benzyl-4-methyl-2,5-dioxoimidazolidin-1-yl)acetate (8.1)

7.73 g (160.8 „ mol) of sodium hydride were added to a solution of 20 g (73.1 mmol) of ((S)-4-(4-cyanophenyl)-4-methyl-2,5-dioxoimidazolidin-1-yl)-acetic acid in 120 ml of absolute DMF with ice-cooling. After stirring at room temperature for 30 min, 19 ml (160.8 mmol) of benzyl bromide were added. The reaction mixture was stirred at room temperature for 2 h, allowed to stand overnight, the solvent was removed in vacuo and the residue was chromatographed on silica gel using heptane/ethyl acetate (2:1). 11.43 g (35%) of 8.1 were obtained.

8b) Benzyl ((S)-4-(4-formylphenyl)-3-benzyl-4-methyl-2,5-dioxoimidazolidin-1-yl)acetate (8.2)

24.3 g of sodium hypophosphite×H$_2$O and 4.02 g of Raney nickel were added to a solution of 6.08 g (13.42 mmol) of 8.1 in 200 ml of pyridine/acetic acid/water (2:1:1) at 0° C. and the reaction mixture was heated at 60° C. for 8 h. After cooling to room temperature and filtration, the reaction mixture was concentrated in vacuo, the residue was taken up in ethyl acetate and the ethyl acetate phase was extracted 2× with water, 2× with 10% strength citric acid solution, 2× with saturated NaHCO$_3$ solution and with saturated sodium chloride solution. The organic phase was dried over magnesium sulfate and, after filtration, the solvent was removed in vacuo. 4.82 g (79%) of 8.2 were obtained.

8c) ((S)-4-(4-Hydroxymethylphenyl)-3-benzyl-4-methyl-2,5-dioxoimidazolidin-1-yl)acetic acid (8.3)

20 ml of water and then, at 0° C., 22 mg (0.6 mmol) of sodium borohydride were added to a solution of 500 mg (1.1 mmol) of 8.2 in 50 ml of ethanol. After stirring at 0° C. for 40 min, the reaction mixture was concentrated in vacuo, the residue was heated at 50° C. for 12 h in 30 ml of 6 N hydrochloric acid/THF (1:1) and the reaction mixture was allowed to stand overnight at room temperature. The mixture was extracted with dichloromethane and the organic phase was dried over sodium sulfate. After filtration, the solvent was removed in vacuo, and the residue was treated with water and freeze-dried. 440 mg of crude 8.3 were obtained, which was employed in the next synthesis step without further purification.

8d) ((S)-4-(4-Hydroxymethylphenyl)-3-benzyl-4-methyl-2,5-dioxoimidazolidin-1-yl)acetyl-L-aspartyl-L-phenylglycine (8.4)

A solution of 200 mg (0.54 mmol) of crude 8.3, 225 mg (0.54 mmol) of H-Asp(O'Bu)-Phg-(O'Bu)×HCl and 178 mg (0.54 mmol) of TOTU was treated with 185 μl (1.08 mmol) of diisopropylethylamine. After 1 h at room temperature, the solvent was removed in vacuo, the residue was dissolved in ethyl acetate and the ethyl acetate phase was extracted 2× in each case with KHSO$_4$/K$_2$SO$_4$ solution, saturated NaHCO$_3$ solution and saturated sodium chloride solution. After phase separation, the organic phase was dried over sodium sulfate. After filtration, the solvent was removed in vacuo and the residue was purified by chromatography on silica gel using methyl tert-butyl ether/heptane (8:2). After concentration of the product fractions, the residue was dissolved in 5 ml of 90% strength trifluoroacetic acid. After 1 h at room temperature, the trifluoroacetic acid was removed in vacuo and the residue was purified by means of preparative HPLC on RP-18. 44 mg (13%) of 8.4 were obtained after freeze-drying.

ES(+)-MS: 617.2 (M+H)$^+$

Example 9
(S)-3-(((S)-4-(4-Hydroxymethylphenyl)-3-benzyl-4-methyl-2,5-dioxoimidazolidin-1-yl)acetylamino)-2-(1-adamantylmethyloxycarbonylamino)propionic acid

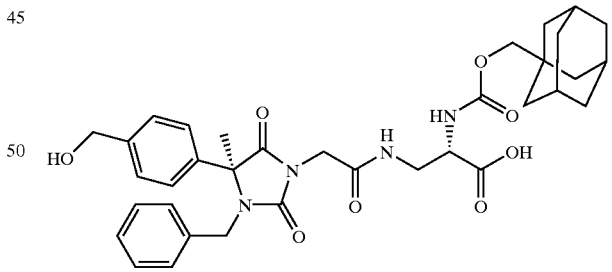

Preparation was carried out analogously to Example 8 by coupling 8.3 to tert-butyl (S)-2-(1-adamantylmethyloxycarbonylamino)-3-aminopropionate (see Example 4) instead of H-Asp(O'Bu)-Phg-(O'Bu)×HCl. After cleavage of the tert-butyl ester using 90% strength trifluoroacetic acid, the crude product was partitioned between water and dichloromethane. The organic phase was separated off, dried over sodium sulfate and, after filtration, the solvent was removed in vacuo. The residue was purified by preparative HPLC on RP-18.

ES(+)-MS: 647.3 (M+H)$^+$

Example 10
((R,S)-4-(4-Hydroxyphenyl)-3-benzyl-4-methyl-2,5-dioxoimidazolidin-1-yl)acetyl-L-aspartyl-L-phenylglycine

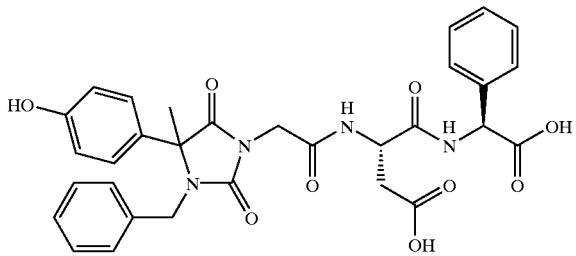

10a) 1-(4-(Tetrahydropyran-2-yloxy)phenyl)ethanone (10.1)

13.62 g (100 mmol) of 4-hydroxyacetophenone and 10.04 ml (110 mmol) of 3,4-dihydro-2H-pyran were suspended in 100 ml of anhydrous methylene chloride. At 0° C., 190 mg (1 mmol) of p-toluenesulfonic acid were added with stirring and the mixture was stirred at 0° C. for 3 hours. 10.04 ml (110 mmol) of 3,4-dihydro-2H-pyran were added again and the mixture was stirred at room temperature for a further 3 hours. The batch was poured into 150 ml of water, the phases were separated and the organic phase was extracted with saturated NaHCO$_3$ solution, saturated NaCl solution and with water. The organic phase was dried over sodium sulfate, concentrated and, for purification, chromatographed on silica gel (70–200 µm) using methylene chloride as an eluent. 13.65 g (62%) of 10.1 were obtained.

10b) (R,S)-4-Methyl-4-(4-(tetrahydropyran-2-yloxy)phenyl)-2,5-dioxoimidazolidine (10.2)

11.01 g (50 mmol) of 10.1 and 42.3 g (440 mmol) of ammonium carbonate were suspended in 200 ml of 50% strength ethanol. 4.23 g (65 mmol) of potassium cyanide were added thereto. The mixture was stirred at 50 to 60° C. for 5 hours. After a short time, a clear solution was formed. The mixture was allowed to stand at room temperature overnight and stirring was then continued at 60° C. for 6 hours. Using 6 N HCl, the pH was adjusted to 6.3 and the mixture was stirred with ice-cooling for 2 h. The precipitate was filtered off with suction, washed with water and dried over phosphorus pentoxide in a desiccator. 9.5 g (65%) of 10.2 were obtained.

10c) Methyl ((R,S)-4-methyl-4-(4-(tetrahydropyran-2-yloxy)phenyl)-2,5-dioxoimidazolidin-1-yl)acetate (10.3)

230 mg (10 mmol) of sodium were dissolved in 25 ml of anhydrous methanol under argon. 2.9 h (10 mmol) of 10.2 were added. The mixture was heated to reflux with stirring for 2 hours. 1.66 g (10 mmol) of potassium iodide were then added and a solution of 0.975 ml (10 mmol) of methyl chloroacetate in 1.1 ml of anhydrous methanol was added dropwise in the course of 15 minutes. The mixture was heated to reflux for 4 hours and then allowed to stand at room temperature overnight. A further 0.195 ml (2 mmol) of methyl chloroacetate in 0.22 ml of anhydrous methanol were added and the batch was stirred under reflux for 4 hours. The precipitate was filtered off with suction and the filtrate was concentrated. The residue was dissolved in methylene chloride, insoluble matter was filtered off and the filtrate was chromatographed on silica gel using methylene chloride/ethyl acetate (9:1). 2.56 g (71%) of 10.3 were obtained.

10d) Methyl ((R,S)-3-benzyl-4-methyl-4-(4-(tetrahydropyran-2-yloxy)-phenyl)-2,5-dioxo-imidazolidin-1-yl) acetate (10.4)

2.53 g (7 mmol) of 10.3 were dissolved in 8.5 ml of anhydrous DMF under argon. At 15° C., 370 mg (7.7 mmol) of sodium hydride (50% strength in oil) were added. The mixture was stirred at 15° C. for 15 minutes and 0.91 ml (7.7 mmol) of benzyl bromide was then added dropwise. The mixture was stirred at room temperature for 7.5 hours and allowed to stand at room temperature overnight. The clear solution was concentrated in vacuo and the residue was partitioned between ethyl acetate and water. The organic phase was separated off and the aqueous phase was washed again with ethyl acetate. The organic phases were combined, washed with water, dried over sodium sulfate and concentrated. The residue was chromatographed on silica gel using methylene chloride/ethyl acetate (9.5:0.5). 1.59 g (50%) of 10.4 were obtained.

10e) ((R,S)-4-(4-Hydroxyphenyl)-3-benzyl-4-methyl-2,5-dioxoimidazolidin-1-yl)acetic acid (10.5)

1.53 g (3.5 mmol) of 10.4 were heated under reflux for 3 h with 30 ml of concentrated hydrochloric acid. After concentration of the solution in vacuo, the residue was triturated with water, cooled overnight and then filtered off with suction. It was dried over phosphorus pentoxide in a desiccator and 1.22 g (98%) of 10.5 were obtained.

10f) ((R,S)-4-(4-Hydroxyphenyl)-3-benzyl-4-methyl-2,5-dioxoimidazolidin-1-yl)acetyl-L-aspartyl-L-phenylglycine di-tert-butyl ester (10.6)

354 mg (1 mmol) of 10.5, 415 mg (1 mmol) of H-Asp (O'Bu)-Phg-O'Bu×HCl and 135 mg (1 mmol) of HOBt were dissolved in 10 ml of DMF. At 0° C., 0.13 ml (1 mmol) of N-ethylmorpholine and 220 mg (1 mmol) of DCC were added. The mixture was stirred at 0° C. for 1 hour and at room temperature for 3 hours and allowed to stand at room temperature overnight. The solid was filtered off with suction and the filtrate was concentrated in vacuo. The residue was dissolved in ethyl acetate and washed with NaHCO$_3$ solution, K$_2$SO$_4$/KHSO$_4$ solution and saturated sodium chloride solution. After drying over sodium sulfate, the drying agent was filtered off and the filtrate was concentrated in vacuo. The oily residue was triturated with diethyl ether and the organic phase was concentrated. 730 mg (100%) of 10.6 were obtained.

10g) ((R,S)-4-(4-Hydroxyphenyl)-3-benzyl-4-methyl-2,5-dioxoimidazolidin-1-yl)acetyl-L-aspartyl-L-phenylglycine (10.7)

370 mg (0.52 mmol) of 10.6 were dissolved in 4 ml of 90% strength trifluoroacetic acid and allowed to stand at room temperature for 1 hour. The mixture was then concentrated. The residue was triturated with diethyl ether and filtered off with suction. 202 mg (64% ) of 10.7 were obtained.

The aspartylphenylglycine derivatives of Examples 12 to 126 were prepared by solid-phase synthesis according to the general procedure indicated in Example 11.

Example 11
General Procedure for the Preparation of Aspartylphenylglycine Derivatives by Solid-phase Synthesis General The syntheses on the polymeric support were carried out according to the synthesis sequence which is shown in scheme 1. The radicals $R^{50}$ to $R^{55}$ in scheme 1 have the meaning of the radicals which are located in the corresponding position in the molecule in formula I, or they can contain functional groups in protected form or in the form of precursors. $R^{50}$ corresponds to the radical R. $R^{51}$ corresponds to the radicals $R^4$ and $R^{15}$, where functional groups present in these radicals can be present in protected form or in the form of precursors (the radical —NHR$^{51}$ can thus be, for example, the radical of an amino acid which is formally obtained by removal of a hydrogen atom from the amino group). $R^{52}$, together with the CH group to which this radical is bonded, corresponds to the group B ($R^{52}$ thus corresponds to a substituent on a methylene group representing B). $R^{53}$ corresponds to $R^{13}$. $R^{54}$ corresponds to the group $R^1$—A, where functional groups present therein can be present in protected form or in the form of precursors. $R^{55}$ corresponds to the group $R^0$.

The synthesis of intermediates on a relatively large scale was carried out in special reaction vessels with frits inserted in the bottom of the reaction vessel; the synthesis of the compounds of the formula I was carried out in syringes or reaction blocks (Act 496, MultiSynTech). The syntheses on the resin were monitored by on-bead analysis (FT-IR with ATR unit and MAS-NMR) and cleavage of an analytical sample from the resin (HPLC, MS, NMR).

Preparation of the Aspartic Acid Building Block FmocAsp(OH)Oallyl

FmocAsp(OtBu)Oallyl (40 g, 88.7 mmol) was treated with 25 ml of trifluoroacetic acid and the mixture was stirred at room temperature for 30 min. The solvent was stripped off on a rotary evaporator. The residue was dried in vacuo. FmocAsp(OH)Oallyl was obtained as a yellow oil (33.9 g, 97%).

ES(+)-MS: 395.2 (M+H)$^+$

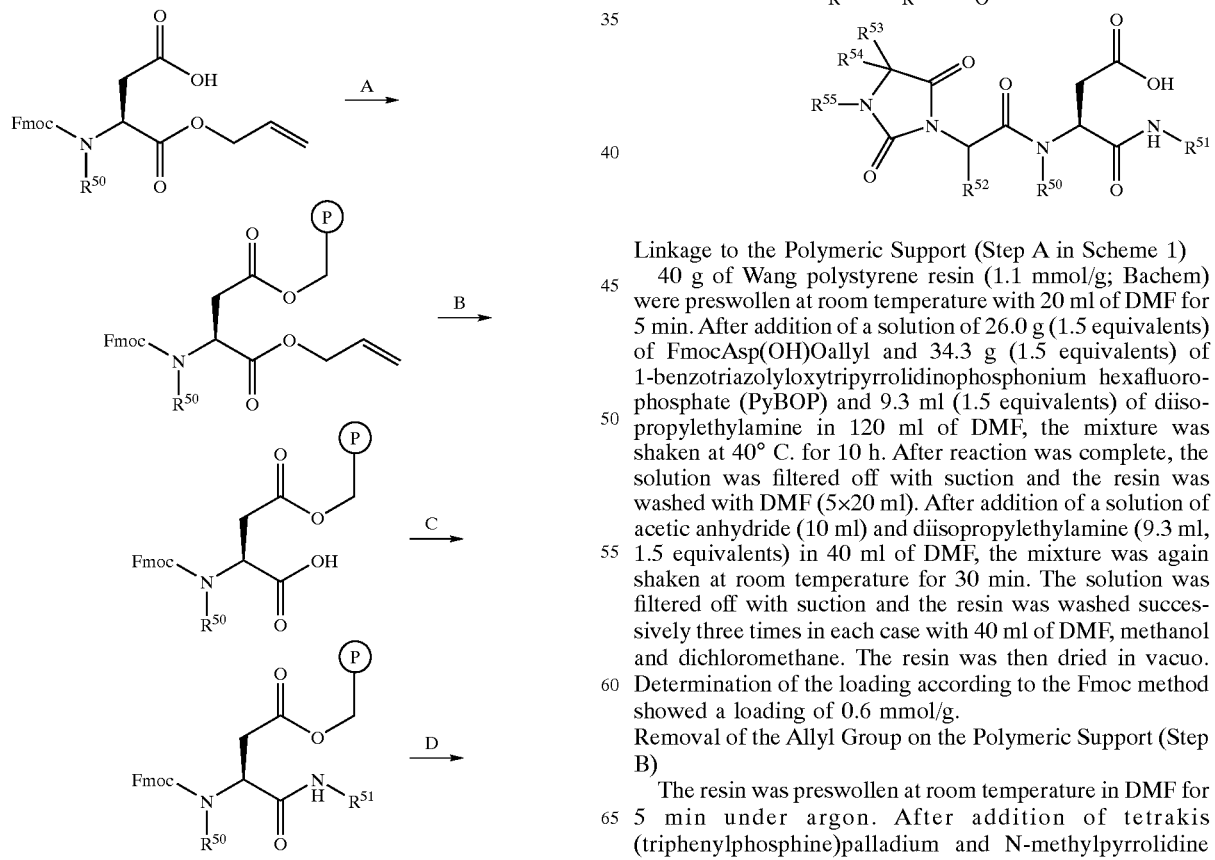

Linkage to the Polymeric Support (Step A in Scheme 1)

40 g of Wang polystyrene resin (1.1 mmol/g; Bachem) were preswollen at room temperature with 20 ml of DMF for 5 min. After addition of a solution of 26.0 g (1.5 equivalents) of FmocAsp(OH)Oallyl and 34.3 g (1.5 equivalents) of 1-benzotriazolyloxytripyrrolidinophosphonium hexafluorophosphate (PyBOP) and 9.3 ml (1.5 equivalents) of diisopropylethylamine in 120 ml of DMF, the mixture was shaken at 40° C. for 10 h. After reaction was complete, the solution was filtered off with suction and the resin was washed with DMF (5×20 ml). After addition of a solution of acetic anhydride (10 ml) and diisopropylethylamine (9.3 ml, 1.5 equivalents) in 40 ml of DMF, the mixture was again shaken at room temperature for 30 min. The solution was filtered off with suction and the resin was washed successively three times in each case with 40 ml of DMF, methanol and dichloromethane. The resin was then dried in vacuo. Determination of the loading according to the Fmoc method showed a loading of 0.6 mmol/g.

Removal of the Allyl Group on the Polymeric Support (Step B)

The resin was preswollen at room temperature in DMF for 5 min under argon. After addition of tetrakis(triphenylphosphine)palladium and N-methylpyrrolidine (10 equivalents), the mixture was shaken at 40° C. for 6 h under argon. After reaction was complete, the solution was filtered off with suction and the resin was washed successively three times in each case with DMF, methanol, toluene and dichloromethane and then dried.

Coupling with Amino Compounds on the Polymeric Support (Step C)

The loaded resin with free carboxyl function was preswollen at room temperature in DMF for 5 min. After addition of a solution of HOBt (1.2 equivalents), TOTU (1.2 equivalents) and diisopropylethylamine (1.2 equivalents) in DMF, the mixture was shaken at room temperature for 30 min. The amino compound (1.2 equivalents) was added dissolved in DMF. The suspension was shaken at room temperature until reaction was complete (HPLC checking). After reaction was complete, the solution was filtered off with suction and the resin was washed successively three times in each case with DMF, methanol, toluene and dichloromethane and then dried.

Removal of the Fmoc Protective Group (Step D)

For the removal of the Fmoc protective group, the resin was preswollen at room temperature in DMF for 5 min. After addition of a solution of DMF/piperidine (1:1), it was shaken at room temperature for 20 min. The solution was filtered off with suction and the process was repeated. The removal of an analytical sample showed complete reaction according to HPLC/MS investigation. After reaction was complete, the resin was washed three times with dichloromethane and employed directly in the coupling.

Coupling to α-Halocarboxylic Acids (Step E)

a) Coupling with DIC

The symmetrical anhydrides were formed from α-halocarboxylic acids (5 equivalents) by reaction with diisopropylcarbodiimide (2.4 equivalents) in dichloromethane for 30 minutes. After this time, 2 equivalents of diisopropylethylamine were added. The mixture was added to the resin and shaken at room temperature for 12 h. After reaction was complete, the solution was filtered off with suction and the resin was washed successively three times in each case with DMF, toluene and dichloromethane and then immediately reacted further.

b) Coupling with Acid Halides

The resin was preswollen at room temperature with dichloromethane for 5 min. The α-halocarboxylic acid halides (1.5 equivalents) were added dissolved in dichloromethane. After addition of a catalytic amount of 4-dimethylaminopyridine and diisopropylethylamine (1 equivalent), the mixture was shaken at room temperature for 8 h. After reaction was complete, the solution was filtered off with suction and the resin was washed successively three times in each case with DMF, toluene and dichloromethane and then immediately reacted further.

Coupling of the α-haloacyl Compounds to Hydantoins (Step F)

The 4,4-disubstituted hydantoins (2 equivalents) were activated at room temperature with diazabicycloundecene (DBU) (2 equivalents) in DMF. The activated solution was added after 15 min to the resin preswollen in DMF for 5 min. The mixture was shaken at room temperature for 8 h. After reaction was complete, the solution was filtered off with suction and the resin was washed successively three times in each case with DMF, methanol, toluene and dichloromethane and then dried.

N-Alkylation of the Hydantoin on the Polymeric Support (Step G)

a) Alkylation with Cesium Carbonate

The resin was preswollen at room temperature in DMF for 5 min. After addition of cesium carbonate (3 equivalents), it was shaken at room temperature for 30 min After addition of the alkylating agent (bromide or iodide), it was shaken at 50° C. for 6 h. After reaction was complete, the solution was filtered off with suction and the resin was washed successively three times in each case with DMF, methanol/water/ DMF (1.5:1.5:7), DMF, toluene and dichloromethane and then dried.

b) Alkylation with Phosphazenes

The resin was preswollen at room temperature in DMF for 5 min. After addition of N'''-tert-butyl-N,N,N',N',N'',N''-hexamethylphosphorimidic triamide (phosphazene base P1-t-Bu) (3 equivalents), it was shaken at room temperature for 30 min. After addition of the alkylating agent (bromide or iodide), it was shaken at room temperature for 4 h. After reaction was complete, the solution was filtered off with suction and the resin was washed successively three times in each case with DMF, toluene and dichloromethane and then dried.

Removal from the Resin (Step H)

For the removal of the compound from the resin, a mixture of trifluoroacetic acid/dichloromethane (1:1) was added to the resin. The suspension was shaken for 1 h. The resin was filtered off. The remaining solution was concentrated in vacuo. The residue was purified by silica gel chromatography (dichloromethane and ethyl acetate).

The compounds of Examples 12 to 126, which have the structure indicated in the formula Ib, were prepared according to the general method described in Example 11. The meanings of the radicals in the individual compounds are indicated in Tables 1 and 2.

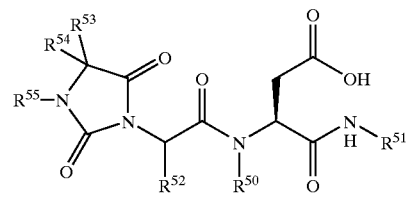

Ib

In Tables 1 and 2, the abbreviations have the following meanings:

| | |
|---|---|
| Bn= Benzyl | 3-BrBn= 3-Bromobenzyl |
| 4-BrBn= 4-Bromobenzyl | 4-ClBn= 4-Chlorobenzyl |
| 4-Bip= 4-Biphenylylmethyl | 2-Py= 2-Pyridylmethyl |
| 3-Py = 3-Pyridylmethyl | 4-Py= 4-Pyridylmethyl |
| H= Hydrogen | Me= Methyl |
| Et= Ethyl | nPr= n-Propyl |
| iPr= Isopropyl | nBu= n-Butyl |
| iBu= Isobutyl | nPe= n-Pentyl |
| nHe= n-Hexyl | All= Allyl |
| Ph= Phenyl | |

The following abbreviations represent radicals which represent the group —NH—$R^{51}$ in the formula Ib. They are radicals of amino acids or derivatives thereof which are formally obtained by abstraction of a hydrogen atom from the amino group of the amino acid.

Val = L-Valyl 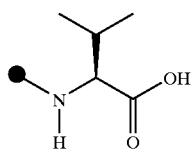

Ala = L-Alanyl 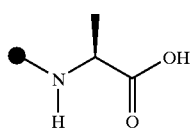

Ile = L-Isoleucyl 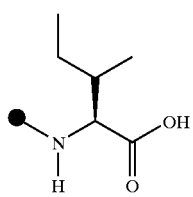

Phg = L-Phenylglycyl 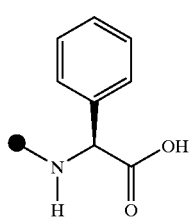

PhgMor = L-Phenylglycyl morpholide 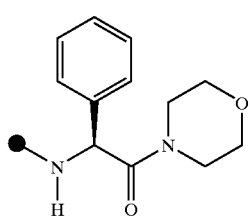

PhgPip = L-Phenylglycyl piperidide 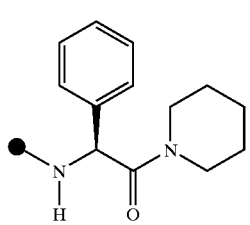

PheMor = L-Phenylalanyl morpholide 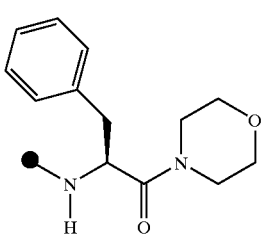

-continued

PhePip = L-Phenylalanyl piperidide 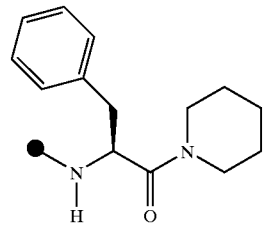

TABLE 1

| Example | $R^{50}$ | —NH—$R^{51}$ | $R^{52}$ | $R^{53}$ | $R^{54}$ | $R^{55}$ | ES(+)-MS |
|---|---|---|---|---|---|---|---|
| 12 | Me | Val | Bn | Me | Ph | Bn | 659 |
| 13 | Me | Val | iPr | Me | Ph | 4-Bip | 686 |
| 14 | Me | Val | H | Me | Ph | Bn | 568 |
| 15 | H | Phg | H | Me | Ph | 2-Py | 589 |
| 16 | H | Phg | H | Me | Ph | 3-Py | 589 |
| 17 | H | Phg | H | Me | Ph | 4-Py | 589 |
| 18 | H | Phg | Et | Me | Ph | Bn | 617 |
| 19 | H | Phg | H | Ph | Ph | Bn | 651 |
| 20 | H | Phg | nBu | Me | Ph | Bn | 644 |
| 21 | H | Phg | iBu | Me | Ph | Bn | 644 |
| 22 | H | Phg | nBu | Me | Ph | 2-Py | 645 |
| 23 | H | Phg | nBu | Me | Ph | 3-Py | 645 |
| 24 | H | Phg | nBu | Me | Ph | 4-Py | 645 |
| 25 | H | Phg | iBu | Me | Ph | 2-Py | 645 |
| 26 | H | Phg | iBu | Me | Ph | 3-Py | 645 |
| 27 | H | Phg | iBu | Me | Ph | 4-Py | 645 |
| 28 | H | Ile | H | Me | Ph | 4-BrBn | 647 |
| 29 | H | Ile | Bn | Me | Ph | Bn | 659 |
| 30 | H | Ile | iPr | Me | Ph | Bn | 610 |
| 31 | H | Ile | iPr | Me | Ph | 4-Bip | 686 |
| 32 | H | Ile | H | Me | Ph | Bn | 568 |
| 33 | H | Ile | nPe | Me | Ph | Bn | 639 |
| 34 | H | Ile | nPe | Me | Ph | 4-Bip | 715 |
| 35 | H | Ala | Bn | Me | Ph | Bn | 616 |
| 36 | H | Ala | iPr | Me | Ph | Bn | 568 |
| 37 | H | Ala | iPr | Me | Ph | 4-Bip | 644 |
| 38 | H | Ala | H | Me | Ph | Bn | 525 |
| 39 | H | Ala | nPe | Me | Ph | Bn | 596 |
| 40 | H | Ala | nPe | Me | Ph | 4-Bip | 672 |
| 41 | H | Phg | Bn | Me | Ph | Bn | 679 |
| 42 | H | Phg | iPr | Me | Ph | Bn | 630 |
| 43 | H | Phg | iPr | Me | Ph | 4-Bip | 707 |
| 44 | H | Phg | H | Me | Ph | Bn | 588 |
| 45 | H | Phg | nPe | Me | Ph | Bn | 658 |
| 46 | H | Phg | nPe | Me | Ph | 4-Bip | 735 |
| 47 | H | Phg | Et | Me | Ph | 2-Py | 618 |
| 48 | H | Phg | Et | Me | Ph | 3-Py | 618 |
| 49 | H | Phg | Et | Me | Ph | 4-Py | 618 |
| 50 | H | Phg | H | Ph | Ph | 2-Py | 651 |

TABLE 1-continued

| Example | R⁵⁰ | —NH—R⁵¹ | R⁵² | R⁵³ | R⁵⁴ | R⁵⁵ | ES(+)-MS |
|---|---|---|---|---|---|---|---|
| 51 | H | Phg | H | Me | Ph | 3-Py | 651 |
| 52 | H | Phg | H | Me | Ph | 4-Py | 651 |
| 53 | Me | Val | nPe | Me | Ph | Bn | 638 |
| 54 | Me | Val | nPe | Me | Ph | 4-Bip | 715 |
| 55 | H | Val | H | Me | Ph | Bn | 554 |
| 56 | H | Val | Bn | Me | Ph | Bn | 644 |
| 57 | H | Val | iPr | Me | Ph | 4-Bip | 672 |
| 58 | H | Val | iPr | Me | Ph | Bn | 596 |
| 59 | H | Val | nPe | Me | Ph | Bn | 624 |
| 60 | H | Val | nPe | Me | Ph | 4-Bip | 701 |
| 61 | H | PheMor | H | Me | Ph | Bn | 671 |
| 62 | H | PheMor | Bn | Me | Ph | Bn | 762 |
| 63 | H | PheMor | iPr | Me | Ph | 4-Bip | 790 |
| 64 | H | PheMor | iPr | Me | Ph | Bn | 714 |
| 65 | H | PheMor | nPe | Me | Ph | Bn | 742 |
| 66 | H | PheMor | nPe | Me | Ph | 4-Bip | 818 |
| 67 | H | PhePip | H | Me | Ph | Bn | 670 |
| 68 | H | PhePip | Bn | Me | Ph | Bn | 760 |
| 69 | H | PhePip | iPr | Me | Ph | 4-Bip | 788 |
| 70 | H | PhePip | nBu | Me | Ph | Bn | 712 |
| 71 | H | PhePip | nPe | Me | Ph | Bn | 726 |
| 72 | H | PhePip | nBu | Me | Ph | 4-Bip | 802 |
| 73 | H | PhgMor | H | Me | Ph | Bn | 658 |
| 74 | H | PhgMor | Bn | Me | Ph | Bn | 748 |
| 75 | H | PhgMor | iPr | Me | Ph | Bn | 700 |
| 76 | H | PhgMor | nPe | Me | Ph | Bn | 728 |
| 77 | H | PhgMor | nPe | Me | Ph | 4-Bip | 804 |
| 78 | H | PhgPip | H | Me | Ph | Bn | 656 |
| 79 | H | PhgPip | Bn | Me | Ph | Bn | 746 |
| 80 | H | PhgPip | iPr | Me | Ph | 4-Bip | 774 |
| 81 | H | PhgPip | iPr | Me | Ph | Bn | 698 |
| 82 | H | PhgPip | nPe | Me | Ph | Bn | 726 |
| 83 | H | PhgPip | nPe | Me | Ph | 4-Bip | 802 |
| 84 | H | Phg | 4-ClBn | Me | Ph | Bn | 713 |
| 85 | H | Phg | All | Me | Ph | Bn | 629 |
| 86 | H | Phg | H | Me | Ph | 4-BrBn | 667 |
| 87 | H | Phg | H | Me | Ph | 3-BrBn | 667 |
| 88 | H | Ph(CH₂)₃NH— | nBu | Me | Ph | Bn | 628 |
| 89 | H | Phg | nBu | Me | Ph | nPr | 595 |
| 90 | H | Phg | nBu | Me | Ph | iBu | 610 |
| 91 | H | Phg | nBu | Me | Ph | nHe | 638 |
| 92 | H | Phg | nPr | Me | Ph | Bn | 630 |
| 93 | H | Phg | nHe | Me | Ph | Bn | 672 |
| 94 | H | Phg | H | Me | Ph | nPr | 539 |
| 95 | H | PheMor | H | Me | Ph | nPr | 622 |
| 96 | H | PheMor | iBu | Me | Ph | Bn | 727 |
| 97 | H | Phg | H | Me | Ph | Et | 525 |
| 98 | H | Phg | H | Me | Ph | iBu | 553 |
| 99 | H | Phg | H | Me | Ph | iPr | 539 |
| 100 | H | Phg | nBu | Me | Ph | Bn | 644 |
| 101 | H | CH₃(CH₂)₇NH— | nBu | Me | Ph | Bn | 621 |
| 102 | H | Phg | Et | Me | Ph | iPr | 567 |
| 103 | H | Phg | nPr | Me | Ph | Bn | 630 |
| 104 | H | Phg | nPr | Me | Ph | iBu | 595 |
| 105 | H | Phg | nPr | Me | Ph | iPr | 581 |

TABLE 2

In all compounds of Table 2, the radical R⁵⁰ in formula Ib is hydrogen, the radical —NH—R⁵¹ is Phg (= L-phenylglycyl) and the radical R⁵² is n-butyl.

| Example | R⁵³ | R⁵⁴ | R⁵⁵ | ES(+)-MS |
|---|---|---|---|---|
| 106 | Me | 2-Fluorophenyl | Bn | 661 |
| 107 | Me | 3-Fluorophenyl | Bn | 661 |
| 108 | Me | 4-Fluorophenyl | Bn | |
| 109 | Me | 4-Fluorobenzyl | Bn | |
| 110 | Me | 3-Trifluoromethylphenyl | Bn | |
| 111 | Me | 3-Chlorophenyl | Bn | |
| 112 | Bn | Bn | Bn | |
| 113 | Me | 4-Methoxybenzyl | Bn | |
| 114 | Me | Cyclohexyl | Bn | |
| 115 | Me | Bn | Bn | |
| 116 | Me | 2-Thienyl | Bn | |
| 117 | Me | 3-Trifluoromethylbenzyl | Bn | |
| 118 | Cyclopropyl | Ph | Bn | |
| 119 | Cyclobutyl | Ph | Bn | |
| 120 | Me | 3,4,5-Trimethoxyphenyl | Bn | |
| 121 | Me | 4-Fluorophenyl | H | |
| 122 | Bn | Bn | H | |
| 123 | Me | 4-Methoxybenzyl | H | |
| 124 | Me | 3-Trifluoromethylbenzyl | H | |
| 125 | Cyclobutyl | Ph | H | |
| 126 | Me | 3,4,5-Trimethoxybenzyl | H | |

Example 127

(2-((R,S)-4-Phenyl-3-benzyl-4-methyl-2,5-dioxoimidazolidin-1-yl)-2,2-dimethylacetyl)-L-aspartyl-L-phenylglycine

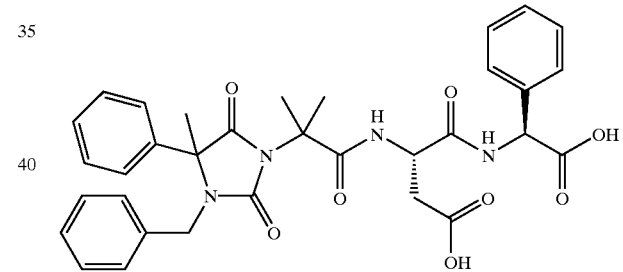

The compound was prepared by solid-phase synthesis analogously to the general procedure described in Example 11.

ES(+)-MS: 616

The 2,3-diaminopropionic acid derivatives of Examples 129 to 168 were prepared by solid-phase synthesis according to the general procedure indicated in Example 128.

Example 128

General Procedure for the Preparation of Diaminopropionic Acid Derivatives by Solid-phase Synthesis General The syntheses on the polymeric support were carried out according to the synthesis sequence which is shown in Scheme 2. The above general explanations for the preparation of aspartylphenylglycine derivatives by solid-phase synthesis apply here correspondingly.

Coupling of the α-Fmoc-β-Alloc-2,3-diaminopropionic acid to the Polymeric Support (Step J in Scheme 2)

A solution of 0.243 g (1.8 mmol) of HOBt, 0.590 g (1.8 mmol) of TOTU, 0.25 ml (1.8 mmol) of diisopropylethylamine and 0.738 g (1.8 mmol) of (S)-α-Fmoc-β-Alloc-2, 3-diaminopropionic acid in 5 ml of DMF was added to 1 g of Wang polystyrene resin and the mixture was shaken at room temperature for 12 h. The resin was filtered off and washed 3 times with 10 ml of DMF each time, once with 10 ml of toluene, once with 10 ml of methanol and 3 times with 10 ml of dichloromethane. Determination of the loading according to the FMOC method showed a loading of 0.9 mmol/g.

Removal of the allyloxycarbonyl group on the polymeric support (step K) The resin was preswollen at room temperature in DMF for 5 min under argon. After addition of tetrakis(triphenylphosphine)palladium and N-methylpyrrolidine (10 equivalents), the mixture was shaken at 40° C. for 6 h under argon. After reaction was complete, the solution was filtered off with suction and the resin was washed successively three times in each case with DMF, methanol, toluene and dichloromethane and then dried.

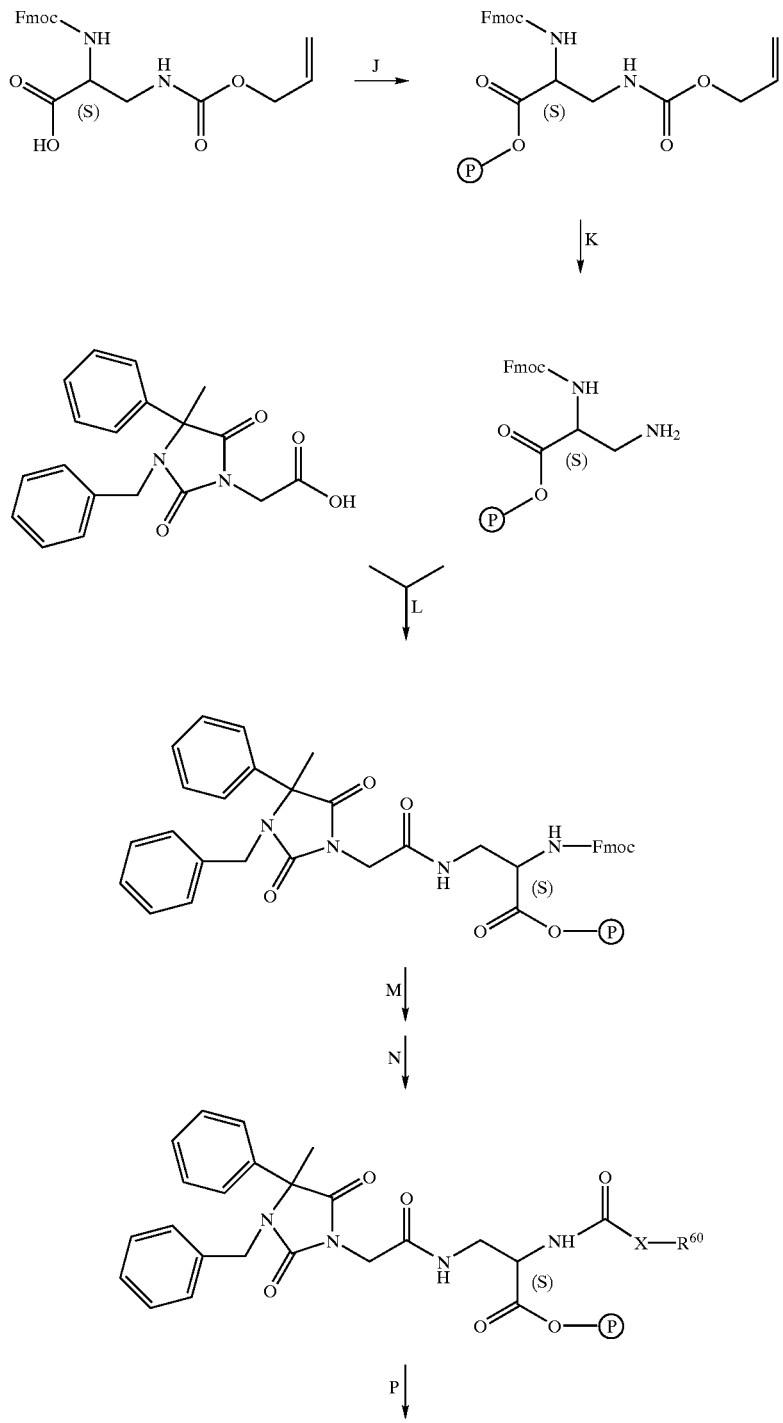

Scheme 2

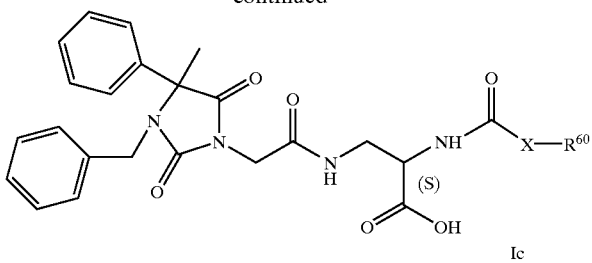

Ic

Coupling of the α-Fmoc-2,3-diaminopropionic Acid with Hydantoin-carboxylic Acids (Step L)

A solution of 36 mg (0.27 mmol) of HOBt, 88 mg (0.27 mmol) of TOTU, 37 μl (0.27 mmol) of diisopropylethylamine and 0.27 mmol of (R,S)-3-benzyl-4-phenyl-4-methyl-2,5-dioxoimidazolidin-1-ylacetic acid in 5 ml of DMF was added to 100 mg of resin which was loaded with the α-Fmoc-2,3-diaminopropionic acid (0.9 mmol/g) and the mixture was shaken at room temperature for 12 h. The resin was filtered off and washed 3 times with 10 ml of DMF each time, once with 10 ml of toluene, once with 10 ml of methanol and 3 times with 10 ml of dichloromethane.

Removal of the Fmoc Protective Group (Step M)

For the removal of the Fmoc protective group, the resin was preswollen at room temperature in DMF for 5 min. After addition of a solution of DMF/piperidine (1:1), it was shaken at room temperature for 20 min. The solution was filtered off with suction and the process was repeated. The cleavage of an analytical sample showed complete reaction according to HPLC/MS investigation. After complete reaction, the resin was washed three times with dichloromethane and directly employed in the next step.

Acylation of the α-amino Group of the 2,3-diaminopropionic Acid (Step N)

a) Preparation of Carboxamides (Acylation with Carboxylic Acids)

A solution of 36 mg (0.27 mmol) of HOBt, 88 mg (0.27 mmol) of TOTU, 37 μl (0.27 mmol) of diisopropylethylamine and 0.27 mmol of the corresponding carboxylic acid of the formula $R^{60}$—COOH in 5 ml of DMF was added to 100 mg of resin which was loaded with the 2,3-diaminopropionic acid building block and the mixture was shaken at room temperature for 12 h. The resin was filtered off and washed 3 times with 10 ml of DMF each time, once with 10 ml of toluene, once with 10 ml of methanol and 3 times with 10 ml of dichloromethane.

b) Preparation of Ureas (Acylation with Isocyanates)

A solution of (0.27 mmol of the corresponding isocyanate of the formula $R^{60}$—N=C=O and of a catalytic amount (1 mg) of 4-dimethylaminopyridine in 5 ml of DMF were added to 100 mg of resin which was loaded with the 2,3-diaminopropionic acid building block and the mixture was shaken at room temperature for 8 h. The resin was filtered off and washed 3 times with 10 ml of DMF each time, once with 10 ml of toluene, once with 10 ml of methanol and 3 times with 10 ml of dichloromethane.

c) Preparation of Carbamates (Acylation with Carbonic Acid Derivatives)

The corresponding alcohol (0.27 mmol) of the formula $R^{60}$—OH was shaken at 40° C. with equivalent amounts in each case of di(N-succinimidyl) carbonate and diisopropylethylamine for 5 h. The solution was added to 100 mg of resin which was loaded with the 2,3-diaminopropionic acid building block and the mixture was shaken at room temperature for 8 h. The resin was filtered off and washed 3 times with 10 ml of DMF each time, once with 10 ml of toluene, once with 10 ml of methanol and 3 times with 10 ml of dichloromethane Removal from the Resin (Step P)

For the removal of the compound from the resin, a mixture of trifluoroacetic acid and dichloromethane (1:1) was added to the resin. The suspension was shaken for 1 h and the resin was then filtered off. The remaining solution was concentrated in vacuo. The residue was purified by chromatography on silica gel (dichloromethane and ethyl acetate).

The 3-benzyl-4-phenyl-4-methyl-2,5-dioxoimidazolidin-1-yl-acetic acid employed in Step L was obtained according to the following general working procedure for the preparation of 4,4-disubstituted hydantoincarboxylic acids.

A solution of 288 mg of potassium cyanide in 3.8 ml of water was added by pipette to 3.0 mmol of acetophenone and 3.0 g of ammonium carbonate in 3.8 ml of ethanol. The mixture was stirred at 55° C. for 5 h. 8 ml of 6 N hydrochloric acid were then slowly metered in and the mixture was stirred at 55° C. for a further 2 h. After addition of 6.0 ml of water, the mixture was cooled to room temperature over 2 h. The product was filtered off with suction, washed with water and dried in the air.

The (R,S)-4-methyl-4-phenylhydantoin was suspended in DMF (20 ml/g of hydantoin derivative) with one equivalent of cesium carbonate and the mixture was stirred at room temperature for 20 min. After addition of one equivalent of tert-butyl bromoacetate, the mixture was stirred at room temperature for 1 h. It was then treated with water and extracted with ethyl acetate. The combined organic phases were dried over magnesium sulfate, filtered and concentrated. The hydantoinacetic acid ester was obtained as an oil.

The hydantoinacetic acid ester was suspended in DMF (20 ml/g of hydantoin derivative) with one equivalent of cesium carbonate and one equivalent of benzyl bromide The mixture was stirred at room temperature for 1 h. It was then treated with water and extracted with ethyl acetate. The combined organic phases were dried over magnesium sulfate, filtered and concentrated. The residue was purified by chromatography on silica gel (hexane/ethyl acetate). The 3-benzylhydantoinacetic acid ester was obtained as an oil. The tert-butyl ester group was then cleaved to give the carboxylic acid under standard conditions using trifluoroacetic acid.

According to the general procedure described in Example 128, the compounds of Examples 129 to 168 which have the structure indicated in the formula Ic were prepared. The meaning of the groups X and $R^{60}$ in the individual compounds of the formula Ic are indicated in Table 3. If X is a direct bond, this means that the group $R^{60}$ is directly bonded to the carbonyl group a group $R^{60}$—CO thus being present.

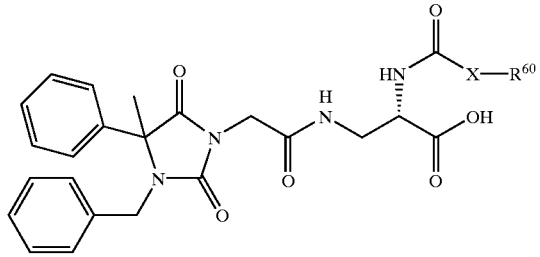

Ic

TABLE 3

| Example | —X— | $R^{60}$ | ES-(+)-MS |
|---|---|---|---|
| 129 | direct bond | 3-Methylphenyl | 543 |
| 130 | direct bond | 2-Methylphenyl | 543 |
| 131 | direct bond | 2,4-Dimethoxyphenyl | 589 |
| 132 | direct bond | 3,5-Dinitrophenyl | 619 |
| 133 | direct bond | 4-tert-Butylphenyl | 585 |
| 134 | direct bond | 2,4,5-Trimethylphenyl | 571 |
| 135 | —NH— | 4-Chlorophenyl | 579 |
| 136 | —NH— | 4-Isopropylphenyl | 586 |
| 137 | —NH— | 2-Nitrophenyl | 589 |
| 138 | direct bond | 4-Chlorophenyl | 564 |
| 139 | direct bond | 4-Methylphenyl | 543 |
| 140 | direct bond | 4-Methoxyphenyl | 559 |
| 141 | direct bond | 4-Nitrophenyl | 574 |
| 142 | —NH— | 4-(Trifluoromethoxy)phenyl | 628 |
| 143 | —NH— | 2-Methoxyphenyl | 574 |
| 144 | —NH— | 3,5-Bis(trifluoromethyl)phenyl | 680 |
| 145 | —NH— | Benzyl | 558 |
| 146 | —O— | 2-Methoxyethyl | 527 |
| 147 | —O— | Prop-2-ynyl | 507 |
| 148 | —O— | 2,2,2-Trifluoroethyl | 551 |
| 149 | —O— | Cyclopentyl | 537 |
| 150 | —O— | 2-Cyclohexylethyl | 580 |
| 151 | —O— | Prop-2-enyl | 510 |
| 152 | —O— | 2-(4-Fluorophenyl)ethyl | 591 |
| 153 | —O— | 2-(4-Nitrophenyl)ethyl | 618 |
| 154 | —O— | 2-(3-Methoxyphenyl)ethyl | 604 |
| 155 | —O— | Cyclopropylmethyl | 523 |
| 156 | —O— | Isobutyl | 525 |
| 157 | —O— | 2,2-Dimethylpropyl | 539 |
| 158 | —O— | Cyclobutylmethyl | 537 |
| 159 | —O— | 2-Ethylbutyl | 553 |
| 160 | —O— | Cyclopentylmethyl | 551 |
| 161 | —O— | 2-(4-Methylphenyl)ethyl | 589 |
| 162 | —O— | 4-Benzylbenzyl | 650 |
| 163 | —O— | 4-Nitrobenzyl | 604 |
| 164 | —O— | 2-Phenylethyl | 573 |
| 165 | —O— | 2-(4-Methoxyphenyl)ethyl | 604 |
| 166 | —O— | 2-(1-Naphthyl)ethyl | 624 |
| 167 | —O— | 2-(2-Naphthyl)ethyl | 624 |
| 168 | —O— | 2-(4-tert-Butylphenyl)ethyl | 630 |

Example 169
(S)-3-((S)-2-((S)-4-Phenyl-3-benzyl-4-methyl-2,5-dioxoimidazolidin-1-yl)-2-(2-methylpropyl)acetylamino)-3-(3,4-methylenedioxyphenyl)propionic acid

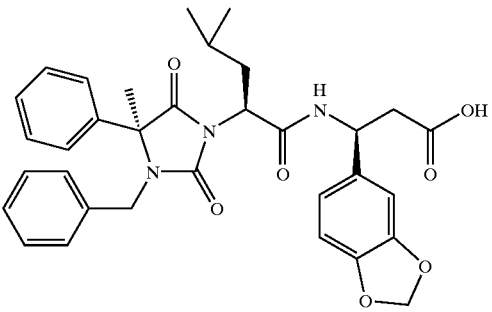

169a) Methyl (S)-2-amino-2-(4-bromophenyl)propionate (169.1)

15 g (55.7 mmol) of (S)-4-(4-bromophenyl)-4 methyl-2,5-dioxoimidazolidine were suspended in 107 ml of 3 N sodium hydroxide solution and the suspension was heated in an autoclave at 145° C. for 2 h. It was allowed to cool to room temperature, the precipitate was filtered off and dissolved in water, and the solution was adjusted to pH 1 using 1 N hydrochloric acid. After freeze-drying, the solid was suspended in 150 ml of absolute methanol. The suspension was cooled to −15° C. and treated with 8.8 ml of thionyl chloride. After stirring at room temperature for 6 h and allowing to stand overnight, a further 100 ml of absolute methanol and 8.8 ml of thionyl chloride were added. The mixture was stirred at room temperature for 8 h and again allowed to stand overnight. After removal of volatile components in vacuo, the residue was adjusted to pH 9.3 using sodium hydrogen carbonate solution and sodium carbonate solution and then the aqueous phase was extracted 2× with ethyl acetate. After drying over sodium sulfate, filtration and removal of the solvent in vacuo, 11.4 g (79%) of 169.1 were obtained.

169b) tert-Butyl (S)-2-((S)-4-(4-bromophenyl)-4-methyl-2,5-dioxoimidazolidin-1-yl)-2-(2-methylpropyl)acetate (169.2)

4.8 g of L-leucine tert-butyl ester isocyanate (prepared from L-leucine tert-butyl ester analogously to J. S. Nowick et al., J. Org. Chem. 1996, 61, 3929) were added to a solution of 5.8 g (22.5 mmol) of 169.1 in 50 ml of DMF. After stirring at room temperature for 4 h, the solvent was removed and the residue was chromatographed on silica gel using heptane/tert-butyl methyl ether=6/4. The fractions containing the intermediate were combined, the solvent was removed in vacuo, the residue was dissolved again in 90 ml of absolute DMF and the solution was treated at 0° C. with 775 mg of a 55–65% strength sodium hydride dispersion in oil. After stirring at room temperature for 3 h, the solvent was removed in vacuo and the residue was chromatographed on silica gel using heptane/tert-butyl methyl ether=1/1. After concentration of the product fractions, 7.8 g (79%) of 169.2 were obtained as a colorless solid.

169c) tert-Butyl (S)-2-((S)-4-(4-bromophenyl)-3-benzyl-4-methyl-2,5-dioxoimidazolidin-1-yl)-2-(2-methylpropyl) acetate (169.3)

540 µl (4.4 mmol) of benzyl bromide and then, at 0° C., 140 mg of a 55–65% strength sodium hydride dispersion in oil were added to a solution of 1.75 g (4 mmol) of 169.2 in 20 ml of absolute DMF and the mixture was stirred at 0° C. for 15 min and at room temperature for 3 h. After allowing to stand overnight, the solvent was removed in vacuo and the residue was chromatographed on silica gel using heptane/ethyl acetate=8/2. The product fractions were combined and the solvent was removed in vacuo. 1.97 g (93%) of 169.3 were obtained.

169d) tert-Butyl (S)-2-((S)-4-phenyl-3-benzyl-4-methyl-2,5-dioxoimidazolidin-1-yl)-2-(2-methylpropyl)acetate (169.4)

1.9 g (3.59 mmol) of 169.3 in 190 ml of ethanol were hydrogenated over 76 mg of 10% palladium/carbon for 2 h. The catalyst was filtered off, the solvent was removed in vacuo, the residue was dissolved in ethyl acetate and the solution was washed with a 10% strength sodium hydrogen carbonate solution. The phases were separated and the organic phase was dried over sodium sulfate. After filtration, 1.3 g (80%) of 169.4 were obtained.

169e) (S)-2-((S)-4-Phenyl-3-benzyl-4-methyl-2,5-dioxoimidazolidin-1-yl)-2-(2-methylpropyl)acetate (169.5)

1.3 g (2.89 mmol) of 169.4 in a mixture of 10 ml of 6 N hydrochloric acid and 2 ml of tetrahydrofuran were heated under reflux for 4 h. After removal of the solvent in vacuo and chromatography of the residue using heptane/ethyl acetate=3/2, 510 mg (45%) of 169.5 were obtained.

169f) (S)-3-((b)-2-((S)-4-Phenyl-3-benzyl-4-methyl-2,5-dioxoimidazolidin-1-yl)-2-(2-methylpropyl)acetylamino)-3-(3,4-methylenedioxyphenyl)propionic acid The compound was prepared analogously to Example 1 by reaction of 169.5 with tert-butyl (S)-3-amino-3-(3,4-methylenedioxyphenyl)propionate (prepared analogously to S. G. Davis et al., Tetrahedron Asymmetry 1991, 2, 183), cleavage of the tert-butyl ester with trifluoroacetic acid as described in Example 1, and subsequent purification of the crude product by means of preparative HPLC (RP18: eluent: acetonitrile/water=50/120).

ES(+)-MS: 586.4 (M+H)+

The following two compounds can also be prepared analogously to Example 169:

(S)-3-((S)-2-((S)-4-Phenyl-3-benzyl-4-methyl-2,5-dioxoimidazolidin-1-yl)-2-(2-methylpropyl)acetylamino)-3-(2,4-dimethoxyphenyl)propionic acid

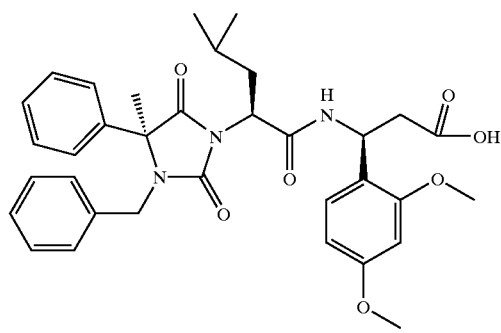

(by reaction of 169.5 with tert-butyl (S)-3-amino-3-(2,4-dimethoxyphenyl)propionate and subsequent cleavage of the tert-butyl ester with trifluoroacetic acid)

(S)-3-((S)-2-((S)-4-Phenyl-3-((4-biphenylyl)methyl)-4-methyl-2,5-dioxoimidazolidin-1-yl)-2-(2-methylpropyl)acetylamino)-3-(3,4-methylenedioxyphenyl)propionic acid

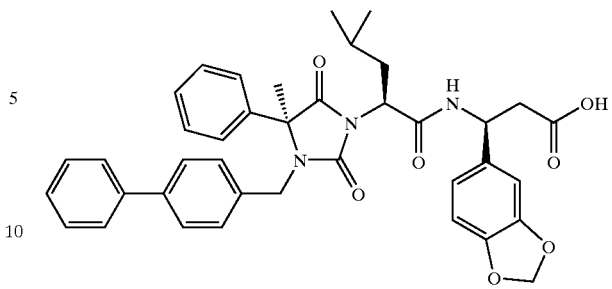

(by reaction of (S)-2-((S)-4-phenyl-3-((4-biphenylyl)methyl)-4-methyl-2,5-dioxoimidazolidin-1-yl)-2-(2-methylpropyl)acetic acid (obtainable by reaction of 169.2 with 4-phenylbenzyl bromide analogously to the synthesis of 169.3 and subsequent reactions analogously to the preparation of 169.5) with tert-butyl (S)-3-amino-3-(3,4-methylenedioxyphenyl)propionate and subsequent cleavage of the tert-butyl ester with trifluoroacetic acid)

Example 170
(S)-3-((R,S)-2-((R,S)-4-(4-Pyridyl)-3-benzyl-4-methyl-2,5-dioxoimidazolidin-1-yl)-2-(2-methylpropyl)acetylamino)-2-(1-adamantylmethyloxycarbonyl-amino)propionic acid

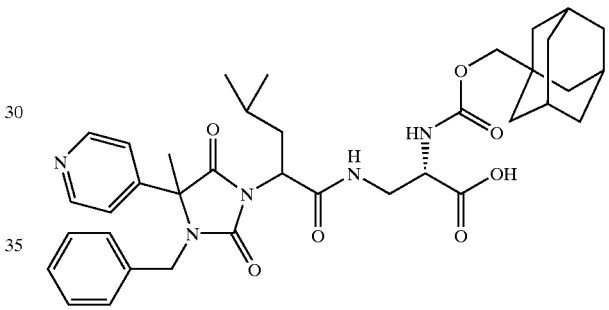

The compound was prepared analogously to Example 5 by reaction of 6.2 (see Example 6) with tert-butyl (S)-2-(1-adamantylmethyloxycarbonylamino)-3-aminopropionate (preparation see Example 4) and subsequent cleavage of the tert-butyl ester with trifluoroacetic acid.

ES(+)-MS: 674.5 (M+H)+

Example 171
General Procedure for the Preparation of 2-(N-((2,5-dioxoimidazolidin-1-yl)acetyl)-N-alkylamino)propionic Acids 171a) General working procedure for the preparation of N-alkylated β-alanine tert-butyl esters The primary alkylamine (50 mmol) was dissolved in 80 ml of methanol (if the alkylamine was employed in the form of the hydrochloride, the free amine was first liberated by the addition of potassium tert-butoxide (45 mmol)). 7.25 ml of tert-butyl acrylate (50 mmol) were added and after thorough mixing the mixture was allowed to stand at room temperature for 2 days. If any solids were present they were then filtered off, and the mixture was concentrated in a rotary evaporator at 60° C. and coevaporated twice with toluene. The residue was taken up in 100 ml of absolute diethyl ether and filtered, and the filtrate was rapidly concentrated. The product resulting in this way was obtained as an oil or solid and was employed in the next reaction step without further purification.

171b) General Working Procedure for the Acylation of N-alkylated β-alanine tert-butyl Esters with Hydantoincarboxylic Acids and Cleavage of the β-alanine tert-butyl Esters The hydantoincarboxylic acid (0.5 mmol) (see Example 128), 114 mg of N-ethyl-N'-(3-dimethylaminopropyl) carbodiimide hydrochloride (0.6 mmol), 70 mg of 1-hydroxybenzotriazole (0.6 mmol) and the N-alkylated β-alanine tert-butyl ester 1.0 mmol) were dissolved in 2 ml of absolute DMF and the solution was stirred at room temperature for 8 h. The reaction mixture was taken up in 100 ml of ethyl acetate and washed three times each with $KHSO_4$ solution (10%), $KHCO_3$ solution and water. The ethyl acetate phase was dried using $MgSO_4$ and concentrated to dryness. The residue was treated with 3 ml of trifluoroacetic acid and allowed to stand at room temperature for 1 h. The trifluoroacetic acid was removed in vacuo and the residue was coevaporated with toluene and diethyl ether.

Example 172

2-(N-(((R,S)-4-Phenyl-3-benzyl-4-methyl-2,5-dioxoimidazolidin-1-yl)acetyl)-N-benzylamino)propionic acid

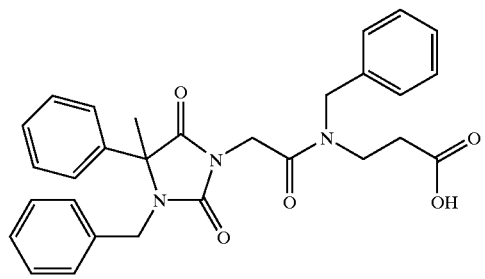

The compound was prepared starting from benzylamine according to the procedure in Example 171. Yield: 183 mg (73%) of colorless powder.

Example 173

2-(N-(((R,S)-4-Phenyl-3-benzyl-4-methyl-2,5-dioxoimidazolidin-1-yl)acetyl)-N-octylamino)propionic acid

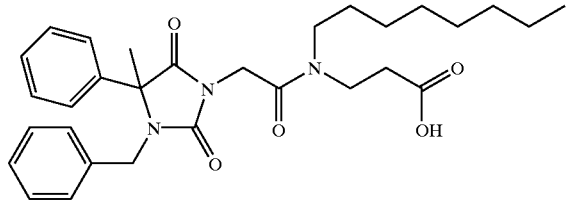

The compound was prepared starting from n-octylamine according to the procedure in Example 171. Yield: 293 mg (99%) of colorless oil.

Investigation of the Biological Activity

The test method used for the activity of the compounds of the formula I on the interaction between VCAM-1 and VLA-4 is an assay which is specific for this interaction. The cellular binding components, i.e., the VLA-4 integrins, are supplied in their natural form as surface molecules on human U937 cells (ATCC CRL 1593), which belong to the leucocytes group. The specific binding components used are genetically engineered recombinant soluble fusion proteins, consisting of the extracytoplasmatic domain of human VCAM-1 and the constant region of a human immunoglobulin of the subclass IgG1.

Test Method

Assay for the Measurement of the Adhesion of U937 Cells (ATCC CRL 1593) to hVCAM-1 (1-3)-IgG 1. Preparation of Human VCAM-1(1-3)-IgG and Human CD4-IgG A genetic construct for the expression of the extracellular domain of human VCAM-1, associated with the genetic sequence of the heavy chain of human immunoglobulin IgG1 (hinge, CH2 and CH3 regions), from Dr. Brian Seed, Massachusetts General Hospital, Boston, USA was employed (cf. Damle and Aruffo, Proc. Natl. Acad. Sci. USA 1991, 88, 6403–6407). The soluble fusion protein hVCAM-1(1-3)-IgG contained the three amino-terminal extracellular immunoglobulin-like domains of human VCAM-1 (Damle and Aruffo, Proc. Natl. Acad. Sci. USA 1991, 88, 6403). CD4-IgG (Zettlmeissl et al., DNA and Cell Biology 1990, 9, 347) served as a fusion protein for negative controls. The recombinant proteins were expressed as soluble proteins after DEAE/dextran-mediated DNA transfection in COS cells (ATCC CRL1651) according to standard procedures (Ausubel et al., Current Protocols in Molecular Biology, John Wiley & Sons, Inc., 1994).

2. Assay for the Measurement of the Adhesion of U937 Cells to hVCAM-1(1-3)-IgG 2.1 96-well microtiter test plates (Nunc Maxisorb) were incubated at room temperature for 1 hour with 100 μl/well of a goat-anti-human IgG antibody solution (10 μg/ml in 50 mM tris, pH 9.5). After removal of the antibody solution, washing was carried out once with PBS.

2.2 150 μl/well of a blocking buffer (1% BSA in PBS) was incubated on the plates at room temperature for 0.5 hour. After removal of the blocking buffer, washing was carried out once with PBS.

2.3 100 μl per well of a cell culture supernatant of transfected COS cells were incubated on the plates at room temperature for 1.5 hours. The COS cells were transfected with a plasmid which codes for the three N-terminal immunoglobulin-like domains of VCAM-1, coupled to the Fc part of human IgG, (hVCAM-1 (1-3)-IgG). The content of hVCAM-1 (1-3)-IgG was about 0.5–1 μg/ml. After removal of the culture supernatant washing was carried out once with PBS.

2.4 The plates were incubated at room temperature for 20 minutes with 100 μl/well of Fc receptor blocking buffer (1 mg/ml of γ-globulin, 100 mM NaCl, 100 μM $MgCl_2$, 100 μM $MnCl_2$, 100 μM $CaCl_2$, 1 mg/ml of BSA in 50 mM HEPES, pH 7.5). After removal of the Fc receptor blocking buffer washing was carried out once with PBS.

2.5 20 μl of binding buffer (100 mM NaCl, 100 μM $MgCl_2$, 100 μM $MnCl_2$, 100 μM $CaCl_2$, 1 mg/ml of BSA in 50 mM HEPES, pH 7.5) were initially introduced, and the substances to be tested were added in 10 μl of binding buffer and incubated for 20 minutes. The controls used were antibodies against VCAM-1 (BBT, No. BBA6) and against VLA-4 (Immunotech, No. 0764).

2.6 U937 cells were incubated in Fc receptor blocking buffer for 20 minutes and then added by pipette in a concentration of $1 \times 10^6$/ml and in an amount of 100 μl per well (final volume 125 μl/well).

2.7 The plates were slowly immersed at an angle of 45° in stop buffer (100 mM NaCl, 100 μM $MgCl_2$, 100 μM $MnCl_2$, 100 μM $CaCl_2$ in 25 mM tris, pH 7.5) and shaken off. The process was repeated.

2.8 50 μl/well of a dye solution (16.7 μg/ml of Hoechst Dye 33258, 4% formaldehyde, 0.5% Triton X-100 in PBS) were then incubated on the plates for 15 minutes.

2.9 The plates were shaken off and slowly immersed at an angle of 45° in stop buffer (100 mM NaCl, 100 μM MgCl$_2$, 100 µM MnCl$_2$, 100 µM CaCl$_2$ in 25 mM tris, pH 7.5). The process was repeated. Then, with the liquid, measurements were made in a cytofluorimeter (Millipore) (sensitivity: 5, filter: excitation wavelength: 360 nm, emission wavelength: 460 nm).

The intensity of the light emitted by the stained U937 cells is a measure of the number of the U937 cells adherent to the hVCAM-1 (1-3)-IgG and remaining on the plate and thus a measure of the ability of the added test substance to inhibit this adhesion. From the inhibition of the adhesion at various concentrations of the test substance, the concentration IC$_{50}$ was calculated which leads to a 50% inhibition of adhesion.

The following Test results were obtained:
Example U937/VCAM-1 Cell Adhesion Test

|   | IC$_{50}$ (µM) |
|---|---|
| 4 | 45 |
| 7 | 8 |
| 8 | 4.5 |
| 9 | 4 |
| 10 | 9.5 |

The disclosure of German Application 19741235.1, filed Sep. 18, 1997 (for which priority under 35 USC §119 is claimed) is hereby incorporated by references in its entirety.

Although only certain exemplary embodiments of this invention have been described in detail above, those skilled in the art will readily appreciate that many modifications are possible in the exemplary embodiments without materially departing from the teachings and advantages of this invention. Accordingly, all such modifications are intended to be included within the scope of this invention.

What is claimed is:

1. A method for the treatment of multiple sclerosis, comprising administering to a mammal in need thereof a compound of the formula I,

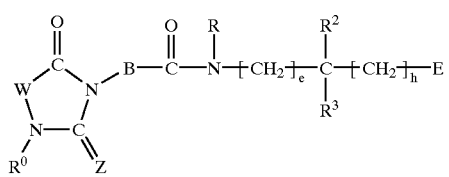

in which

W is $R^1$—A—$C(R^{13})$;

Z is oxygen or sulfur;

A is a direct bond or $(C_1-C_2)$-alkylene;

B is a divalent radical selected from the group consisting of $(C_1-C_6)$-alkylene, $(C_2-C_6)$-alkenylene, phenylene, phenylene-$(C_1-C_3)$-alkyl, $(C_1-C_3)$-alkylenephenyl, wherein the divalent $(C_1-C_6)$-alkylene radical can be unsubstituted or substituted by a radical selected from the group consisting of $(C_1-C_8)$-alkyl, $(C_2-C_8)$-alkenyl, $(C_2-C_8)$-alkynyl, $(C_3-C_{10})$-cycloalkyl, $(C_3-C_{10})$-cycloalkyl-$(C_1-C_6)$-alkyl, unsubstituted or substituted $(C_6-C_{14})$-aryl, $(C_6-C_{14})$-aryl-$(C_1-C_6)$-alkyl unsubstituted or substituted in the aryl radical, unsubstituted or substituted heteroaryl, and heteroaryl-$(C_1-C_6)$-alkyl unsubstituted or substituted in the heteroaryl radical;

E is tetrazolyl, $(R^8O)_2P(O)$, $HOS(O)_2$, $R^9NHS(O)_2$ or $R^{10}CO$;

R is hydrogen, $(C_1-C_8)$-alkyl, $(C_3-C_{12})$-cycloalkyl, $(C_3-C_{12})$-cycloalkyl-$(C_1-C_8)$-alkyl, unsubstituted or substituted $(C_6-C_{14})$-aryl, $(C_6-C_{14})$-aryl-$(C_1-C_8)$-alkyl unsubstituted or substituted in the aryl radical, unsubstituted or substituted heteroaryl, or heteroaryl-$(C_1-C_8)$-alkyl unsubstituted or substituted in the heteroaryl radical;

$R^0$ is $(C_3-C_{12})$-cycloalkyl, $(C_3-C_{12})$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, unsubstituted or substituted $(C_6-C_{14})$-aryl, $(C_6-C_{14})$-aryl-$(C_1-C_8)$-alkyl unsubstituted or substituted in the aryl radical, unsubstituted or substituted heteroaryl, heteroaryl-$(C_1-C_8)$-alkyl unsubstituted or substituted in the heteroaryl radical, H—CO, $(C_1-C_8)$-alkyl-CO, $(C_3-C_{12})$-cycloalkyl-CO, $(C_3-C_{12})$-cycloalkyl-$(C_1-C_8)$-alkyl-CO, $(C_6-C_{12})$-bicycloalkyl-CO, $(C_6-C_{12})$-bicycloalkyl-$(C_1-C_8)$-alkyl-CO, $(C_6-C_{12})$-tricycloalkyl-CO, $(C_1-C_{12})$-tricycloalkyl-$(C_1-C_8)$-alkyl-CO, unsubstituted or substituted $(C_6-C_{14})$-aryl-CO, $(C_6-C_{14})$-aryl-$(C_1-C_8)$-alkyl-CO unsubstituted or substituted in the aryl radical, unsubstituted or substituted heteroaryl-CO, heteroaryl-$(C_1-C_8)$-alkyl-CO unsubstituted or substituted in the heteroaryl radical, $(C_1-C_8)$-alkyl-S(O)$_n$, $(C_3-C_{12})$-cycloalkyl-S(O)$_n$, $(C_3-C_{12})$-cycloalkyl-$(C_1-C_8)$-alkyl-S(O)$_n$, $(C_6-C_{12})$-bicycloalkyl-S(O)$_n$, $(C_6-C_{12})$-bicycloalkyl-$(C_1-C_8)$-alkyl-S(O)$_n$, $(C_6-C_{12})$-tricycloalkyl-S(O)$_n$, $(C_6-C_{12})$-tricycloalkyl-$(C_1-C_8)$-alkyl-S(O)$_n$, unsubstituted or substituted $(C_6-C_{14})$-aryl-S(O)$_n$, $(C_6-C_{14})$-aryl-$(C_1-C_8)$-alkyl-S(O)$_n$ unsubstituted or substituted in the aryl radical, unsubstituted or substituted heteroaryl-S(O)$_n$ or heteroaryl-$(C_1-C_8)$-alkyl-S(O)$_n$ unsubstituted or substituted in the heteroaryl radical, wherein n is 1 or 2;

$R^1$ is an unsubstituted or substituted phenyl radical;

$R^2$ is hydrogen, $(C_1-C_8)$-alkyl, unsubstituted or substituted $(C_6-C_{14})$-aryl, $(C_6-C_{14})$-aryl-$(C_1-C_8)$-alkyl unsubstituted or substituted in the aryl radical or $(C_3-C_8)$-cycloalkyl;

$R^3$ is hydrogen, $(C_1-C_8)$-alkyl, unsubstituted or substituted $(C_6-C_{14})$-aryl, $(C_6-C_{14})$-aryl-$(C_1-C_8)$-alkyl unsubstituted or substituted in the aryl radical, unsubtituted or substituted heteroaryl, heteroaryl-$(C_1-C_8)$-alkyl unsubstituted or substituted in the heteroaryl radical, $(C_3-C_8)$-cycloalkyl, $(C_3-C_8)$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, $(C_2-C_8)$-alkenyl, $(C_2-C_8)$-alkynyl, $R^{11}$NH;

$R^8$ is hydrogen, $(C_1-C_{18})$-alkyl, unsubstituted or substituted $(C_6-C_{14})$-aryl or $(C_6-C_{14})$-aryl-$(C_1-C_8)$-alkyl which unsubstituted or substituted in the aryl radical;

$R^9$ is hydrogen, aminocarbonyl, $(C_1-C_{18})$-alkylaminocarbonyl, $(C_3-C_8)$-cycloalkylaminocarbonyl, unsubstituted or substituted $(C_6-C_{14})$-arylaminocarbonyl, $(C_1-C_{18})$-alkyl, unsubstituted or substituted $(C_6-C_{14})$-aryl or $(C_3-C_8)$-cycloalkyl;

$R^{10}$ is hydroxyl, $(C_1-C_{18})$-alkoxy, $(C_6-C_{14})$-aryl-$(C_1-C_8)$-alkoxy which is unsubtituted or substituted in the aryl radical, unsubstituted or substituted $(C_6-C_{14})$-aryloxy, $(C_1-C_8)$-alkylcarbonyloxy-$(C_1-C_6)$-alkoxy, $(C_6-C_{14})$-arylcarbonyloxy-$(C_1-C_6)$-alkoxy, amino or mono- or di($(C_1-C_{18})$-alkyl)-amino;

$R^{11}$ is hydrogen, $R^{12a}$, $R^{12a}$—CO, H—CO, $R^{12a}$—O—CO, $R^{12b}$—CO, $R^{12b}$—CS, $R^{12a}$—S(O)$_2$ or $R^{12b}$—S(O)$_2$;

$R^{12a}$ is (C$_1$–C$_{18}$)-alkyl, (C$_2$–C$_8$)-alkenyl, (C$_2$–C$_8$)-alkynyl, (C$_3$–C$_{12}$)-cycloalkyl, (C$_3$–C$_{12}$)-cycloalkyl-(C$_1$–C$_8$)-alkyl, unsubstituted or substituted (C$_6$–C$_{14}$)-aryl, (C$_6$–C$_{14}$)-aryl-(C$_1$–C$_8$)-alkyl unsubstituted or substituted in the aryl radical, unsubstituted or substituted heteroaryl, heteroaryl-(C$_1$–C$_8$)-alkyl unsubstituted or substituted in the heteroaryl radical, or the radical $R^{15}$;

$R^{12b}$ is amino, di-((C$_1$–C$_{18}$)-alkyl)-amino, or $R^{12a}$—NH;

$R^{13}$ is (C$_1$–C$_6$)-alkyl, unsubstituted or substituted (C$_6$–C$_{14}$)-aryl, (C$_6$–C$_{14}$)-aryl-(C$_1$–C$_6$)-alkyl unsubstituted or substituted in the aryl radical, (C$_3$–C$_8$)-cycloalkyl, or (C$_3$–C$_8$)-cyclo-(C$_1$–C$_6$)-alkyl;

$R^{15}$ is $R^{16}$—(C$_1$–C$_6$)-alkyl or $R^{16}$;

$R^{16}$ is a 6-membered to 24-membered bicyclic or tricyclic radical which is saturated or partially unsaturated and which contains none or one, two, three or four identical or different heteroatoms selected from the group consisting of nitrogen, oxygen, and sulfur and which is unsubstituted or substituted by one or more identical or different substituents selected from the group consisting of (C$_1$–C$_4$)-alkyl and oxo; and e and h independently of one another are 0 or 1;
in any of its stereoisomeric forms and mixtures thereof in any ratio, or a physiologically tolerable salt of the compound.

2. The method of claim 1, comprising administering a compound of the formula I, wherein W is $R^1$—A—C($R^{13}$);

Z is oxygen or sulfur;

A is a direct bond or methylene;

B is a divalent methylene radical or ethylene radical, both of which are unsubstituted or substituted by a radical selected from the group consisting of (C$_1$–C$_8$)-alkyl, (C$_2$–C$_8$)-alkenyl, (C$_2$–C$_8$)-alkynyl, (C$_3$–C$_{10}$)-cycloalkyl, (C$_3$–C$_{10}$)-cycloalkyl-(C$_1$–C$_6$)-alkyl, unsubstituted or substituted (C$_6$–C$_{14}$)-aryl, (C$_6$–C$_{14}$)-aryl-(C$_1$–C$_6$)-alkyl unsubstituted or substituted in the aryl radical, unsubstituted or substituted heteroaryl and heteroaryl-(C$_1$–C$_6$)-alkyl unsubstituted or substituted in the heteroaryl radical;

E is tetrazolyl or $R^{10}$CO;

R is hydrogen or (C$_1$–C$_8$)-alkyl;

$R^0$ is (C$_3$–C$_{12}$)-cycloalkyl, (C$_3$–C$_{12}$)-cycloalkyl-(C$_1$–C$_8$)-alkyl, (C$_6$–C$_{12}$)-bicycloalkyl, (C$_6$–C$_{12}$)-bicycloalkyl-(C$_1$–C$_8$)-alkyl, (C$_6$–C$_{12}$)-tricycloalkyl, (C$_6$–C$_{12}$)-tricycloalkyl-(C$_1$–C$_8$)-alkyl, unsubstituted or substituted (C$_6$–C$_{14}$)-aryl, (C$_6$–C$_{14}$)-aryl-(C$_1$–C$_8$)-alkyl unsubstituted or substituted in the aryl radical, unsubstituted or substituted heteroaryl, heteroaryl-(C$_1$–C$_8$)-alkyl unsubstituted or substituted in the heteroaryl radical, H—CO, (C$_1$–C$_8$)-alkyl-CO, (C$_3$–C$_{12}$)-cycloalkyl-CO, (C$_3$–C$_{12}$)-cycloalkyl-(C$_1$–C$_8$)-alkyl-CO, (C$_6$–C$_{12}$)-bicycloalkyl-CO, (C$_6$–C$_{12}$)-bicycloalkyl-(C$_1$–C$_8$)-alkyl-CO, (C$_6$–C$_{12}$)-tricycloalkyl-CO, (C$_1$–C$_{12}$)-tricycloalkyl-(C$_1$–C$_8$)-alkyl-CO, unsubstituted or substituted (C$_6$–C$_{14}$)-aryl-CO, (C$_6$–C$_{14}$)-aryl-(C$_1$–C$_8$)-alkyl-CO unsubstituted or substituted in the aryl radical, unsubstituted or substituted heteroaryl-CO, heteroaryl-(C$_1$–C$_8$)-alkyl-CO unsubstituted or substituted in the heteroaryl radical, (C$_1$–C$_8$)-alkyl-S(O)$_n$, (C$_3$–C$_{12}$)-cycloalkyl-S(O)$_n$, (C$_3$–C$_{12}$)-cycloalkyl-(C$_1$–C$_8$)-alkyl-S(O)$_n$, (C$_6$–C$_{12}$)-bicycloalkyl-S(O)$_n$, (C$_6$–C$_{12}$)-bicycloalkyl-(C$_1$–C$_8$)-alkyl-S(O)$_n$, (C$_6$–C$_{12}$)-tricycloalkyl-S(O)$_n$, (C$_6$–C$_{12}$)-tricycloalkyl-(C$_1$–C$_8$)-alkyl-S(O)$_n$, unsubstituted or substituted (C$_6$–C$_{14}$)-aryl-S(O)$_n$, (C$_6$–C$_{14}$)-aryl-(C$_1$–C$_8$)-alkyl-S(O)$_n$ unsubstituted or substituted in the aryl radical, unsubstituted or substituted heteroaryl-S(O)$_n$ or heteroaryl-(C$_1$–C$_8$)-alkyl-S(O)$_n$ unsubstituted or substituted in the heteroaryl radical, where n is 1 or 2;

$R^1$ is an unsubstituted or substituted phenyl radical;

$R^2$ is hydrogen or (C$_1$–C$_8$)-alkyl;

$R^3$ is hydrogen, (C$_1$–C$_8$)-alkyl, unsubstituted or substituted (C$_6$–C$_{14}$)-aryl, (C$_6$–C$_{14}$)-aryl-(C$_1$–C$_8$)-alkyl unsubstituted or substituted in the aryl radical, unsubstituted or substituted heteroaryl, heteroaryl-(C$_1$–C$_8$)-alkyl unsubstituted or substituted in the heteroaryl radical, (C$_3$–C$_8$)-cycloalkyl, (C$_3$–C$_8$)-cycloalkyl-(C$_1$–C$_8$)-alkyl, (C$_6$–C$_{12}$)-bicycloalkyl, (C$_6$–C$_{12}$)-bicycloalkyl-(C$_1$–C$_8$)-alkyl, (C$_6$–C$_{12}$)-tricycloalkyl, (C$_6$–C$_{12}$)-tricycloalkyl-(C$_1$–C$_8$)-alkyl, (C$_2$–C$_8$)-alkenyl or (C$_2$–C$_8$)-alkynyl or $R^{11}$NH;

$R^{10}$ is hydroxyl, (C$_1$–C$_{18}$)-alkoxy, (C$_6$–C$_{14}$)-aryl-(C$_1$–C$_8$)-alkoxy which is unsubstituted or substituted in the aryl radical, unsubstituted or substituted (C$_6$–C$_{14}$)-aryloxy, (C$_1$–C$_8$)-alkylcarbonyloxy-(C$_1$–C$_6$)-alkoxy, (C$_6$–C$_{14}$)-arylcarbonyloxy-(C$_1$–C$_6$)-alkoxy, amino or mono- or di-((C$_1$–C$_{18}$)-alkyl)-amino;

$R^{11}$ is hydrogen, $R^{12a}$, $R^{12a}$—CO, $R^{12a}$—O—CO, $R^{12b}$—CO, $R^{12b}$—CS or $R^{12a}$—S(O)$_2$;

$R^{12a}$ is (C$_1$–C$_{18}$)-alkyl, (C$_2$–C$_8$)-alkenyl, (C$_2$–C$_8$)-alkynyl, (C$_3$–C$_{12}$)-cycloalkyl, (C$_3$–C$_{12}$)-cycloalkyl-(C$_1$–C$_8$)-alkyl, unsubstituted or substituted (C$_6$–C$_{14}$)-aryl, (C$_6$–C$_{14}$)-aryl-(C$_1$–C$_8$)-alkyl unsubstituted or substituted in the aryl radical, unsubstituted or substituted heteroaryl, heteroaryl-(C$_1$–C$_8$)-alkyl unsubstituted or substituted in the heteroaryl radical, or the radical $R^{15}$;

$R^{12b}$ is amino, di-((C$_1$–C$_{18}$)-alkyl)-amino or $R^{12a}$—NH;

$R^{13}$ is (C$_1$–C$_6$)-alkyl;

$R^{15}$ is $R^{16}$—(C$_1$–C$_6$)-alkyl or $R^{16}$;

$R^{16}$ is a 6-membered to 14-membered bicyclic or tricyclic radical which is saturated or partially unsaturated and which contains none or one, two, three or four identical or different heteroatoms selected from the group consisting of nitrogen, oxygen, and sulfur and which is unsubstituted or substituted by one or more identical or different substituents from the group consisting of (C$_1$–C$_4$)-alkyl and oxo; and e and h independently of one another are 0 or 1;
in any of its stereoisomeric forms and mixtures thereof in any ratio, or a physiologically tolerable salt of the compound.

3. The method of claim 1, comprising administering a compound of the formula I, wherein W is $R^1$—A—C($R^{13}$);

Z is oxygen;

A is a direct bond or methylene;

B is a divalent methylene radical or ethylene radical, both of which are unsubstituted or substituted by a radical selected from the group consisting of (C$_1$–C$_8$)-alkyl, (C$_2$–C$_8$)-alkenyl, (C$_2$–C$_8$)-alkynyl, (C$_3$–C$_{10}$)-cycloalkyl, (C$_3$–C$_{10}$)-cycloalkyl-(C$_1$–C$_6$)-alkyl, unsubstituted or substituted (C$_6$–C$_{14}$)-aryl, (C$_6$–C$_{14}$)-aryl- ($C_1$–$C_6$)-alkyl, unsubstituted or substituted in the aryl radical, unsubstituted or substituted heteroaryl and heteroaryl-($C_1$–$C_6$)-alkyl unsubstituted or substituted in the heteroaryl radical;

E is $R^{10}CO$;

R is hydrogen or ($C_1$–$C_4$)-alkyl;

$R^0$ is ($C_3$–$C_{12}$)-cycloalkyl, ($C_3$–$C_{12}$)-cycloalkyl-($C_1$–$C_8$)-alkyl, ($C_6$–$C_{12}$)-bicycloalkyl, ($C_6$–$C_{12}$)-bicycloalkyl-($C_1$–$C_8$)-alkyl, ($C_6$–$C_{12}$)-tricycloalkyl, ($C_6$–$C_{12}$)-tricycloalkyl-($C_1$–$C_8$)-alkyl, unsubstituted or substituted ($C_6$–$C_{14}$)-aryl, ($C_6$–$C_{14}$)-aryl-($C_1$–$C_8$)-alkyl unsubstituted or substituted in the aryl radical, unsubstituted or substituted heteroaryl or heteroaryl-($C_1$–$C_8$)-alkyl unsubstituted or substituted in the heteroaryl radical;

$R^1$ is an unsubstituted or substituted phenyl radical;

$R^2$ is hydrogen or ($C_1$–$C_4$)-alkyl;

$R^3$ is ($C_1$–$C_8$)-alkyl, unsubstituted or substituted ($C_6$–$C_{14}$)-aryl, ($C_6$–$C_{14}$)-aryl-($C_1$–$C_4$)-alkyl unsubstituted or substituted in the aryl radical, unsubstituted or substituted heteroaryl, heteroaryl-($C_1$–$C_4$)-alkyl unsubstituted or substituted in the heteroaryl radical, ($C_3$–$C_8$)-cycloalkyl, ($C_3$–$C_8$)-cycloalkyl-($C_1$–$C_4$)-alkyl, ($C_6$–$C_{12}$)-bicycloalkyl, ($C_6$–$C_{12}$)-bicycloalkyl-($C_1$–$C_4$)-alkyl, ($C_6$–$C_{12}$)-tricycloalkyl, ($C_6$–$C_{12}$)-tricycloalkyl-($C_1$–$C_4$)-alkyl or $R^{11}NH$;

$R^{10}$ is hydroxyl, ($C_1$–$C_8$)-alkoxy, ($C_6$–$C_{14}$)-aryl-($C_1$–$C_8$)-alkoxy which is unsubstituted or substituted in the aryl radical, unsubstituted or substituted ($C_6$–$C_{14}$)-aryloxy, ($C_1$–$C_8$)-alkylcarbonyloxy-($C_1$–$C_6$)-alkoxy, ($C_6$–$C_{14}$)-arylcarbonyloxy-($C_1$–$C_6$)-alkoxy, amino or mono- or di-(($C_1$–$C_8$)-alkyl)-amino;

$R^{11}$ is $R^{12a}$, $R^{12a}$—CO, $R^{12a}$—O—CO, $R^{12b}$—CO, or $R^{12a}$—S(O)$_2$;

$R^{12a}$ is ($C_1$–$C_{10}$)-alkyl, ($C_2$–$C_8$)-alkenyl, ($C_2$–$C_8$)-alkynyl, ($C_3$–$C_{12}$)-cycloalkyl, ($C_3$–$C_{12}$)-cycloalkyl-($C_1$–$C_8$)-alkyl, unsubstituted or substituted ($C_6$–$C_{14}$)-aryl, ($C_6$–$C_{14}$)-aryl-($C_1$–$C_8$)-alkyl unsubstituted or substituted in the aryl radical, unsubstituted or substituted heteroaryl, heteroaryl-($C_1$–$C_8$)-alkyl optionally substituted in the heteroaryl radical, or the radical $R^{15}$;

$R^{12b}$ is amino, di-(($C_1$–$C_{10}$)-alkyl)-amino, or $R^{12a}$—NH;

$R^{13}$ is ($C_1$–$C_4$)-alkyl;

$R^{15}$ is $R^{16}$—($C_1$–$C_3$)-alkyl or $R^{16}$;

$R^{16}$ is a 7-membered to 12-membered bicyclic or tricyclic radical which is saturated or partially unsaturated and which can also contain one or two identical or different additional heteroatoms selected from the group consisting of nitrogen, oxygen, and sulfur and which can also be substituted by one or more identical or different substituents selected from the group consisting of ($C_1$–$C_4$)-alkyl and oxo;

e and h independently of one another are 0 or 1;

in any of its stereoisomeric forms and mixtures thereof in any ratio, or a physiologically tolerable salt of the compound.

4. The method of claim 1, comprising administering a compound of the formula I wherein W is $R^1$—A—$C(R^{13})$;

Z is oxygen;

A is a direct bond or methylene;

B is an unsubstituted methylene radical or a methylene radical which is substituted by a radical selected from the group consisting of ($C_1$–$C_8$)-alkyl, ($C_2$–$C_8$)-alkenyl, ($C_2$–$C_8$)-alkynyl, ($C_3$–$C_7$)-cycloalkyl, ($C_3$–$C_7$)-cycloalkyl-($C_1$–$C_4$)-alkyl, unsubstituted or substituted ($C_6$–$C_{10}$)-aryl, ($C_6$–$C_{10}$)-aryl-($C_1$–$C_4$)-alkyl unsubstituted or substituted in the aryl radical, unsubstituted or substituted heteroaryl, and heteroaryl-($C_1$–$C_4$)-alkyl unsubstituted or substituted in the heteroaryl radical;

E is $R^{10}CO$;

R is hydrogen or ($C_1$–$C_4$)-alkyl;

$R^0$ is ($C_6$–$C_{14}$)-aryl-($C_1$–$C_4$)-alkyl unsubstituted or substituted in the aryl radical or heteroaryl-($C_1$–$C_4$)-alkyl unsubstituted or substituted in the heteroaryl radical;

$R^1$ is an unsubstituted or substituted phenyl radical;

$R^2$ is hydrogen or ($C_1$–$C_4$)-alkyl;

$R^3$ is an unsubstituted phenyl radical or naphthyl radical or a phenyl radical or naphthyl radical which is substituted by one, two or three identical or different radicals selected from the group consisting of ($C_1$–$C_4$)-alkyl, ($C_1$–$C_4$)-alkoxy, hydroxyl, halogen, trifluoromethyl, nitro, methylenedioxy, ethylenedioxy, hydroxycarbonyl, ($C_1$–$C_4$)-alkoxycarbonyl, aminocarbonyl, cyano, phenyl, phenoxy, benzyl and benzyloxy, or $R^3$ is pyridyl, ($C_1$–$C_4$)-alkyl, ($C_2$–$C_4$)-alkenyl, ($C_2$–$C_4$)-alkynyl, ($C_5$–$C_6$)-cycloalkyl or $R^{11}NH$;

$R^{10}$ is hydroxyl, ($C_1$–$C_8$)-alkoxy, ($C_6$–$C_{10}$)-aryl-($C_1$–$C_4$)-alkoxy which is unsubstituted or substituted in the aryl radical, unsubstituted or substituted ($C_6$–$C_{10}$)-aryloxy, ($C_1$–$C_8$)-alkylcarbonyloxy-($C_1$–$C_4$)-alkoxy, ($C_6$–$C_{10}$)-arylcarbonyloxy-($C_1$–$C_4$)-alkoxy, amino or mono- or di-(($C_1$–$C_8$)-alkyl)-amino;

$R^{11}$ is $R^{12a}$, $R^{12a}$—CO, $R^{12a}$—O—CO, $R^{12b}$—CO, or $R^{12a}$—S(O)$_2$;

$R^{12a}$ is ($C_1$–$C_{10}$)-alkyl, ($C_2$–$C_8$)-alkenyl, ($C_2$–$C_8$)-alkynyl, ($C_3$–$C_{12}$)-cycloalkyl, ($C_3$–$C_{12}$)-cycloalkyl-($C_1$–$C_8$)-alkyl, unsubstituted or substituted ($C_6$–$C_{14}$)-aryl, ($C_6$–$C_{14}$)-aryl-($C_1$–$C_8$)-alkyl unsubstituted or substituted in the aryl radical, unsubstituted or substituted heteroaryl, heteroaryl-($C_1$–$C_8$)-alkyl unsubstituted or substituted in the heteroaryl radical, or the radical $R^{15}$;

$R^{12b}$ is amino, di-(($C_1$–$C_{10}$)-alkyl)-amino, or $R^{12a}$—NH;

$R^{13}$ is hydrogen or ($C_1$–$C_4$)-alkyl;

$R^{15}$ is $R^{16}$—($C_1$–$C_3$)-alkyl or $R^{16}$;

$R^{16}$ is a 7-membered to 12-membered bicyclic or tricyclic radical which is saturated and which can also contain one or two identical or different heteroatoms selected from the group consisting of nitrogen, oxygen, and sulfur and which is unsubstituted or substituted by one or more identical or different substituents selected from the group consisting of ($C_1$–$C_4$)-alkyl and oxo; and e and h independently of one another are 0 or 1;

in any of its stereoisomeric forms and mixtures thereof in any ratios, or a physiologically tolerable salt of the compound.

5. The method of claim 1, comprising administering a compound of the formula I in which B is unsubstituted methylene or methylene which is substituted by a ($C_1$–$C_8$)-alkyl radical, in any of its stereoisomeric forms and mixtures thereof in any ratio, or a physiologically tolerable salt of the compound.

6. The method of claim 1, comprising administering a compound of the formula I wherein $R^1$ is a phenyl radical, which is unsubstituted or substituted by one, two or three identical or different substituents from the group consisting of $(C_1-C_4)$-alkyl, $(C_1-C_4)$-alkoxy, halogen, amino, trifluoromethyl, hydroxyl, hydroxy-$(C_1-C_4)$-alkyl, methylenedioxy, ethylenedioxy, phenyl, phenoxy, benzyl, and benzyloxy, in any of its stereoisomeric forms and mixtures thereof in any ratio, or a physiologically tolerable salt of the compound.

7. The method of claim 1, comprising administering a compound of formula I wherein $R^1$ is a phenyl radical, wherein the phenyl radical is unsubstituted or substituted by one or two identical or different radicals selected from the group consisting of $(C_1-C_4)$-alkyl, $(C_1-C_4)$-alkoxy, halogen, trifluoromethyl, hydroxyl, hydroxy-$(C_1-C_4)$-alkyl, methylenedioxy, ethylenedioxy, phenyl, phenoxy, benzyl and benzyloxy, in any of its stereoisomeric forms or mixtures thereof in any ratio, or a physiologically tolerable salt of the compound.

8. The method of claim 1, comprising administering a compound of the formula I, wherein $R^1$ is an unsubstituted phenyl radical, in any of its stereoisomeric forms and mixtures thereof in any ratio, or a physiologically tolerable salt thereof.

* * * * *